US012734260B2

(12) United States Patent
Goldhawk et al.

(10) Patent No.: US 12,734,260 B2
(45) Date of Patent: Sep. 15, 2026

(54) BIOMEDICAL IMAGING OF BACTERIA AND VIRUSES

(71) Applicant: MULTI-MAGNETICS INCORPORATED, London (CA)

(72) Inventors: Donna E. Goldhawk, London (CA); Jeremy Burton, London (CA); Michael Silverman, London (CA); Frank S. Prato, London (CA); Sarah Catherine Donnelly, London (CA); Steven Foster, London (CA); Robert Terry Thompson, London (CA); Michael Zhang, London (CA)

(73) Assignee: Multi-Magnetics Incorporated, London, CA (US)

( * ) Notice: Subject to any disclaimer, the term of this patent is extended or adjusted under 35 U.S.C. 154(b) by 416 days.

(21) Appl. No.: 17/922,214

(22) PCT Filed: Apr. 28, 2021

(86) PCT No.: PCT/CA2021/050587
§ 371 (c)(1),
(2) Date: Oct. 28, 2022

(87) PCT Pub. No.: WO2021/217259
PCT Pub. Date: Nov. 4, 2021

(65) Prior Publication Data

US 2023/0201385 A1 Jun. 29, 2023

Related U.S. Application Data

(60) Provisional application No. 63/016,668, filed on Apr. 28, 2020.

(51) Int. Cl.
*A61K 51/12* (2006.01)
*A61K 9/00* (2006.01)

(52) U.S. Cl.
CPC ........ *A61K 51/1203* (2013.01); *A61K 9/0019* (2013.01)

(58) Field of Classification Search
CPC .............. A61K 51/1203; A61K 9/0019; C12N 2795/10121; C12N 2795/10321; C12N 1/20; C12N 7/00
See application file for complete search history.

(56) References Cited

FOREIGN PATENT DOCUMENTS

CA 3177303 A1 11/2021

OTHER PUBLICATIONS

Holman. Preparation of Tc99m-Labeled Pseudomonas Bacteriophage without Adversely Impacting Infectivity or Biodistribution. Biconjugate Chemistry. 2017. (Year: 2017).*

Mushtaq (Technetium-99m-based simple and convenient radiolabeling of *Escherichia coli* for in vivo tracking of microorganisms. Journal of Radioanalytical and Nuclear Chemistry. 2018) (Year: 2018).*

Ordonez (Molecular imaging of bacterial infections: Overcoming the barriers to clinical translation. Sci Transl Med. 2019 (Year: 2019).*

Febvre (PHAGE Study: Effects of Supplemental Bacteriophage Intake on Inflammation and Gut Microbiota in Healthy Adults. Nutrients. 2019.) (Year: 2019).*

Ju (Isolation of Commensal *Escherichia coli* Strains from Feces of Healthy Laboratory Mice or Rats. Bio-Protocol. 2018.) (Year: 2018).*

ATCC (Lactobacillus crispatus (ATCC® 33820™). ATCC. 2019) (Year: 2019).*

Villines (Everything you need to know about fecal transplants. Medical News Today. 2019.) (Year: 2019).*

Bansal (Novel 89Zr cell labeling approach for PET-based cell trafficking studies. EJNMMI Research. 2015) (Year: 2015).*

Perin (Radioactive technetium-99m labelling of *Salmonella abortusovis* for the assessment of bacterial dissemination in sheep by in vivo imaging. Veterinary Microbiology. 1997.) (Year: 1997).*

Vaquero (Positron Emission Tomography: Current Challenges and Opportunities for Technological Advances in Clinical and Preclinical Imaging Systems. Annu Rev Biomed Eng. 2017.) (Year: 2017).*

Zelmer (A new in vivo model to test anti-tuberculosis drugs using fluorescence imaging. Journal of Antimicrobial Chemotherapy. 2012.) (Year: 2012).*

Gosiewski (Comprehensive detection and identification of bacterial DNA in the blood of patients with sepsis and healthy volunteers using next-generation sequencing method—the observation of DNAemia. European Journal of Clinical Microbiology & Infectious Diseases. 2017. (Year: 2017).*

(Continued)

*Primary Examiner* — Michael G. Hartley
*Assistant Examiner* — Samantha L Mejias
(74) *Attorney, Agent, or Firm* — Smart & Biggar LP

(57) ABSTRACT

The invention relates to a non-invasive imaging method of bacteria. One embodiment comprises labeling the bacteria with a radioisotope, then delivering it to the gut of a human or animal. Another embodiment is to label bacteriophages, then administer them to a human or animal, so that they infect (and thus co-localize with) bacteria already resident in the human or animal. The bacteriophage can then be imaged, showing the location of the resident bacteria of interest. In another embodiment, the invention is related more generally to the labelling of bacteria or bacteriophages with a radio-metal or radioisotope to render the labeled gut bacteria and the bacteria in the body visible to nuclear medicine PET and SPECT imaging guided by functional/structural MRI and/or CT imaging. In another embodiment, the invention is related more generally to the labelling of bacteria or bacteriophages (both or just one) with a radio-metal or radioisotope to render the gut bacteria and the bacteria in the body visible to nuclear medicine PET and SPECT imaging guided by functional/structural MRI and/or CT imaging or visible by MRI alone or in combination with either PET or SPECT.

12 Claims, 28 Drawing Sheets

(56) References Cited

OTHER PUBLICATIONS

Li (In situ targeted MRI detection of Helicobacter pylori with stable magnetic graphitic nanocapsules. Nature Communications. 2016.) (Year: 2016).*
Chou (Ultra-wide range field-dependent measurements of the relaxivity of Gd1—xEuxVO4 nanoparticle contrast agents using a mechanical sample-shuttling relaxometer. 2017.). (Year: 2017).*
Extended European Search Report issued in corresponding European Patent Application No. 21796287.7 on Jul. 18, 2024.
Mushtaq, S et al.; "Technetium-99-m-based simple and convenient radiolabeling of *Escherichia coli* for in vivo tracking of microorganisms", Journal of Radioanalytical and Nuclear Chemistry (2018) 317:997-1003.
Abramov, V. et al.; "Pribiotic Properties of Lactobacillus crispatus 2,029: Homeostatic Interaction with Cervicovaginal Epithelial Cells and Antagonistic Activity to Genitourinary Pathogens"; Probiotics & Antimicro. Prot. (2014) 6:165-176.
Perin, F. et al.; Radioactive technetium-99m labelling of *Salmonella abortusovis* for the assessment of bacterial dissemination in sheep by in vivo imaging:; Veterinary Microbiology 51 (1997) 171-180.
Holman, Derek et al; "Preparation of Tc99m-Labeled Pseudomonas Bacteriophage Without Adversely Impacting Infectivity or Biodistribution"; Bioconjugate Chemistry, 2017, 28, 2698-2706.
Welling, Mick M. et al.; "Multimodal Tracking of Controlled *Staphylococcus aureus* Infections in Mice"; ACS Infectious Diseases; 2019, 5, 1160-1168.
Perin, "Radioactive technetium-99m labelling of *Salmonella abortusovis* for the assessment of bacterial dissemination in sheep by in vivo imaging". Veterinary Microbiology, 1997, vol. 51, pp. 171-180.
Holman, "Preparation of Tc99m-Labeled Pseudomonas Bacteriophage without Adversely Impacting Infectivity or Biodistribution". Bioconjugate Chem., 2017, vol. 28, pp. 2698-2706.
Welling, "Multimodal Tracking of Controlled *Staphylococcus aureus* Infections in Mice". ACS Infect. Dis . . . , 2019, vol. 5, pp. 1160-1168.
Geva-Zatorsky, "In vivo imaging and tracking of host-microbiota interactions via metabolic labeling of gut anaerobic bacteria". Nat. Med., 2015, vol. 21(9), pp. 1091-1100.
Petrik, "Siderophores for molecular imaging applications". Clin. Transl. Imaging, 2017, vol. 5, pp. 15-27.
Donnelly, S.C. et al.; "Using Magnetic Resonance Imaging to Visualize Probiotic and Urogenital Bacteria", 2019.
Donnelly, et al.; "Magnetic Resonance Imaging of Commensal and Pathogenic Bacteria", ISAPP 2019 2019.
Radioactive technetium-99m labelling of *Salmonella abortusovis* for the assessment of bacterial dissemination in sheep by in vivo imaging, Fabrice Perin et al., Veterinary Microbiology, vol. 51, pp. 171-180, Dec. 31, 1997.
Nvestigations of a99mTc-Labeled Bacteriophage as a Potential Infection-Specific Imaging Agent, Mary Rusckowski et al., The Journal of Nuclear Medicine, vol. 45, No. 7, pp. 1201-1208, Jul. 31, 2004.
Investigations of a99mTc-Labeled Bacteriophage as a Potential Infection-Specific Imaging Agent, Mary Rusckowski et al., The Journal of Nuclear Medicine, vol. 45, No. 7, pp. 1201-1208, Oct. 11, 2017.
Official Communication issued in corresponding Chinese Patent Application No. 202180031905.3 dated Jun. 17, 2024, with English translation.

* cited by examiner

BIOMEDICAL IMAGING OF BACTERIA AND VIRUSES

FIELD OF INVENTION

The invention relates to a non-invasive imaging method of bacteria. One embodiment comprises labelling the bacteria with a radioisotope, then delivering it to the gut of a human or animal. Another embodiment is to label bacteriophages, then administer them to a human or animal, so that they infect (and thus co-localize with) bacteria already resident in the human or animal. The bacteriophage and/or the infected bacteria can then be imaged, showing the location of the resident bacteria of interest. In another embodiment, the invention is related more generally to the labelling of bacteria or bacteriophages with a radioisotope including but not limited to radio-metals to render the labelled bacteria and the bacteria in the body visible to nuclear medicine PET and SPECT imaging guided by functional/structural MRI and/or CT imaging. In a further embodiment, manganese dependent bacteria are detected through changes in the MRI signal. If these manganese dependent bacteria are also labelled with a radioisotope then the PET/SPECT and MRI signals can be combined to quantitate the number of bacteria present within the subject.

BACKGROUND OF THE INVENTION

Bacteria of the gut are known to have an important role in the health and disease of humans and animals (Swank & Deitch, 1996). An understanding of the extent of this role is constrained by the inability to non-invasively and quantitatively image bacteria in vivo and ascertain their location, permeability across the intestinal barrier, and migration to other parts of the body.

Non-invasive mapping of cellular or subcellular events in living organisms, or molecular imaging, is an evolving and underdeveloped field. Currently known in vivo imaging methods have a number of drawbacks.

One such imaging method is the tracking of cells with reporter genes. This is typically done using optical platforms (such as bioluminescence, fluorescence) (Mezzanotte et al., 2017), by nuclear medicine (such as by tracking thymidine kinase activity) (Boerman et al., 2012), or by magnetic resonance imaging (MRI) (such as with magnetosome-like nanoparticles) (Goldhawk et al., 2009).

Optical imaging of bacteria in vivo typically involves invasive light detectors inserted into the gut and/or administration of a metabolic substrate such as luciferin, which may not be uniformly distributed to the transformed bacteria.

Nuclear medicine imaging methods are also known (e.g. positron emission tomography, PET; single photon emission computed tomography, SPECT). However, current nuclear medicine imaging methodology requires a radiotracer (e.g. metabolic substrate which is radioactive) and often results in a strong background signal in the gut that may obscure the target signal from labelled cells and is taken up by bacteria independent of bacteria species (Ordonez et al 2021).

Recent work (Donnelly et al., 2019) using MRI indicates that T2 relaxation times of many commensal and uropathogenic bacteria are intrinsically very short; hence further shortening with an MRI reporter producing iron nanoparticles, be they endogenous or exogenous, may not result in effective MRI contrast. In some bacteria with very short T2 times, there is a relatively large concentration of Mn which is a strong paramagnetic MRI contrast agent. This allows detection of these bacteria by MRI and also by PET if $^{52}$Mn (5.6 day half-life) is loaded into these bacteria.

Thus, imaging bacteria with reporter genes in a manner providing quantification or accurate localization of bacteria, including species identification, remains a challenge.

Another known in vivo imaging method is imaging specific bacterial cell surface markers with a radioligand that is intravenously injected. Such a method shows some promise for detecting bacterial infections in certain tissues (Ordonez et al., 2017, Hess et al., 2018). However, these methods may not be appropriate for detection of bacteria in the gut, since radioligands that are swallowed are likely to result in high intestinal background radiation signal, which would obscure the signal from bacteria.

A further known in vivo imaging method is direct labelling of bacteria prior to ingestion, which could allow the bacteria to be followed. Tracking by MRI using iron oxide particles (e.g. superparamagnetic iron oxide (SPIO) particles) (Shan, 2011) may have been successful in tracking injected mammalian cells; however, tracking bacteria is more challenging, since labelling is more challenging and, even if one is able to label the bacteria, the labelling would likely not change R2 relaxivity sufficiently, given that baseline bacterial R2 relaxation rates are often already high.

Iron-labelling has been effective for mammalian cell tracking but may not be effective for many species of bacteria. This is because an iron-sensitive MRI measure called T2 is inherently short in many bacteria, unlike T2 in most mammalian cells (Sengupta et al., 2014). Note that transverse relaxation rate, R2, is the inverse of T2, the relaxation time. Thus, a shorter T2 gives rise to a larger R2.

Thus, there remains a need to non-invasively, selectively, and quantitatively image gut microbiota.

SUMMARY OF THE INVENTION

According to one aspect of the present invention is provided a method of imaging microbiota in a subject, the method comprising: labelling bacteria or bacteriophage with a radioisotope; introducing the radioisotope labelled bacteria or bacteriophage into the subject; and functionally and/or structurally imaging the subject.

In certain embodiments, the labelling is labelling of bacteria, for example, gut bacteria.

In certain embodiments, the method further comprises isolating the gut bacteria from fecal material from the subject prior to labelling.

In certain embodiments, wherein gut bacteria are labelled and the gut bacteria comprise *Lactobacillus crispatus* ATCC33820.

In certain embodiments, the method further comprises mixing the radioisotope labelled gut bacteria into fecal material prior to its introduction into the subject.

In certain embodiments, the introducing of the radioisotope labelled bacteria comprises ingestion of the radioisotope labelled bacteria by the subject or administering the radioisotope labelled bacteria into the subject by way of intravenous, intraarterial, intrathecal, intramuscular, intradermal, subcutaneous, or intracavitary administration.

In certain embodiments, the introducing of the radioisotope labelled gut bacteria comprises depositing the radioisotope labelled gut bacteria into a duodenum of the subject.

In certain embodiments, the radioisotope is $^{89}$Zr, $^{64}$Cu, or $^{52}$Mn.

In certain embodiments, the radioisotope is $^{89}$Zr and the bacteria are labelled with a labelling agent comprising $^{89}$Zr-desferrioxamine-NCS ($^{89}$Zr-DBN).

In certain embodiments, the radioisotope is $^{52}$Mn.

In certain embodiments, the imaging comprises simultaneous positron emission tomography (PET) imaging and magnetic resonance imaging (MRI).

In certain embodiments, the imaging comprises sequential positron emission tomography (PET) imaging and magnetic resonance imaging (MRI).

In certain embodiments, the imaging comprises positron emission tomography (PET) imaging and computed tomography (CT) imaging.

In certain embodiments, the radioisotope is $^{111}$In, $^{177}$Lu, or $^{225}$Ac.

In certain embodiments, the radioisotope is $^{111}$In and the bacteria are labelled with a labelling agent comprising $^{111}$In-DOTA-NHS.

In certain embodiments, the imaging comprises single-photon emission computed tomography (SPECT) imaging and magnetic resonance imaging (MRI), optionally, simultaneously.

In certain embodiments, the imaging comprises sequential single-photon emission computed tomography (SPECT) imaging and magnetic resonance imaging (MRI).

In certain embodiments, the imaging comprises single-photon emission computed tomography (SPECT) imaging and computed tomography (CT) imaging.

In certain embodiments, the imaging comprises imaging the subject every 2 hours for the first 12 hours after administration of the label.

In certain embodiments, the imaging comprises imaging the subject for 30 min every 2 hours.

In certain embodiments, the imaging further comprises imaging the subject approximately once per radioisotope physical (or biological) half-life after the initial 12 hours until the radioisotope is no longer detected in the subject.

In certain embodiments, the labelling is of bacteriophage.

In certain embodiments, the bacteriophage is selected for its ability to infect the bacteria to be imaged.

In certain embodiments, the bacteriophage is selected for its specificity to the bacteria to be imaged.

In certain embodiments, the bacteriophage is selected from LH01-Myoviridae, LL5-Siphoviridae, T4D-Myoviridae, and LL12-Myoviridae and the bacteria to be imaged is *E. coli*.

In certain embodiments, the bacteriophage are gut bacteriophage.

In certain embodiments, the method comprises isolating the gut bacteriophage from fecal material from the subject prior to labelling.

In certain embodiments, the method further comprises mixing the radioisotope labelled bacteriophage or bacteria into fecal material prior to its introduction into the subject.

In certain embodiments, the introducing of the radioisotope labelled bacteriophage comprises ingestion of the radioisotope labelled bacteriophage by the subject or transplanting the radioisotope labelled bacteriophage into the subject.

In certain embodiments, radioisotope labelled bacteriophage is administered into the subject intravenously, intraarterially, intrathecally, intramuscularly, intradermally, subcutaneously, or intracavitarily.

In certain embodiments, the introducing of the radioisotope labelled gut bacteriophage comprises depositing the radioisotope labelled gut bacteriophage into a duodenum of the subject.

In certain embodiments, the radioisotope is $^{89}$Zr, $^{64}$Cu, or $^{52}$Mn.

In certain embodiments, the radioisotope is $^{89}$Zr and the bacteriophage are labelled with a labelling agent comprising $^{89}$Zr-desferrioxamine-NCS ($^{89}$Zr-DBN).

In certain embodiments, the radioisotope is $^{52}$Mn.

In certain embodiments, the imaging comprises simultaneous positron emission tomography (PET) imaging and magnetic resonance imaging (MRI).

In certain embodiments, the imaging comprises sequential positron emission tomography (PET) imaging and magnetic resonance imaging (MRI).

In certain embodiments, the imaging comprises positron emission tomography (PET) imaging and computed tomography (CT) imaging.

In certain embodiments, the radioisotope is $^{111}$In, $^{177}$Lu, or $^{225}$Ac.

In certain embodiments, the radioisotope is $^{111}$In and the bacteriophage are labelled with a labelling agent comprising $^{111}$In-DOTA-NHS.

In certain embodiments, the imaging comprises single-photon emission computed tomography (SPECT) imaging and magnetic resonance imaging (MRI), optionally, simultaneously.

In certain embodiments, the imaging comprises sequential single-photon emission computed tomography (SPECT) imaging and magnetic resonance imaging (MRI).

In certain embodiments, the imaging comprises single-photon emission computed tomography (SPECT) imaging and computed tomography (CT) imaging.

In certain embodiments, the imaging comprises imaging the subject every 2 hours for the first 12 hours after administration of the label.

In certain embodiments, the imaging comprises imaging the subject for 30 min every 2 hours.

In certain embodiments, the imaging further comprises imaging the subject approximately once per radioisotope physical (or biological) half-life after the initial 12 hours until the radioisotope is no longer detected in the subject.

According to another aspect of the present invention is provided a method of quantitatively 3D imaging microbiota in a subject, the method comprising: labelling bacteria, viruses, bacteriophage or other microorganism with a radioisotope; introducing the radioisotope labelled bacteria, viruses, bacteriophage or other microorganism into the subject; functionally and/or structurally imaging the subject; determining radioactivity of a biological sample from the subject; and mapping the radioactivity of the biological sample with the images to generate a quantitative 3D image of bacteria, viruses, bacteriophage or other microorganism distribution.

In certain embodiments, the method further comprises collecting a biological sample from the subject prior to introducing the radioisotope labelled bacteria, viruses, bacteriophage or other microorganism.

In certain embodiments, the method further comprises determining the radioactivity of the biological sample and an average number of radioisotope labels per bacterial cell, virus, bacteriophage, or other microorganism after introducing the radioisotope labelled bacteria, viruses, bacteriophage or other microorganism.

In certain embodiments, the radioactivity of the biological sample is determined using a calibrated radioactive counting detector.

In certain embodiments, the method further comprises combining one or more images resulting from the imaging, and the radioactivity per bacterial cell, virus, bacteriophage, or other microorganism, to generate a 3D image of the number of bacteria, virus, bacteriophage or other microorganism per voxel.

In certain embodiments, the biological sample is a stool sample and the imaged bacteria, viruses, bacteriophage, or other microorganisms are, respectively, gut bacteria, gut viruses, gut bacteriophage or other gut microorganisms.

In certain embodiments, the method further comprises segmenting the generated 3D image to identify the gut of the subject and to determine the number and location of radioisotope labelled gut microbiota in the gut of the subject.

In certain embodiments, the biological sample is one or more of a urine sample, a blood sample, and a saliva sample.

In certain embodiments, the method further comprises segmenting the generated 3D image to identify a region of interest external to a gut of the subject and to determine the number and location of radioisotope labelled microbiota in the region of interest.

In certain embodiments, the biological sample is analyzed to determine the kind and/or number of bacteria present using a) next generation sequencing and/or b) NMR relaxometry, by placing the biological sample in slow water exchange.

In certain embodiments, the method further comprises combining the number and kind of bacteria with the one or more images resulting from the imaging to determine the radioactivity of the bacteria, virus, bacteriophage or other microorganism in the biological sample and the radioactivity per bacterium.

According to a further aspect of the present invention is provided a method of imaging microbiota in a gut of a subject, the method comprising: labelling gut bacteria, gut viruses, gut bacteriophage, or other gut microorganism with a radioisotope; introducing the radioisotope labelled gut bacteria, gut viruses, gut bacteriophage, or other gut microorganism into the subject; and functionally and/or structurally imaging the subject.

In certain embodiments, the method further comprises isolating the gut bacteria, gut viruses, gut bacteriophages or other gut microorganism from fecal material from the subject or from another subject.

In certain embodiments, the method further comprises mixing the radioisotope labeled gut bacteria, gut viruses, gut bacteriophage, or other gut microorganism into fecal material prior to introduction into the subject.

In certain embodiments, the labelling is of a bacteria, and wherein the functionally and/or structurally imaging the subject provides a first image, further comprising, after functionally and/or structurally imaging the subject: selecting a bacteriophage specific to the labelled bacteria and administering said bacteriophage to the subject; functionally and/or structurally imaging the subject a second time, to provide a second image; comparing said first image and said second image, where differences between the first image and the second image are indicative of a location of the bacteria.

In certain embodiments, the labelling is of a bacteriophage, and wherein the functionally and/or structurally imaging the subject provides a second image, further comprising, before labelling the bacteriophage with the isotope: introducing bacteria into the subject; wherein the bacteriophage is selected for its specificity to the bacteria.

According to a further aspect of the present invention is provided a method of imaging microbiota in a subject, the method comprising: functionally and/or structurally imaging the subject, to obtain a first image; introducing a manganese dependent bacteria into the subject; and functionally and/or structurally imaging the subject again, to obtain a second image; comparing the first image and the second image, wherein changes in imaging indicate location of the bacteria.

In certain embodiments, the manganese dependent bacteria is mixed with fecal matter before introduction into the subject.

In certain embodiments, the functional and/or structural imaging is through MRI and the first image and the second image are R2/R2* images.

Additional features and advantages of the invention will be described hereinafter which form the subject of the claims of the invention. It should be appreciated by those skilled in the art that the specific embodiment disclosed herein may be readily utilized as a basis for modifying or designing other structures for carrying out the same purposes of the present invention. It should also be realized by those skilled in the art that such equivalent constructions do not depart from the scope of the invention. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF DRAWINGS

(FIG. 17A: 9-72 hour time points; FIG. 17B: 7-24 day time points)

FIG. 23 (*b*) shows the specific uptake value of $^{89}Zr$ as a function of time after said injection.

DETAILED DESCRIPTION OF THE INVENTION

The present invention relates the labelling of microbiota (for example, bacteria, yeast, or bacteriophage) with a radioisotope tracer, such as the positron emission tomography (PET) label $^{89}Zr$-DBN, which covalently binds to amine groups associated with cell surface proteins. Specifically, the present invention relates to radiolabelling these cells for nuclear imaging while using the endogenous contrast of microorganisms (e.g. bacteria) for additional cell tracking by MRI. This invention is, therefore, particularly well-suited to imaging with hybrid PET/MRI. In another embodiment, the bacteria can be labelled with $^{52}Mn$ allowing detection by PET of manganese-dependent bacteria. Other radiolabels may also be used.

In one embodiment is disclosed a method of imaging bacteria, either directly (for example, using $^{89}Zr$-DBN or $^{52}Mn$ or $^{111}In$), or indirectly by labelling bacteriophage (for example, with $^{89}Zr$-DBN) which are known to infect the bacteria of interest, allowing those bacteriophage to come into contact with the bacteria of interest, and using PET/MRI and PET/CT to image the bacteria, since they will be co-located with the labelled bacteriophage. In a corollary embodiment, non-labelled bacteriophage can be utilized to attenuate the radio-signal when they find, and infect, and lyse, the radio-labelled bacteria.

Figure 20:
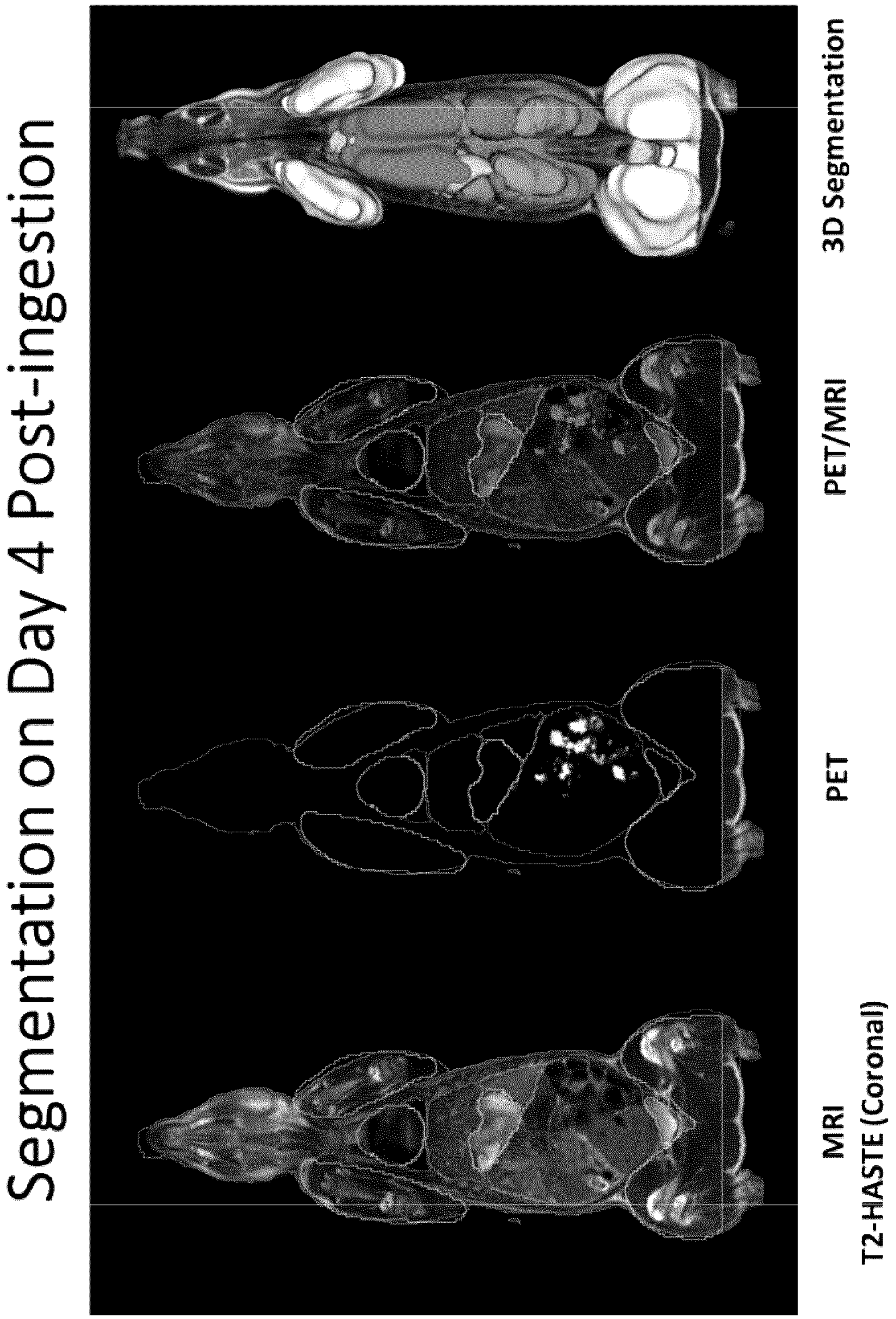
FIG. 20 shows PET/MRI segmentation of the pig on day 4 post-ingestion of $^{89}Zr$-labelled probiotic.

$^{89}Zr$ has a half-life of 3.3 days; the prior art has indicated that intravenous injection of $^{89}Zr$-phosphate in a dog has shown acceptable bone visualization for 20 days if there is good clearance of $^{89}Zr$ from background (see FIG. 20, from Thiessen et al., 2017). The $^{52}Mn$ isotope has a half-life of 5.6 days and is predicted to detect bacteria for even longer, and is likely be even more effective in manganese—dependent bacteria.

As noted in Thiessen et al., FIG. 20 illustrates longitudinal imaging of $^{89}Zr$-phosphate by PET/MRI in a dog. Image a) shows coronal (upper) and sagittal (lower) views of the maximum intensity projections (MIPs) from Day 0 to Day 16. PET/MRI provided additional anatomical information. For reference, the kidney is marked with an arrow. Image b) shows mean standard uptake values (SUV) in different regions were relatively stable by day 8, with SUV~3 in liver, lungs, and kidneys, and ~10 in bone, when averaged over days 8-16.

Figure 18:
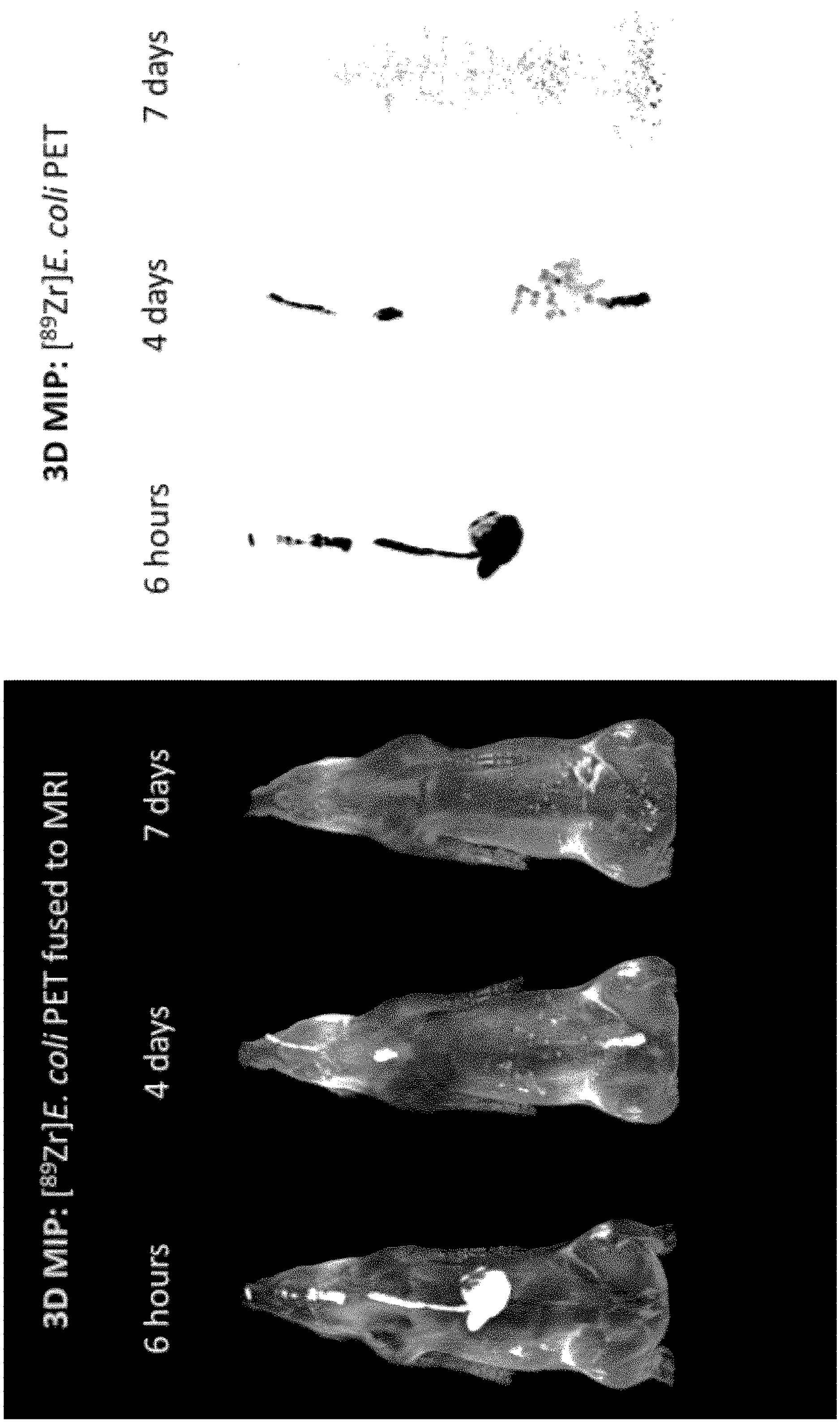
FIG. 18 images show $^{89}Zr$-labelled bacteria (*E. coli* Nissle, probiotic) ingested by a pig, with PET maximum intensity projections (MIP) alone (at right) and these registered to MRI (coronal T1-weighted in-phase Dixon, at left)

In the current method, preferably, the bacteria or bacteriophage is labelled prior to introduction into the host. Labelling (and washing and isolating the labelled bacteria/bacteriophage) results in background radiation that is negligible. Calibration of activity per bacteria can be determined by analysis of fecal material eliminated after ingestion of labelled bacteria, since the signal, i.e. $^{89}Zr$ concentration per bacterial cell, will dilute as bacteria proliferate. FIG. 18 shows the 3-D distribution of labelled bacteria (*E. coli* Nissle) in the gut at 6 hrs, 4 days and 7 days.

It has been found that the spin-spin relaxation rate (also referred to as the transverse relaxation rate and designated as R2) of many bacteria is much greater than that of mammalian soft tissues, due to high concentrations of manganese in select bacterial cells. Typical R2 values in mammalian soft tissue are on the order of 20 $s^{-1}$ while the R2 of different species of bacteria can be as high as 300 $s^{-1}$. Given that bacteria make up as much as 60% of the dry mass of feces, bacteria with high R2 values can be used to produce MRI images of the gut, with sufficient signal to noise ratio to allow 3D discrimination of bacteria located in the gut. Susceptibility artifacts caused by pockets of air are distinguished by registering MRI with PET images of radiolabelled bacteria.

It has been found that identification of specific bacterial species with high R2 can sometimes be difficult due to the presence of bacteria with lower values of R2, which raise the background signal, and that the bacteria and aqueous fluid in the gut may be typically in fast water exchange, particularly for bacteria with relatively short values of R2/R2*.

Figure 7:
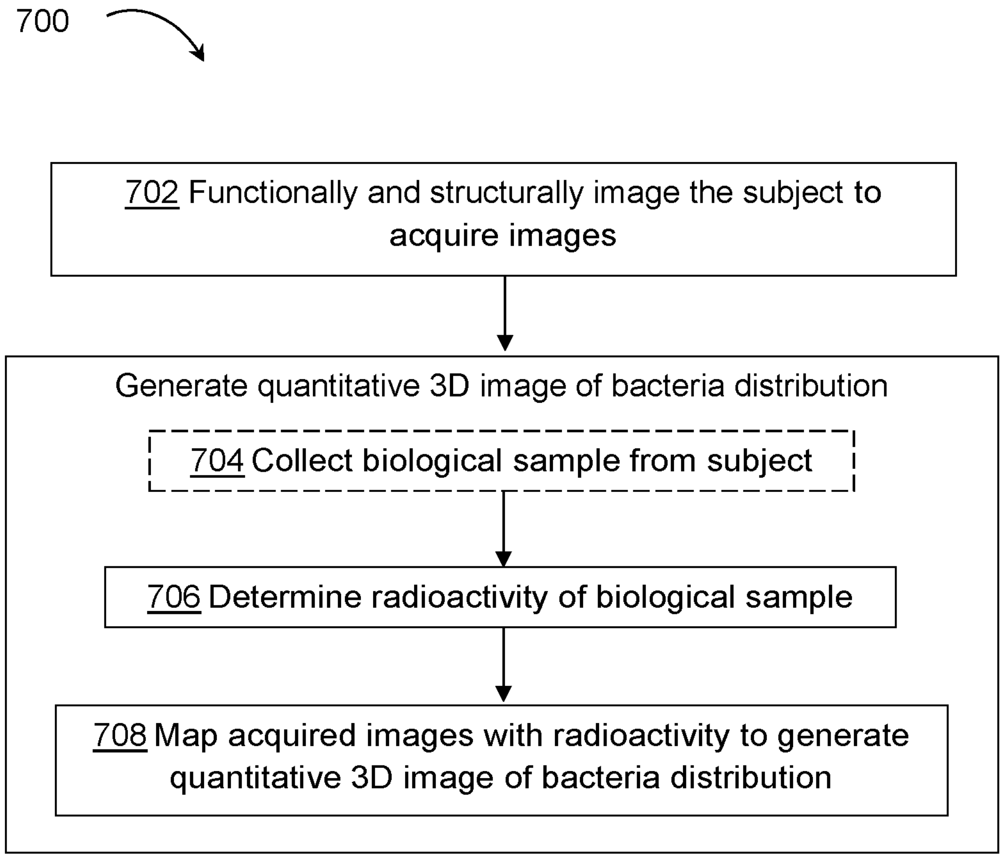
FIG. 7 is a flowchart setting forth the steps of an example method for 3D imaging bacteria distribution in a subject.

It has been found that when bacteria with high R2 values (on the order of 300 $s^{-1}$) represent at least about 25% of the bacterial population in a region of interest then, even in fast exchange, these bacteria can be readily and selectively detected and identified by R2 imaging. As shown in FIG. 7, discussed in greater detail below, when the contribution of "high R2" bacteria is diluted ¼, the resulting R2 values are approximately 80 $s^{-1}$; this has been found to be more than adequate for selectively detecting and identifying bacteria by R2 imaging.

Figure 11:
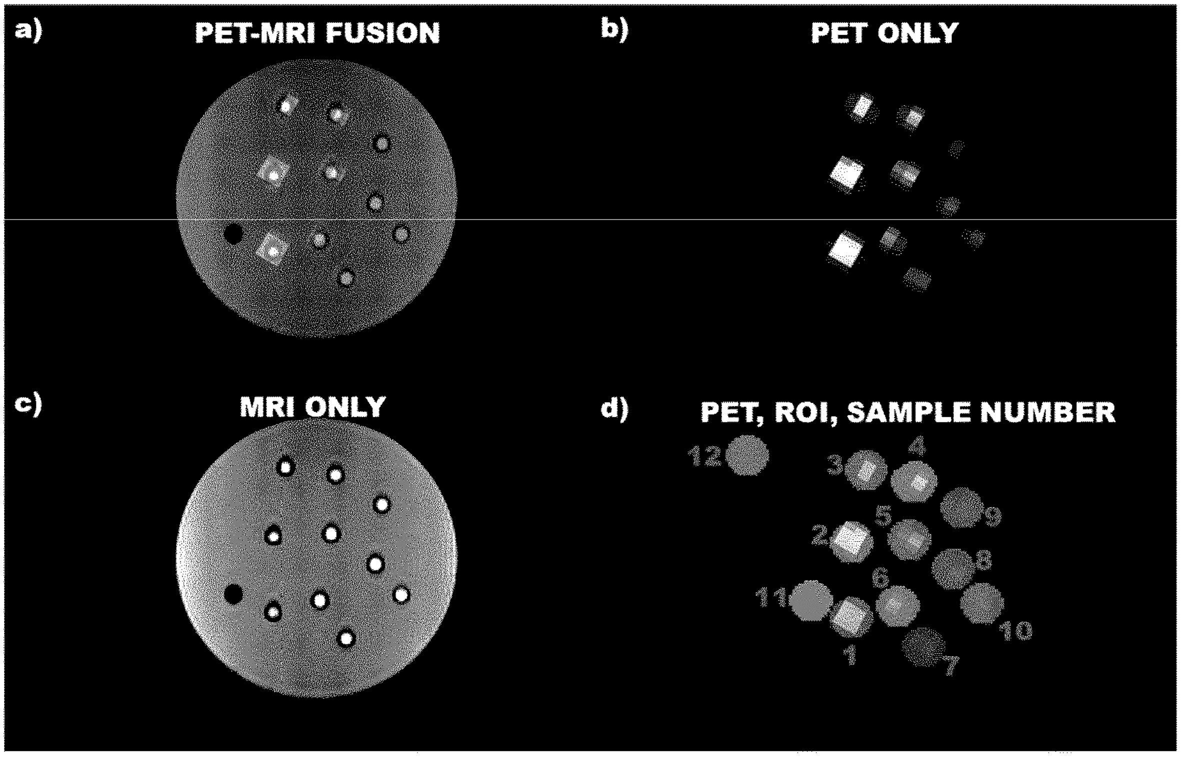
FIG. 11 shows the PET/MRI of a gelatin phantom containing serially diluted *L. crispatus* ATCC33820.

Identification of bacteria in fecal samples, or other biological specimens such as saliva, urine or blood, can be determined and quantified using either a) standard bacteriology methods, such as next generation sequencing and/or b) by NMR relaxometry, when the fecal material (or other biological sample) can be processed to allow each bacterial strain to be in slow water exchange. Accordingly, if the different bacteria with different R2 values are in fast exchange, then only a weighted average of R2 can be measured, i.e. only one distinct R2 value can be measured. If, however, the bacteria with different R2 values are in slow exchange then the individual R2 values can be measured. For example, the data in FIG. 11 shows that *Lactobacillus gasseri* ATCC33323 could be quite readily distinguished from *Staphylococcus aureus* Newman due to their different R2 values.

The present invention also relates to labelling of bacteriophages. For example, this imaging may be useful in understanding the role of bacteriophage for the treatment of toxic bacteria (Hampton et al., 2020; Cisek et al., 2017). Also, the labelled bacteriophage can be administered into the organism to determine the presence of a species of bacteria specific to the species of bacteriophage labelled and introduced.

According to a further aspect, this invention is directed towards determining extent and persistence of engraftment following treatment with live bacteria.

FIGS. 1 to 6 illustrate exemplary methods 100, 200, 300, 400, 500 and 600 for imaging microbiota (for example, gut bacteria) in a subject, and in particular, imaging of bacterial concentrations (directly using radioisotope labelled bacteria, indirectly using radioisotope labelled bacteriophages with radiolabelled bacteria or with non-radiolabelled bacteria, using non-radioactive labelled bacteriophage with radiolabelled bacteria or MRI detection of radiolabelled and non-radiolabelled manganese dependent bacteria) throughout the body of small animals, large animals, and humans using $^{89}$Zr and $^{111}$In-DBN as the radioisotope. FIGS. 1 to 7 show essential steps in solid rectangles, and optional (though often preferable) steps in stippled rectangles.

Figure 1:
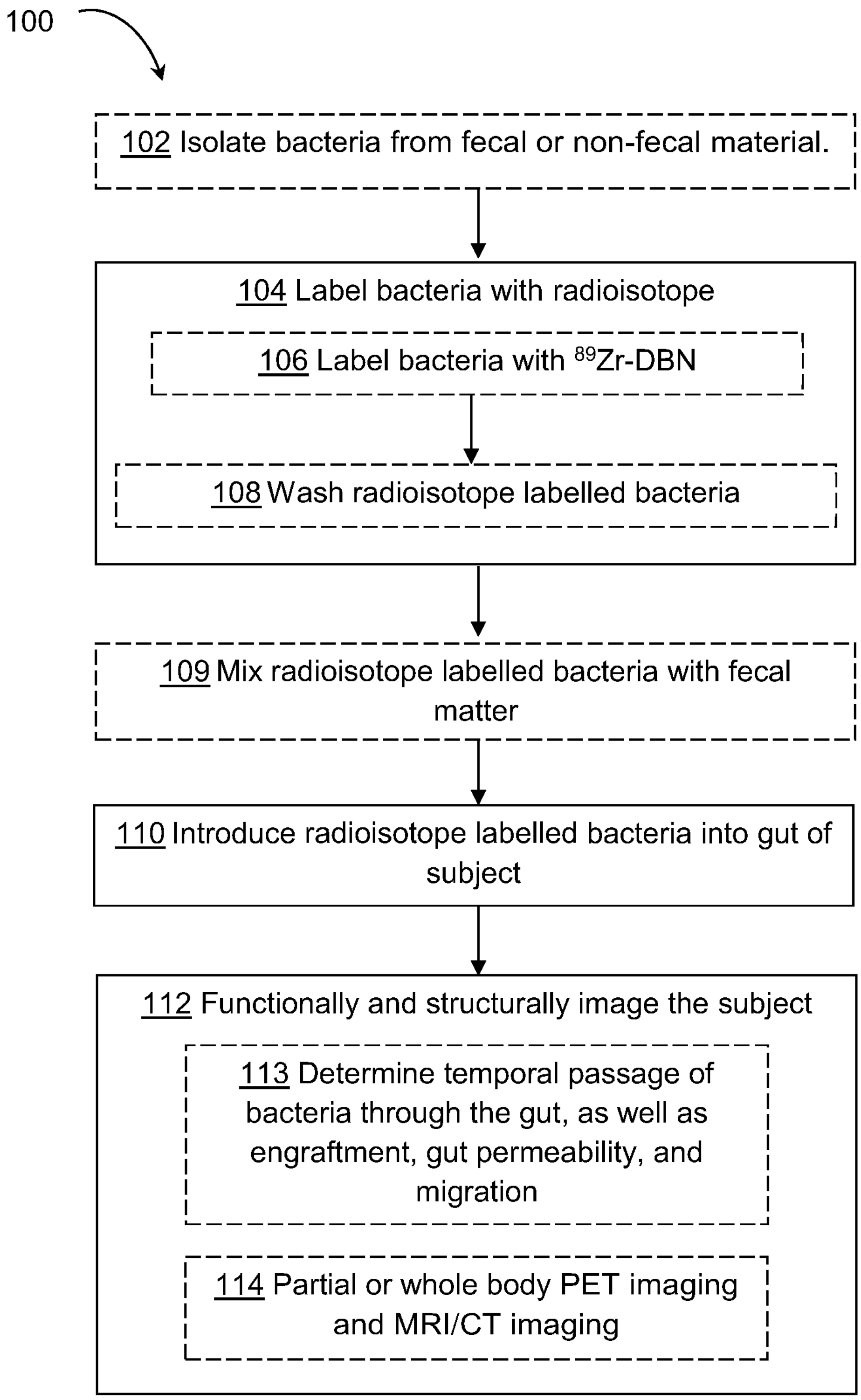
FIG. 1 is a flowchart setting forth the steps of an example method for imaging bacteria (for example, gut bacteria) in a subject.

In FIG. 1, at 102, bacteria may be isolated from fecal or non fecal material. For example, such bacteria may be gut bacteria, or may be commercially available bacteria, such as a probiotic supplement. One example of such bacteria is *Lactobacillus crispatus*, such as strain ATCC33820. As understood, other strains of aerobic and anaerobic bacteria may be used. Though isolation from fecal material is shown, this methodology could equally be applied to bacterial strains from other sources that can be isolated and labelled, such as those used for probiotic, food, animal or environmental purposes.

Examples of bacterial species include other members of the genera, *Lactobacillus, Bifidobacteria, Prevotella, Bacteroides, Clostridium, Akkermansia, Ruminococcus, Enterococcus, Streptococcus, Escherichia*, Lachnospiracae, *Blautia, Fusobacterium, Dorea, Roseburia* and *Faecalibacterium*. For example, examples of bacteria useful for labelling in the present method include *L. crispatus* (such as *L. crispatus* ATCC33820), *E. coli* (such as *E. coli* BL21(DE3), *E. coli* MG1655, *E. coli* Nissle, *E. coli* 25922, *E. coli* 67, *E. coli* AD110, *E. coli* GR-12, *E. coli* 536, *E. coli* J96), *Enterococcus faecalis* (such as *E. faecalis* ATCC33186), *Klebsiella pneumoniae* (such as *K. pneumoniae* 280), *Proteus mirabilis* (such as *P. mirabilis* 296), *Pseudomonas aeruginosa* (such as *P. aeruginosa* PA01), *Staphylococcus aureus* (such as *S. aureus* Neuman and *S. aureus* USA300), *S. epidermidis* (such as *S. epidermidis* ATCC35984), *L. gasseri* (such as *L. gasseri* ATCC33323), *L. reuteri* (such as *L. reuteri* RC14), *L. rhamnosus* (such as *L. rhamnosus* GR-1), At 104, the isolated bacteria are labelled with a radioisotope that can be imaged using PET or SPECT. In one example embodiment, at 106, the *Lactobacillus crispatus* ATCC33820 bacteria may be labelled with the radioisotope $^{89}$Zr, using labelling agent $^{89}$Zr-desferrioxamine-NCS ($^{89}$Zr-DBN) by adapting a published procedure (Bansal et al., 2015).

The radioisotope, such as $^{89}$Zr, is first isolated in a solution, such as a zirconium hydrogen phosphate solution, $^{89}Zr(HPO_4)_2$. The radioisotope is then chelated to form a labelling agent, such as $^{89}$Zr-DBN using DFO-Bz-NCS. $^{89}$Zr-DBN is a first generation prototypic labelling agent. Chelation of $^{89}$Zr to DBN has been adapted from Bansal et al. The DFO moiety is the chelating end of DBN. The isothiocyanato-benzyl group is the conjugating moiety that covalently binds primary amines on protein found at the cell surface. Desferrioxamine (DFO), or an improved chelator (Bhatt et al., 2018; Berg et al., 2020), may then be used as the chelating agent for the zirconium atom. DFO is conjugated to a p-isothiocyanato-benzyl group or an improved conjugating agent (Berg et al., 2020) to achieve the resulting $^{89}$Zr-desferrioxamine-NCS, or $^{89}$Zr-DBN.

Alternately, rather than producing $^{89}$Zr-DBN or its precursor $^{89}Zr(HPO_4)_2$, these may simply be purchased from a third party, including select cyclotron and radiochemistry facilities, where they are readily commercially available.

The isolated bacteria are then combined with the $^{89}$Zr labelling agent (for example, $^{89}$Zr-DBN) and incubated. During incubation, the $^{89}$Zr-DFO-labelled agent covalently binds to primary amines of cell surface proteins of the isolated bacteria, thus, randomly labelling the external cell surface of the bacteria with the radioisotope.

The radioisotope labelled bacteria are then separated from unbound $^{89}$Zr at 108. For example, the sample may be "washed" by centrifugation to remove unbound radiotracer remaining in the supernatant from the radiolabelled bacterial pellet.

In mammalian cells, radioactivity as high as 0.5 Bq/cell has been shown to be safe. Since bacteria are much smaller than mammalian cells, approximately 100 times smaller in terms of surface area, the target radioactivity level per bacterial cell may be reduced to approximately 0.005 Bq/cell. As bacteria vary in size, when the size is known, a better calculation would be 0.5 Bg/cell times the ratio of bacteria surface area to the area of a 10 micron sphere.

Optionally, at 109, the washed radioisotope-labelled bacteria may be mixed into recipient fecal material prior to its introduction into a subject, in an administration of the known microbial therapy referred to as fecal microbiota transplantation (FMT). This may allow imaging of FMT bacteria, helping determining the effectiveness of the transplantation and therapy, for example.

At 110, the radioisotope labelled bacteria are introduced into the subject. In some applications, the radiolabelled bacterial cells or fecal microbiota are transplanted into the duodenum of the subject using a feeding tube. The radiolabelled bacterial cells may be the bacteria in probiotic products (FIG. 18) or fermented food which is consumed. In other applications, the radiolabelled bacterial cells are simply swallowed, or otherwise ingested, by the subject.

The subject is then imaged at 112. Imaging may involve positron emission tomography (PET) imaging, and magnetic resonance imaging (MRI) or X-ray computed tomography (CT) imaging. Imaging with PET, MRI and CT may take place simultaneously (see FIG. 11) or sequentially, and method 100 may include one or more rounds of imaging. As well, the gut, the surrounding regions around the gut, or the entire subject may be imaged. In certain example embodiments, at 113 one is able to determine the temporal passage of bacteria through the gut, as well as engraftment, gut permeability, and/or migration. In certain example embodiments, at 114, the functional and structural imaging of the subject includes partial or whole body SPECT imaging and/or MRI/CT imaging.

In particular, FIG. 11 illustrates simultaneous PET/MRI of a gelatin phantom containing wells of serially diluted *Lactobacillus crispatus* strain ATCC33820. Image a) depicts a slice from a 3D PET and MRI dataset, co-registered within a single image. From the respective PET (b) and MRI (c) data sets, regions of interest (ROI) were defined (d). For PET analysis, the mean values from ROI of duplicate samples were determined. Sample numbers correspond to each serial dilution and include a plastic peg (11) and background (12).

At 114, after the radioisotope labelled bacteria are transplanted or ingested, the subject may undergo PET/MRI for 30 min every 2 hours for 12 hours. Subsequently, imaging may further be performed every 4 days until the $^{89}$Zr is no longer detectable. Repetitive imaging may be performed up to approximately 4 weeks, depending on the gut motility associated with the individual subject, the persistence of bacteria in the body, and the half-life of the radioisotope. Combining MRI and/or CT with radionuclide imaging allows the segmented 3D MRI or CT image to be used to segment the PET images. For proper segmentation of the PET image by the MRI or CT image it is preferable that gut mobility is low between the PET and MRI/CT data acquisition. In animal studies, anesthesia will reduce gut mobility whereas in humans gut mobility is typically reduced using drugs like hyoscine butylbromide during MRI examination.

In alternate applications, the subject may undergo PET/MRI imaging, or PET/CT imaging followed by MRI. The frequency and length of the imaging of the subject may also vary from 30 min every 2 hours for 12 hours, and may vary from subsequently being performed every 4 days until the $^{89}$Zr is no longer detectable. For example, imaging may be performed once per radioisotope physical (or biological) half-life, such as once every 3.3 days for $^{89}$Zr, until the $^{89}$Zr is no longer detectable.

Labelling bacteria with, for example, $^{89}$Zr-DBN followed by PET/MRI allows determination of engraftment in the gut of the introduced bacteria, permeability of the bacteria out of the gut followed by migration of the bacteria to different locations in the body.

While method 100 has been described with $^{89}$Zr as the radioisotope, other metal-based positron radioisotopes may alternately be used, like for example $^{52}$Mn (with a 5.5 day half-life). As well, single photon radioisotopes, for example $^{111}$In (2.8 day half-life) may be used. In addition, heavy metal radioisotopes, such as $^{177}$Lu (a beta emitter and single photon emitter, 6.6 day half-life) and $^{225}$Ac (an alpha emitter and single photon emitter, 10 day half-life) can be used to label the bacteria.

Figure 2:
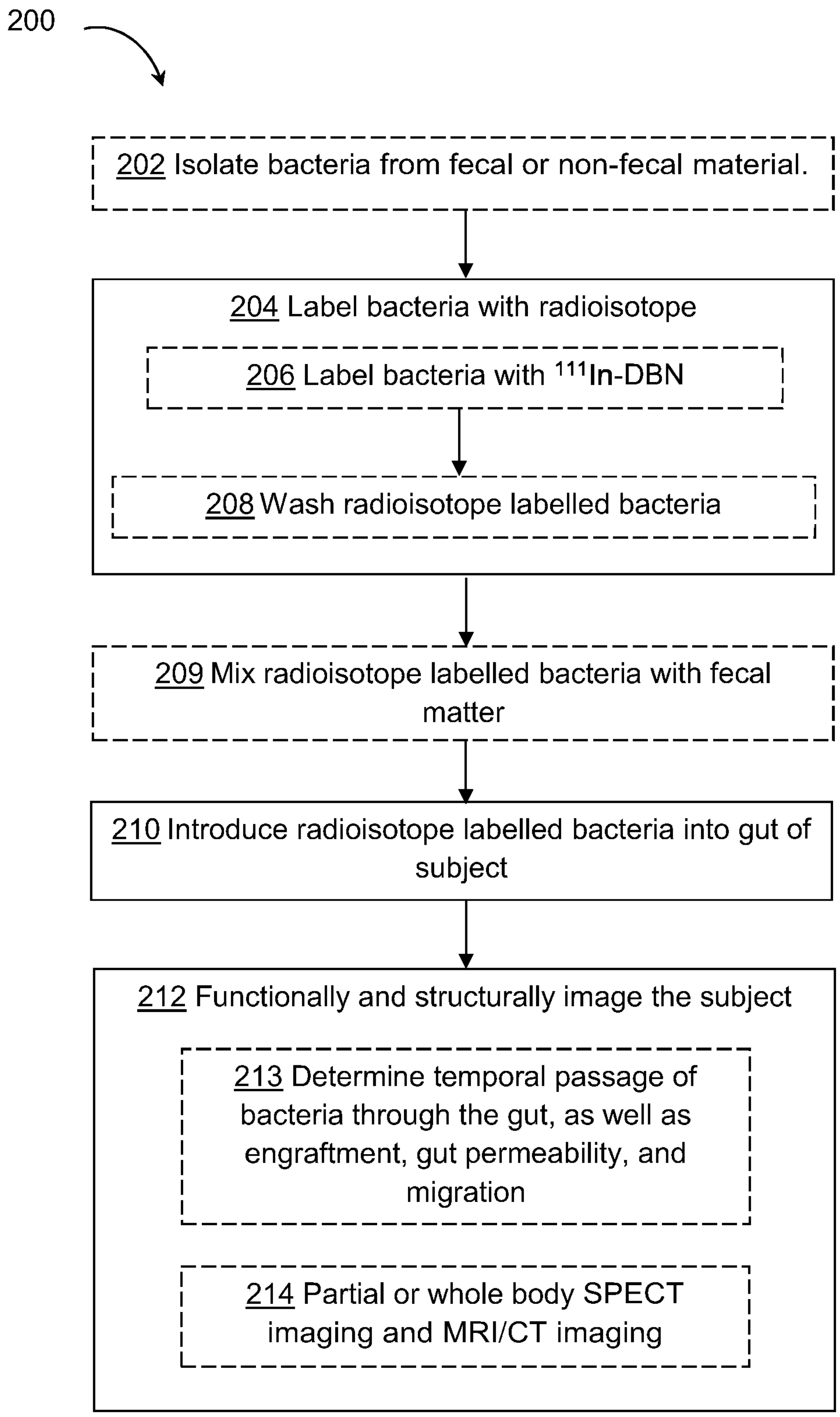
FIG. 2 is a flowchart setting forth the steps of another example method for imaging bacteria (for example, gut bacteria) in a subject.

FIG. 2 illustrates another exemplary method 200 for imaging microbiota, for example, gut bacteria, in a subject, and in particular, imaging of bacterial concentrations throughout the body of small animals, large animals, and humans using $^{111}$In as the radioisotope.

At 202, bacteria (such as gut bacteria) may be isolated from fecal or non-fecal material. For example, commercially-available bacteria may be utilized. One example of such bacteria is *Lactobacillus crispatus* ATCC33820.

At 204, the isolated bacteria are labelled with a radioisotope or nuclear medicine tracer. In one example embodiment, at 206, the *Lactobacillus crispatus* ATCC33820 bacteria is labelled with the radioisotope $^{111}$In chelated to dodecane-tetraacetic acid (DOTA) and covalently bound to cell surface protein through an N-hydroxysuccinimyl (NHS) linkage ($^{111}$In-DOTA-NHS) and imaged using SPECT. Other known metal based single photon emitting radioisotopes may alternatively be used.

The isolated bacteria are then combined with the $^{111}$In-DOTA-NHS and incubated. During their incubation, the $^{111}$In-labelled agent covalently binds to primary amines of cell surface proteins of the isolated bacteria, thus, randomly labelling the bacteria with the radioisotope.

The radioisotope labelled bacteria are then washed to remove unbound radiotracers at 208. Optionally, at 209, the washed radioisotope labelled bacteria may be mixed into recipient fecal material prior to its introduction into the subject.

At 210, the radioisotope labelled bacteria are introduced into the subject. The radiolabelled bacterial cells or fecal microbiota may be administered orally (for example, via capsules) or via nasogastric or naso-duodenal tube or via rectal enema or colonoscopy. In the case of vaginal microbiota transplantation (Lev-Sagie et al, 2019), radiolabelled bacteria may be transplanted into the vagina.

The subject is then imaged at 212. In this embodiment, radioisotope imaging may involve single-photon emission computed tomography (SPECT) imaging, rather than positron emission tomography (PET) imaging. Determining anatomical location of the radioactive image may involve magnetic resonance imaging (MRI) or X-ray computed tomography (CT) imaging. Radioisotope, MRI and/or CT imaging may take place simultaneously or sequentially, and method 200 may include one or more rounds of imaging. As well, both the gut and/or the surrounding regions around the gut of the subject may be imaged, or the entire subject may be imaged. Utilizing such imaging, in certain example embodiments, at 213 one is able to determine the temporal passage of bacteria through the gut, as well as engraftment, gut permeability, and/or migration. In certain example embodiments, at 214, the functional and structural imaging of the subject includes partial or whole body SPECT imaging and/or MRI/CT imaging.

For example, at 214, after the $^{111}$In-labelled gut bacteria or bacteriophage are transplanted or ingested, the subject may undergo SPECT or SPECT/MRI or SPECT/CT for 30 min every 2 hours for 12 hours. Subsequently, imaging may further be performed every 4 days until the $^{111}$In is no longer detectable. Combining radioisotope and anatomical imaging allows for the 3D MRI image and/or the 3D CT image to be segmented and used to segment the SPECT images. The X-ray CT and the MRI images will allow segmentation of the SPECT images to anatomical location. Correction for gut motility during or between imaging sessions may be useful or required.

In alternate applications, the subject may undergo SPECT/MRI imaging, or SPECT/CT imaging followed by MRI. The frequency and length of the imaging of the subject may also vary from 30 min every 2 hours for 12 hours, and may vary from subsequently being performed every 4 days. For example, imaging may be performed once per $^{111}$In physical (or biological) half-life, such as once every 2.8 days, until the $^{111}$In is no longer detectable.

While methods 100 and 200 have been described for using radiolabelled bacteria for imaging bacteria, other microorganisms may be used to indirectly image bacteria with the subject, including bacteriophages. Bacteriophage are viruses that infect and replicate within bacteria and archaea. They can be used to control/kill a disease causing pathogenic bacteria. Unlike many antibiotics, most bacteriophage are very specific to the bacteria host. The specificity can be used to identify the presence of a specific species of bacteria.

Figure 3:
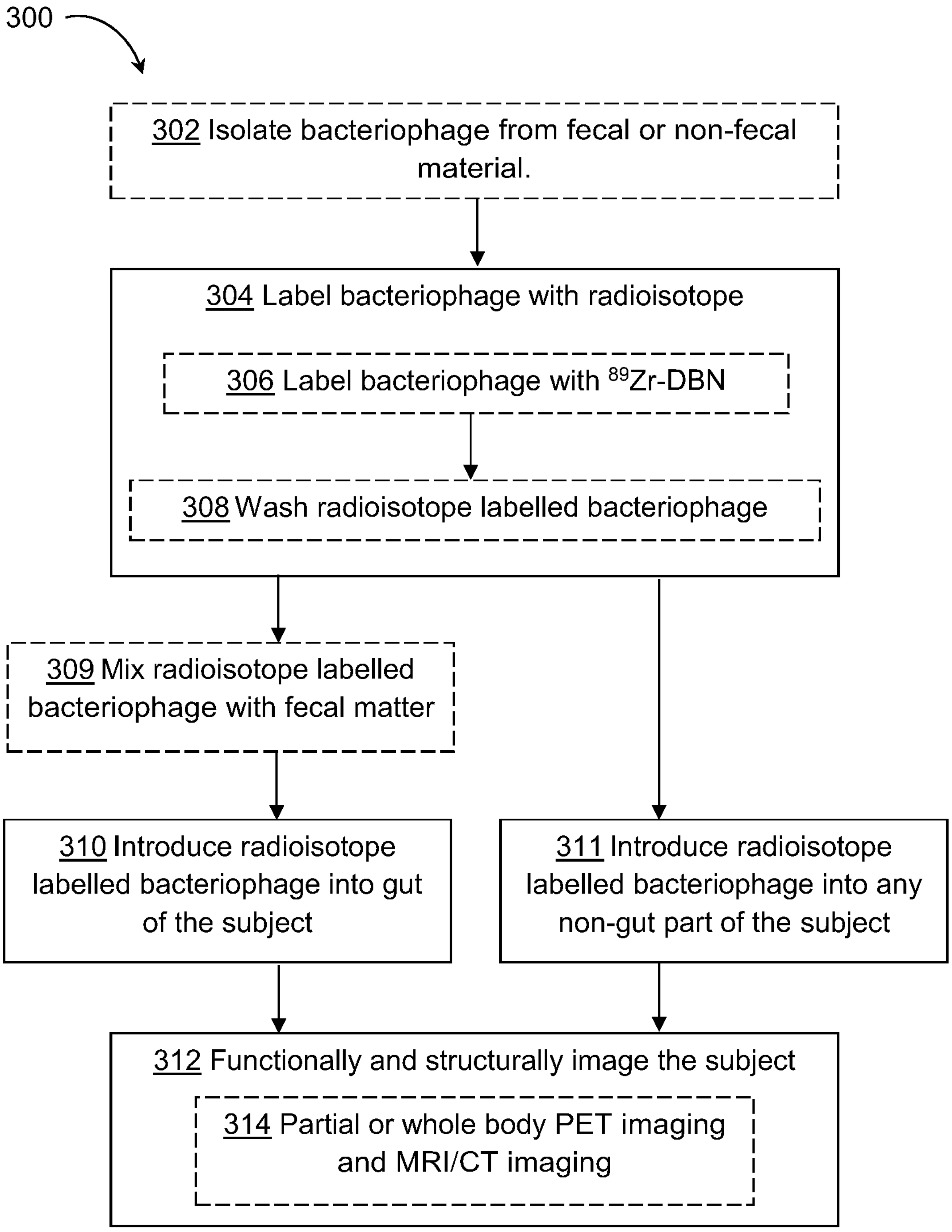
FIG. 3 is a flowchart setting forth the steps of an example method for imaging bacteriophage in a subject.

FIG. 3 illustrates another exemplary method 300 for imaging gut microbiota in a subject, and in particular, imaging of bacterial concentrations throughout the body of small animals, large animals, and humans using bacteriophage.

Optionally, as shown at 302, bacteriophage may be isolated from fecal material, and could include a bacteriophage that is specific to gut bacteria. More typically, however, bacteriophage is cultivated or purchased commercially. Bacteriophage may be selected based on their selectivity to a specific, desired form of bacteria meant to be imaged. Bacteriophage (such as genetically-engineered bacteriophage) may also be utilized and selected based on their life cycle. For example, a bacteriophage with a propensity for duplication within a host bacteria, but not lysis of the host bacteria, may be used for certain applications. Alternatively, a bacteriophage with a propensity for duplication and lysis of the host bacteria may be selected for other applications. Bacteriophage specific for infection of a very narrow selection of bacteria may be utilized in certain applications, whereas a bacteriophage with a wider range of infection may be utilized, depending on the goals of the imaging and/or study.

One example of such bacteriophage is a bacteriophage that is specific to gut bacteria. Of course, alternatively, and often preferably, bacteriophage may instead be isolated from other sources, or commercially available. Bacteriophage may be selected for their specificity to bacteria of interest.

Examples of bacteriophage include, but are not limited to, *Escherichia coli* bacteriophages LH01-Myoviridae, LL5-Siphoviridae, T4D-Myoviridae, and LL12-Myoviridae. Bacteriophages are ubiquitous viruses, found wherever bacteria exist. It is estimated there are more than $10^{31}$ bacteriophages on the planet, more than every other organism on Earth, including bacteria, combined.

At 304, the isolated bacteriophage are labelled with a radioisotope, for example a nuclear medicine radio-tracer used in PET or SPECT. In one example embodiment, at 306, the bacteriophage are labelled with $^{89}$Zr-DBN as described above in method 100. Alternately, the bacteriophage are labelled with $^{111}$In-DOTA-NHS as described above in method 200.

The radioisotope labelled bacteriophage are then washed/purified to remove unbound radiotracers at 308. Optionally, at 309, the washed radioisotope labelled bacteriophage may be mixed into recipient fecal material prior to its introduction into the subject.

At 310, the radioisotope labelled bacteriophage are introduced into the gut of the subject. The radiolabelled bacteriophage or fecal microbiota may be administered orally (for example, via capsules) or via nasogastric or naso-duodenal tube or via rectal enema or colonoscopy. Alternately, at 311, if not mixed with fecal matter, the labelled bacteriophage can be administered intravenously, intraarterially, intrathecally, intramuscularly, intradermally, subcutaneously or intra-cavitarily. Due to the nature of the bacteriophage, the radiolabelled phages will naturally, with time, infect, and therefore co-locate with, and replicate within, its specified host bacteria within the subject.

As noted above, in mammalian cells, radioactivity as high as 0.5 Bq/cell has been shown to be safe. Since bacteria are much smaller than mammalian cells, approximately 100 times smaller in terms of surface area, the target radioactivity level per bacterial cell may be reduced to approximately 0.005 Bq/cell. Since bacteriophage are smaller than bacterial cells (20 to 200 nm vs 400 nm and up, respectively), the target radioactivity level per bacteriophage should scale primarily linearly with surface area. However, even small bacteriophage (e.g. about 20 nm) can be labelled sufficiently as large quantities would be used even though Bq/bacteriophage would be labelled at approximately $1\times10^{-4}$.

The subject is then imaged at 312. Imaging may involve positron emission tomography (PET) imaging, and magnetic resonance imaging (MRI) or X-ray computed tomography (CT) imaging. Imaging with PET, MRI and CT may take place simultaneously (see FIG. 5) or sequentially, and method 300 may include one or more rounds of imaging. As well, the gut and/or the surrounding regions around the gut and/or the entire subject may be imaged. In certain example embodiments, at 314, the functional and structural imaging of the subject or portion thereof includes partial or whole body PET imaging and/or MRI/CT imaging.

For example, if $^{89}$Zr-DBN labelled bacteriophage specific for a bacteria was ingested, if the bacteria are present in the gut, the PET signal from the bacteriophage can be interpreted to indicate the location and presence of the gut bacteria. In another embodiment, if the labelled bacteriophage was deposited in the body intravenously, the PET signal from the bacteriophage can be interpreted to indicate the presence and location of the bacteria in a tissue or fluid in the body.

In alternate applications, for example using $^{111}$In-DOTA-NHS, the subject may undergo SPECT/MRI imaging, or SPECT/CT imaging followed by MRI. The frequency and length of the imaging of the subject may also vary from 30 min every 2 hours for 12 hours, and may vary from subsequently being performed every 4 days. For example, imaging may be performed once per $^{89}$Zr physical (or biological) half-life.

Figure 4:
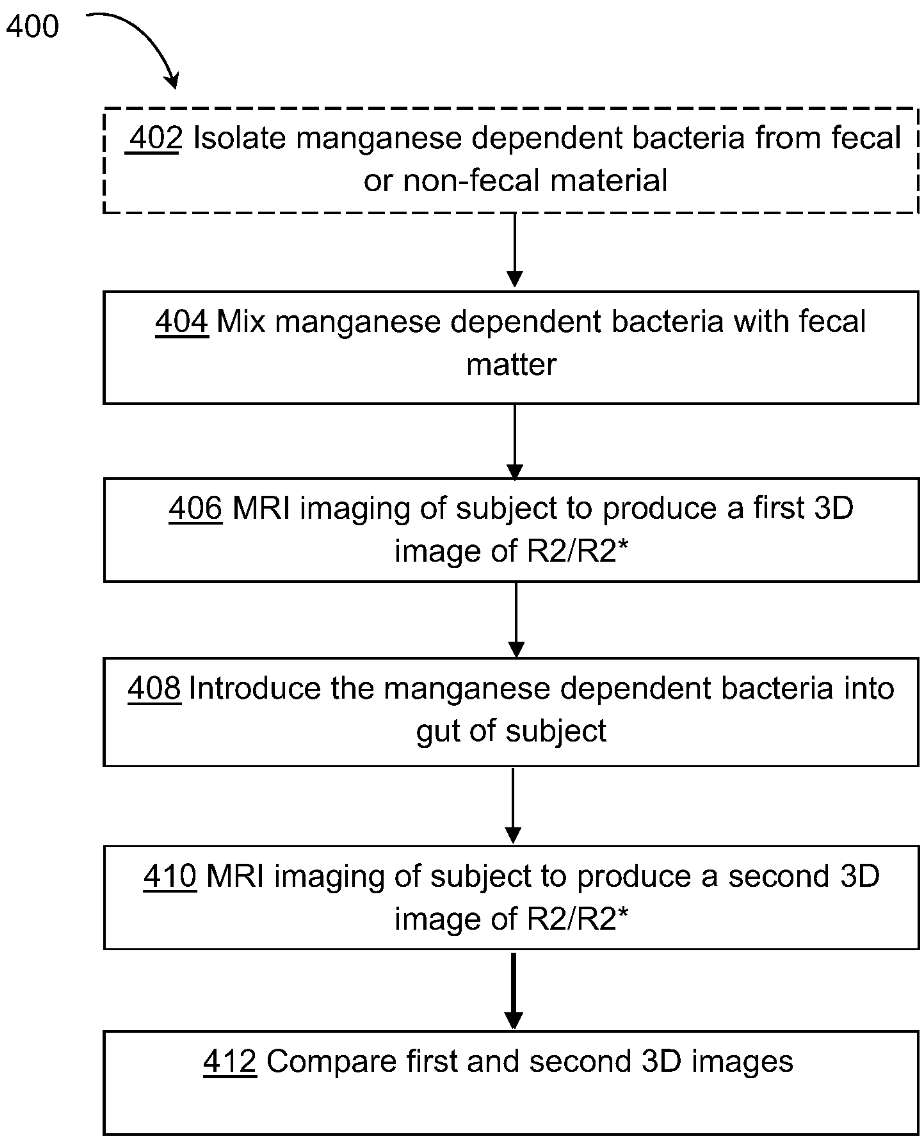
FIG. 4 is a flowchart setting forth the steps of an example method for imaging manganese dependent bacteria in a subject.

FIG. 4 shows an alternate embodiment—a method for imaging manganese dependent bacteria in a subject.

At 402, manganese-dependent bacteria may be isolated from fecal or non fecal material. For example, such bacteria may be gut bacteria, or may be commercially available bacteria, such as a probiotic supplement.

Unlike examples 100-300, the isolated bacteria are not labelled with a radioisotope or nuclear medicine tracer. Instead, their manganese levels are utilized for imaging.

At 404, the manganese dependent bacteria is mixed into recipient fecal material prior to its introduction into a subject, in an administration of the known microbial therapy referred to as fecal microbiota transplantation (FMT). This may allow imaging of FMT bacteria, helping determining the effectiveness of the transplantation, for example.

At 406, an MRI of the subject is performed, to produce a first 3D image of R2/R2*, before the manganese dependent bacteria are introduced into the gut of the subject. Then, at 408, the fecal matter with manganese dependent bacteria are introduced into the subject. In some applications, the bacterial cells or fecal microbiota are transplanted into the duodenum of the subject using a feeding tube. The manganese dependent bacteria may be the bacteria in probiotic products or fermented food which is consumed. In other applications, the bacterial cells are simply swallowed, or otherwise ingested, by the subject.

The subject is then imaged again at 410, to produce a second 3D image of R2/R2*.

The two images are compared at 412, and differences in imaging correspond to the location of the manganese dependent bacteria which was introduced into the subject.

Figure 5:
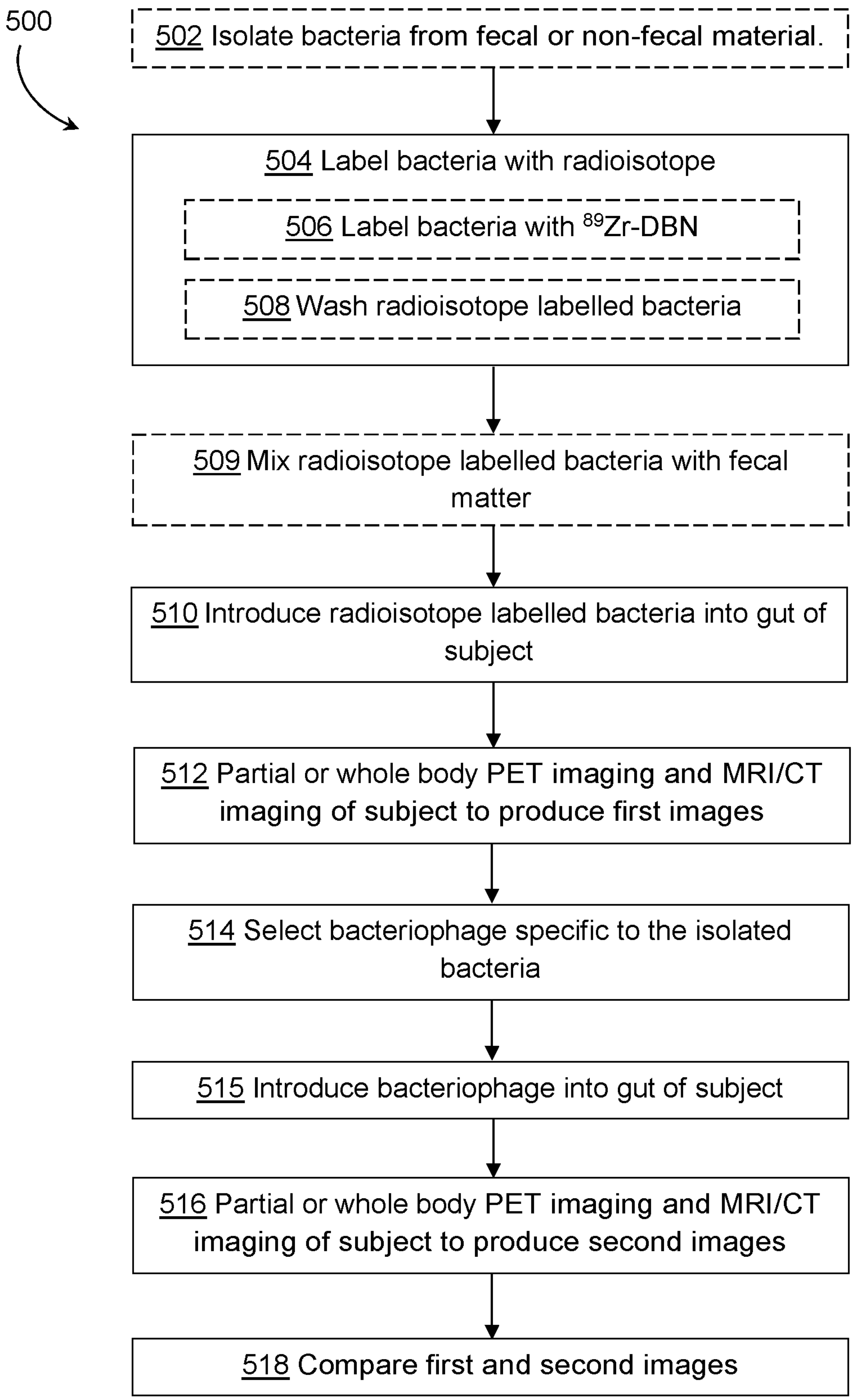
FIG. 5 is a flowchart setting forth the steps of an example method for imaging bacteriophage-specific bacteria in a subject.

Another comparative imaging method is shown in FIG. 5 and example method 500.

At 502, bacteria may be isolated from fecal or non fecal material. For example, such bacteria may be gut bacteria, or may be commercially available bacteria, such as a probiotic supplement. One example of such gut bacteria is *Lactobacillus crispatus*, such as strain ATCC33820. As understood, other strains of aerobic and anaerobic bacteria may be used. Though isolation from fecal material is shown, this methodology could equally be applied to bacterial strains from other sources that can be isolated and labelled, such as those used for probiotic, food, animal or environmental purposes.

Examples of bacterial species include other members of the genera, *Lactobacillus, Bifidobacteria, Prevotella, Bacteroides, Clostridium, Akkermansia, Ruminococcus, Enterococcus, Streptococcus, Escherichia*, Lachnospiraceae, *Blautia, Fusobacterium, Dorea, Roseburia* and *Faecalibacterium*. For example, examples of gut bacteria useful for labelling in the present method include *L. crispatus* (such as *L. crispatus* ATCC33820), *E. coli* (such as *E. coli* BL21(DE3), *E. coli* MG1655, *E. coli* Nissle, *E. coli* 25922, *E. coli* 67, *E. coli* AD110, *E. coli* GR-12, *E. coli* 536, *E. coli* J96), *E. faecalis* (such as *E. faecalis* ATCC33186), *K. pneumoniae* (such as *K. pneumoniae* 280), *P. mirabilis* (such as *P. mirabilis* 296), *P. aeruginosa* (such as *P. aeruginosa* PA01), *S. aureus* (such as *S. aureus* Neuman and *S. aureus* USA300), *S. epidermidis* (such as *S. epidermidis* ATCC35984), *L. gasseri* (such as *L. gasseri* ATCC33323), *L. reuteri* (such as *L. reuteri* RC14), *L. rhamnosus* (such as *L. rhamnosus* GR-1), At 504, the isolated bacteria are labelled with a radioisotope or nuclear medicine tracer. In one example embodiment, at 506, the bacteria may be labelled with the radioisotope $^{89}$Zr, using labelling agent $^{89}$Zr-desferrioxamine-NCS ($^{89}$Zr-DBN) by adapting a published procedure (Bansal et al., 2015).

The radioisotope, such as $^{89}$Zr, is first isolated in a solution, such as a zirconium hydrogen phosphate solution, $^{89}Zr(HPO_4)_2$. The radioisotope is then chelated to form a labelling agent, such as $^{89}$Zr-DBN using DFO-Bz-NCS. $^{89}$Zr-DBN is a first generation prototypic labelling agent. Chelation of $^{89}$Zr to DBN has been adapted from Bansal et al. The DFO moiety is the chelating end of DBN. The isothiocyanato-benzyl group is the conjugating moiety that covalently binds primary amines on protein found at the cell surface. Desferrioxamine (DFO), or an improved chelator (Bhatt et al., 2018; Berg et al., 2020), may then be used as the chelating agent for the zirconium atom. DFO is conjugated to a p-isothiocyanato-benzyl group or an improved conjugating agent (Berg et al., 2020) to achieve the resulting $^{89}$Zr-desferrioxamine-NCS, or $^{89}$Zr-DBN.

Alternately, rather than producing $^{89}$Zr-DBN or its precursor $^{89}Zr(HPO_4)_2$, these may simply be purchased from a third party, including select cyclotron and radiochemistry facilities, where they are readily commercially available.

The isolated bacteria are then combined with the $^{89}$Zr labelling agent (for example, $^{89}$Zr-DBN) and incubated. During incubation, the $^{89}$Zr-DFO-labelled agent covalently binds to primary amines of cell surface proteins of the isolated bacteria (or bacteriophage), thus, randomly labelling the external cell surface of the bacteria with the radioisotope.

The radioisotope labelled bacteria are then separated from unbound $^{89}$Zr at 508. For example, the sample may be "washed" by centrifuging to remove unbound radiotracer remaining in the supernatant from the radiolabelled bacterial pellet.

In mammalian cells, radioactivity as high as 0.5 Bq/cell has been shown to be safe. Since bacteria are much smaller than mammalian cells, approximately 100 times smaller in terms of surface area, the target radioactivity level per bacterial cell may be reduced to approximately 0.005 Bq/cell.

Optionally, at 509, the washed radioisotope-labelled bacteria may be mixed into recipient fecal material prior to its introduction into a subject, in an administration of the known microbial therapy referred to as fecal microbiota transplantation (FMT). This may allow imaging of FMT bacteria, helping determining the effectiveness of the transplantation, for example.

At 510, the radioisotope labelled bacteria are introduced into the subject. In some applications, the radiolabelled bacterial cells or fecal microbiota are transplanted into the duodenum of the subject using a feeding tube. The radiolabelled bacterial cells may be the bacteria in probiotic products or fermented food which is consumed. In other applications, the radiolabelled bacterial cells are simply swallowed, or otherwise ingested, by the subject.

While method 500 has been described with $^{89}$Zr as the radioisotope, other metal-based positron radioisotopes may alternately be used, like for example $^{52}$Mn (with a 5.5 day half-life). As well, single photon radioisotopes, for example $^{111}$In (2.8 day half-life) may be used. In addition, heavy metal radioisotopes, such as $^{177}$Lu (a beta emitter and single photon emitter, 6.6 day half-life) and $^{225}$Ac (an alpha emitter and single photon emitter, 10 day half-life) can be used to label the bacteria.

In an alternate embodiment (not shown), instead of isolating and labelling the bacteria with a radioisotope, a bacteria-specific imaging approach such as labelling with 2-Deoxy-2[$^{18}$F]fluoro-D-sorbitol ($^{18}$F-FDS) can be utilized as described in Ordonez (2021). $^{18}$F-FDS has been found to accumulate in Enterobacterales but not in healthy mammalian or cancer cells and $^{18}$F-FDS PET has been found to specifically detect Enterobacterales infections in murine models (Ordonez (2021)). Accordingly, 18F-FDS can be administered systemically to the subject and will specifically label bacteria.

The subject is then imaged at 512. Imaging may involve positron emission tomography (PET) imaging, and magnetic resonance imaging (MRI) or X-ray computed tomography (CT) imaging. Imaging with PET, MRI and CT may take place simultaneously (see FIG. 11) or sequentially, and method 500 may include one or more rounds of imaging. As well, both the gut and/or the surrounding regions around the gut of the subject may be imaged. In certain example embodiments, at one is able to determine the temporal passage of bacteria through the gut, as well as engraftment, gut permeability, and/or migration. In certain example embodiments, the functional and structural imaging of the subject includes partial or whole body SPECT imaging and/or MRI/CT imaging.

At 512, after the radioisotope labelled bacteria are transplanted or ingested, the subject may undergo PET/MRI for 30 min every 2 hours for 12 hours. Subsequently, imaging may further be performed every 4 days until the $^{89}$Zr is no longer detectable. Repetitive imaging may be performed up to approximately 4 weeks, depending on the gut motility associated with the individual subject, the persistence of bacteria in the body, and the half-life of the radioisotope. Combining MRI and/or CT with radionuclide imaging allows the segmented 3D MRI or CT image to be used to segment the PET images. For proper segmentation of the PET image by the MRI or CT image it is preferable that gut mobility is negligible between the PET and MRI/CT data acquisition. In animal studies, anesthesia will eliminate most gut mobility whereas in humans gut mobility is typically eliminated using drugs like hyoscine butylbromide during MRI examination.

In alternate applications, the subject may undergo PET/MRI imaging, or PET/CT imaging followed by MRI. The frequency and length of the imaging of the subject may also vary from 30 min every 2 hours for 12 hours, and may vary from subsequently being performed every 4 days until the $^{89}$Zr is no longer detectable. For example, imaging may be performed once per radioisotope physical (or biological) half-life, such as once every 3.3 days for $^{89}$Zr, until the $^{89}$Zr is no longer detectable.

Labelling bacteria with, for example, $^{89}$Zr-DBN followed by PET/MRI imaging allows determination of engraftment in the gut of the introduced bacteria, permeability of the bacteria out of the gut followed by migration of the bacteria to different locations in the body.

Following this first imaging, at 514, bacteriophage are selected, specific to the isolated bacteria that was previously introduced into the gut of the subject. Bacteriophage are isolated and selected based on their specificity to the isolated bacteria previously introduced into the gut of the subject. They are also selected based on their ability to lyse and kill said bacteria.

At 515, the bacteriophage are introduced into the gut of the subject. The bacteriophage may be administered orally (for example, via capsules) or via nasogastric or naso-duodenal tube or via rectal enema or colonoscopy. Alternately, the bacteriophage can be administered intravenously, intraarterially, intrathecally, intramuscularly, intradermally, subcutaneously or intra-cavitarily. Due to the nature of the bacteriophage, the phages will naturally, with time, infect, replicate in, and lyse, the specified bacteria within the subject. Upon lysing of the specified bacteria, the bacteria will release the radioisotope, which will then be either loosely dispersed within the organism, or eliminated from the organism, since the bacteria will no longer contain it.

The subject is then imaged again at 516. The imaging should be similar in methodology to the imaging used in 512.

The two images are compared, and differences in images can then be directly attributable to the presence of the bacteria in question.

Figure 6:
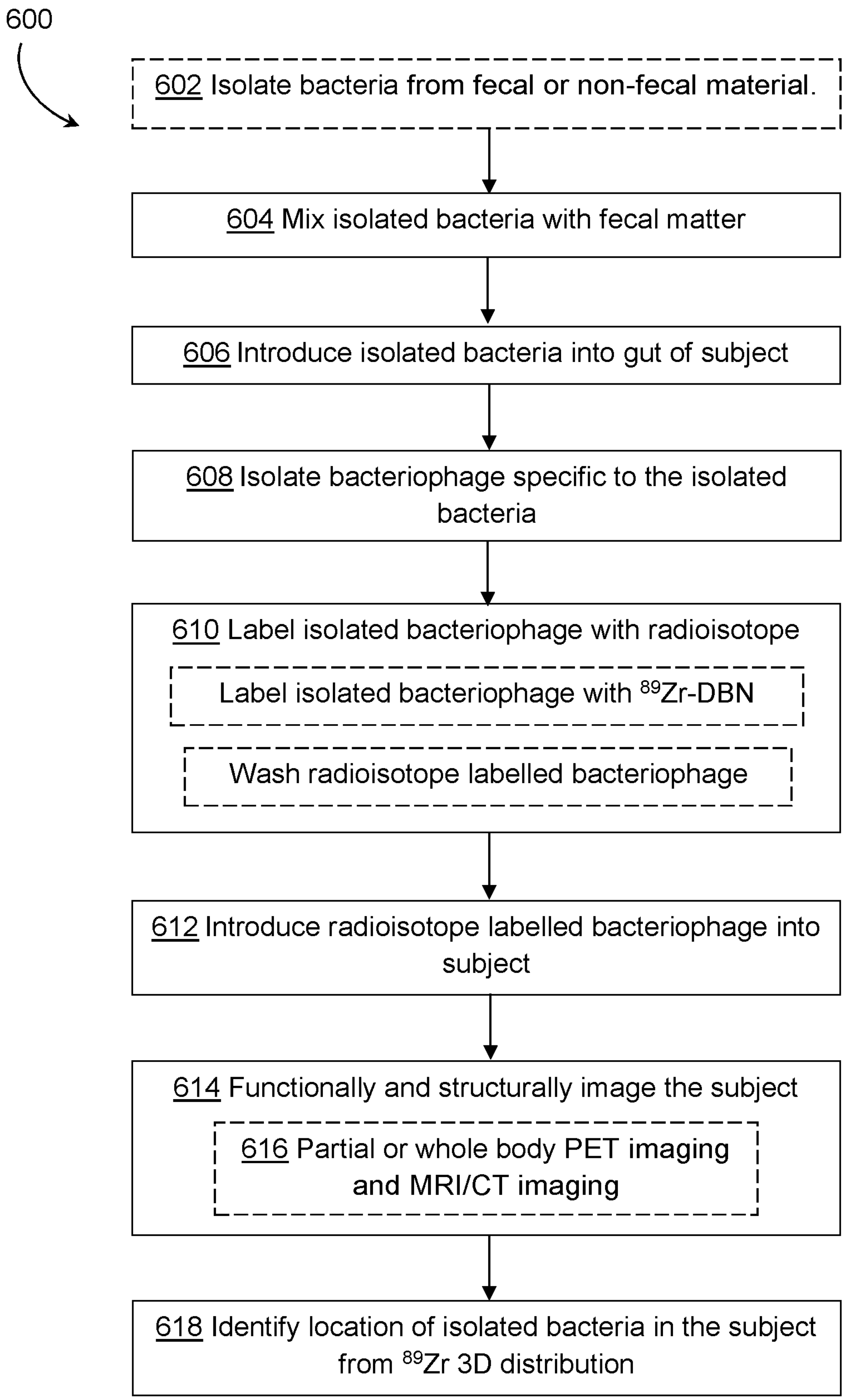
FIG. 6 is a flowchart setting forth the steps of an example method for imaging bacteriophage-specific bacteria in a subject.

A further example method is found in FIG. 6. Here, bacteria is introduced, then radiolabelled bacteriophage specific to the bacteria are introduced and imaged.

At 602, bacteria may be isolated from fecal or non fecal material. For example, such bacteria may be gut bacteria, or may be commercially available bacteria, such as a probiotic supplement. One example of such gut bacteria is *Lactobacillus crispatus*, such as strain ATCC33820. As understood, other strains of aerobic and anaerobic bacteria may be used. Though isolation from fecal material is shown, this methodology could equally be applied to bacterial strains from other sources that can be isolated and labelled, such as those used for probiotic, food, animal or environmental purposes.

Examples of bacterial species include other members of the genera, *Lactobacillus, Bifidobacteria, Prevotella, Bacteroides, Clostridium, Akkermansia, Ruminococcus, Enterococcus, Streptococcus, Escherichia*, Lachnospiracae, *Blautia, Fusobacterium, Dorea, Roseburia* and *Faecalibacterium*. For example, examples of gut bacteria useful for labelling in the present method include *L. crispatus* (such as *L. crispatus* ATCC33820), *E. coli* (such as *E. coli* BL21(DE3), *E. coli* MG1655, *E. coli* Nissle, *E. coli* 25922, *E. coli* 67, *E. coli* AD110, *E. coli* GR-12, *E. coli* 536, *E. coli* J96), *E. faecalis* (such as *E. faecalis* ATCC33186), *K. pneumoniae* (such as *K. pneumoniae* 280), *P. mirabilis* (such as *P. mirabilis* 296), *P. aeruginosa* (such as *P. aeruginosa* PA01), *S. aureus* (such as *S. aureus* Neuman and *S. aureus* USA300), *S. epidermidis* (such as *S. epidermidis* ATCC35984), *L. gasseri* (such as *L. gasseri* ATCC33323), *L. reuteri* (such as *L. reuteri* RC14), *L. rhamnosus* (such as *L. rhamnosus* GR-1), At 604, the bacteria is mixed with fecal matter and introduced into the gut of the subject at 606. In some applications, the bacterial cells or fecal microbiota are transplanted into the duodenum of the subject using a feeding tube. The bacterial cells may be the bacteria in probiotic products or fermented food which is consumed. In other applications, the bacterial cells are simply swallowed, or otherwise ingested, by the subject.

Following the administration of the bacteria is administration of a radioisotope labelled bacteriophage into the subject.

At 608, bacteriophage specific to the isolated bacteria are isolated. These may be isolated from fecal material. More typically, however, bacteriophage is cultivated or purchased commercially. Bacteriophage are selected based on their selectivity to the bacteria introduced into the gut of the subject at 606. Bacteriophage (such as genetically-engineered bacteriophage) may also be utilized and selected based on their life cycle. For example, a bacteriophage with a propensity for duplication within a host bacteria, but not lysis of the host bacteria, may be used.

At 610, the isolated bacteriophage are labelled with a radioisotope or nuclear medicine tracer. In one example embodiment, the bacteriophage are labelled with $^{89}$Zr-DBN as described above in method 100. Alternately, the bacteriophage are labelled with $^{111}$In-DOTA-NHS as described above in method 200.

The radioisotope labelled bacteriophage are then washed to remove unbound radiotracers.

At 612, the radioisotope labelled bacteriophage are introduced into the gut of the subject. The radiolabelled bacteriophage or fecal microbiota may be administered orally (for example, via capsules) or via nasogastric or naso-duodenal tube or via rectal enema or colonoscopy. Alternately, the labelled bacteriophage can be administered intravenously, intraarterially, intrathecally, intramuscularly, intradermally, subcutaneously or intra-cavitarily. Due to the nature of the bacteriophage, the radiolabelled phages will naturally, with time, infect, and therefore co-locate with, and replicate in, its specified bacteria within the subject.

As noted above, in mammalian cells, radioactivity as high as 0.5 Bq/cell has been shown to be safe. Since bacteria are much smaller than mammalian cells, approximately 100 times smaller in terms of surface area, the target radioactivity level per bacterial cell may be reduced to approximately 0.005 Bq/cell. Since bacteriophage are smaller than bacterial cells (20 to 200 nm vs 400 nm and up, respectively), the target radioactivity level per bacteriophage should scale primarily linearly with surface area. However, even small bacteriophage (e.g. about 20 nm) can be labelled sufficiently as large numbers would be used even though Bq/bacteriophage would be approximately $1\times10^{-4}$.

The subject is then imaged at 614. Imaging may involve positron emission tomography (PET) imaging, and magnetic resonance imaging (MRI) or X-ray computed tomography (CT) imaging. Imaging with PET, MRI and CT may take place simultaneously or sequentially, and method 600 may include one or more rounds of imaging. As well, both the gut and/or the surrounding regions around the gut of the subject may be imaged. In certain example embodiments, at one is able to determine the temporal passage of bacteria through the gut, as well as engraftment, gut permeability, and/or migration. In certain example embodiments, the functional and structural imaging of the subject includes partial or whole body SPECT imaging and/or MRI/CT imaging (616).

At 614, after the radioisotope labelled bacteriophage are transplanted or ingested, the subject may undergo PET/MRI for 30 min every 2 hours for 12 hours. Subsequently, imaging may further be performed every 4 days until the $^{89}$Zr is no longer detectable. Repetitive imaging may be performed up to approximately 4 weeks, depending on the gut motility associated with the individual subject, the persistence of bacteria in the body, and the half-life of the radioisotope. Combining MRI and/or CT with radionuclide imaging allows the segmented 3D MRI or CT image to be used to segment the PET images. For proper segmentation of the PET image by the MRI or CT image it is preferable that gut mobility is negligible between the PET and MRI/CT data acquisition. In animal studies, anesthesia will eliminate most gut mobility whereas in humans gut mobility is typically eliminated using drugs like hyoscine butylbromide during MRI examination.

In alternate applications, the subject may undergo PET/MRI imaging, or PET/CT imaging followed by MRI. The frequency and length of the imaging of the subject may also vary from 30 min every 2 hours for 12 hours, and may vary from subsequently being performed every 4 days until the $^{89}$Zr is no longer detectable. For example, imaging may be performed once per radioisotope physical (or biological) half-life, such as once every 3.3 days for $^{89}$Zr, until the $^{89}$Zr is no longer detectable.

Labelling bacteriophage with, for example, $^{89}$Zr-DBN followed by PET/MRI imaging allows determination of engraftment in the gut of the introduced bacteria, permeability of the bacteria out of the gut followed by migration of the bacteria to different locations in the body.

While method 600 has been described with $^{89}$Zr as the radioisotope, other metal-based positron radioisotopes may alternately be used, like for example $^{52}$Mn (with a 5.5 day half-life). As well, single photon radioisotopes, for example $^{111}$In (2.8 day half-life) may be used. In addition, heavy metal radioisotopes, such as $^{177}$Lu (a beta emitter and single photon emitter, 6.6 day half-life) and $^{225}$Ac (an alpha emitter and single photon emitter, 10 day half-life) can be used to label the bacteriophage.

Following methods 100, 200, 300, 400, 500, or 600, the acquired images may be converted into quantitative images or maps of the number of labelled bacteria within the subject, as illustrated in method 700 of FIG. 7 and described below. Again, in FIG. 7, stippled rectangular boxes indicate optional (and possibly preferable) steps.

To convert the acquired images (optionally acquired at 702) into quantitative images or maps of the number of labelled bacteria within the subject, at 704, a biological sample may be collected from the subject. The biological sample can be one or more of a stool sample, a urine sample, a blood sample and a saliva sample. The radioactivity of the biological sample and the average number of radioisotope labels per bacterial cell or bacteriophage may then be determined at 706.

In cases when the gut of the subject is imaged, images of the gut may be segmented from the 3D MRI or CT images and then used to segment the PET gut images.

In such an embodiment, stool samples may be collected at intervals throughout the procedure. The activity per target bacteria (ATB) may be estimated from the stool samples using next generation sequencing (NGS) to identify bacterial strains. Additional information can be obtained using NMR relaxometry. If the proton (hydrogen atom) molecular exchange relaxation mechanisms can be manipulated to effectively create slow water exchange (Morariu & Benga, 1977), then this, combined with multi component relaxation measurements (Hazlewood et al., 1974 and Saab et al., 2001), can provide additional information about the sample composition/structure. For example, NMR relaxometry can be used to estimate the number of and kind of bacteria (Donnelly et al., 2019) in the stool sample. The absolute activity of $^{89}$Zr in the same stool sample may also be determined using calibrated radioactive counting detectors such as well counters or whole-body counters (FIG. 25) that can detect gamma rays and annihilation radiation. Thus, the activity per bacterium can be determined.

In addition to determining the specific activity per bacterium for the originally labelled strain, the determining of 706 may also include determining the extent of labelling on other strains of bacteria in the stool samples, and the extent of non-specific uptake in the non-bacterial fecal material.

Non-specific uptake (NSU) of $^{89}$Zr may be determined, for example, where the labelling of the entire fecal sample (fiber plus bacteria) is compared to the labelling of isolated bacteria extracted from the fecal sample (fiber removed). Even if some bacteria adhere to fiber, this would be considered as the fraction of labelled fecal material that remains in the intestine and is destined for excretion rather than migration outside the GI tract.

The number of target bacteria (TB) in the gut at the time of PET imaging can be calculated from the 3D PET activity distribution images (A) using the following Formula I:

$$TB(x, y, z, t) = \frac{A(x, y, z, t)(1 - NSU)}{ATB(t)}$$

Figure 10:
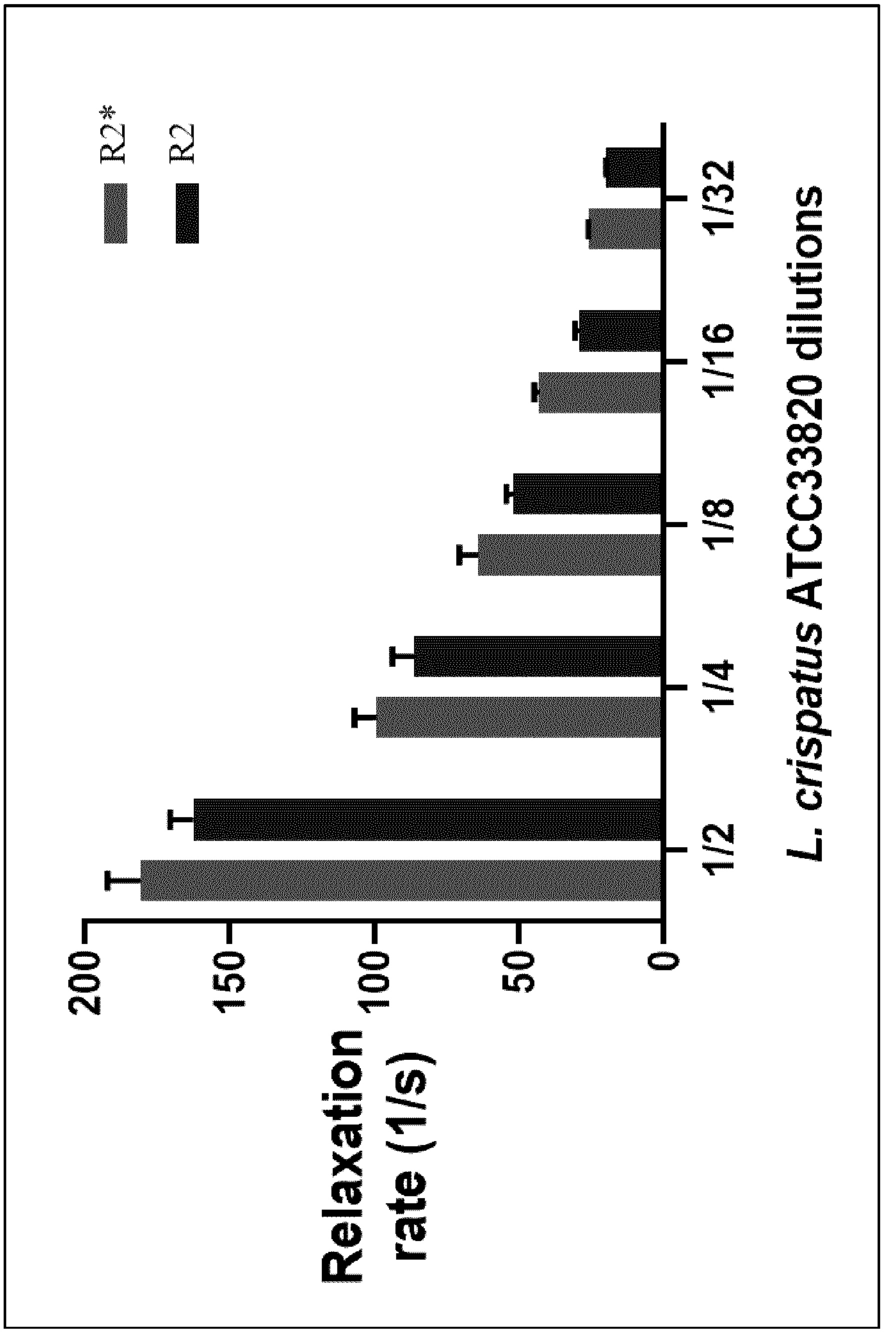
FIG. 10 shows R2 and R2* of *Lactobacillus crispatus* ATCC33820 after serial dilution in gelatin/PBS.
Figure 12:
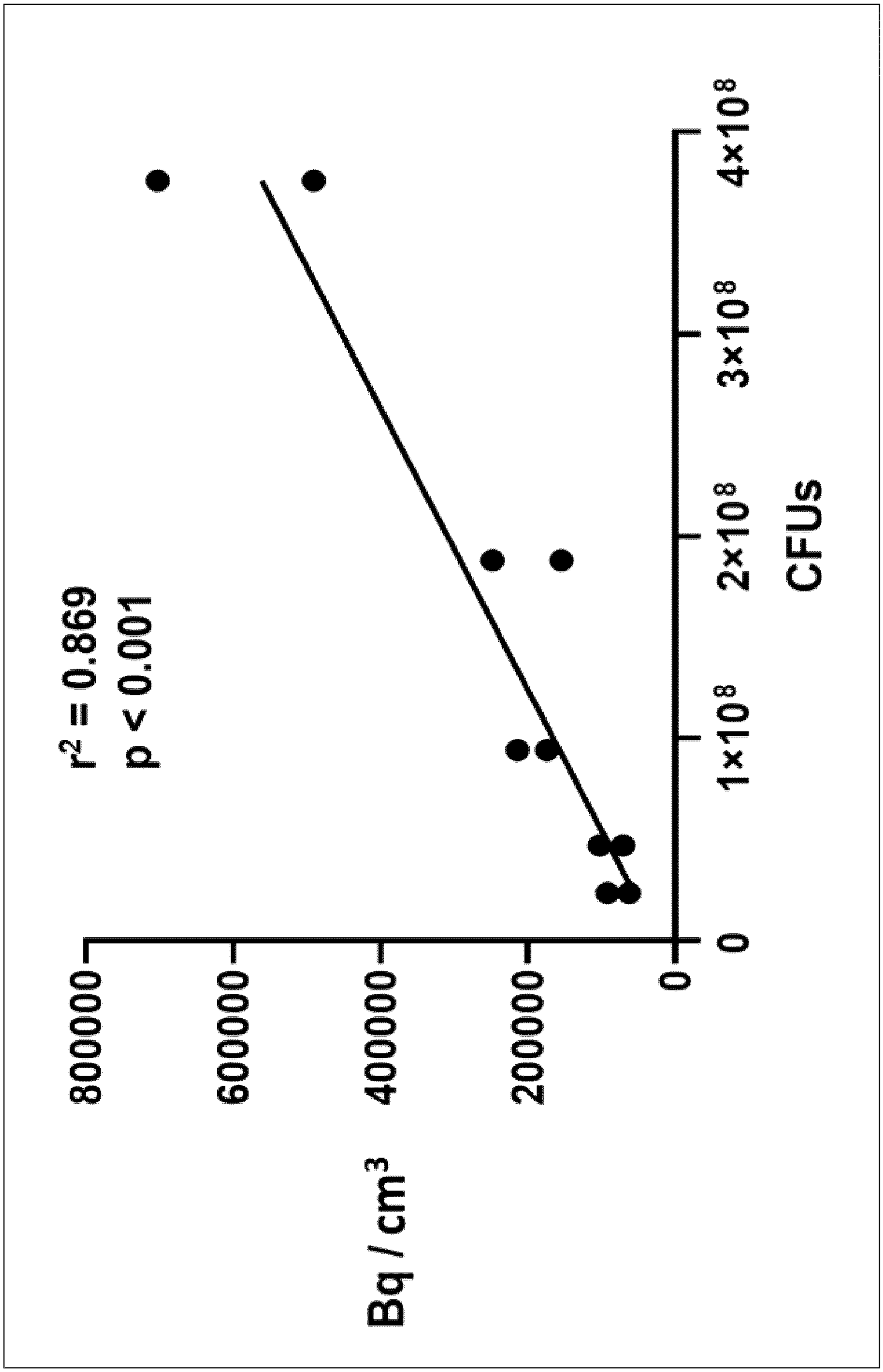
FIG. 12 illustrates the relationship between the number of cells detected by $^{89}$Zr-DBN labelling of bacteria (*Lactobacillus crispatus* ATCC33820) and the number of viable cells in the sample.

Where: TB (x,y,z,t) is the number of bacteria in the gut at location x,y,z at time t A (x,y,z,t) is the activity of $^{89}$Zr at location x,y,z at time t NSU is the activity in the stool sample not bound to bacteria per unit volume of stool and/or associated with fiber that is destined for excretion ATB (t) is the activity per bacterial cell not associated with fiber at time t At 708, having determined the number and location of radioisotope labelled gut microbiota in the gut of the subject, these calculations may be combined with the acquired PET and MRI images of the gut to generate 3D images of the number of bacteria per voxel in the gut. The principle behind this method is illustrated in FIGS. 10-12. In other words, both the PET and MRI images may be calibrated, for example using the information obtained from the stool samples, to generate quantitative 3D images of bacterial distribution or concentration throughout the gut in the subject's body.

In cases when one is measuring the extent of gut bacteria for permeability and migration outside the gut, the non-gut images may be further segmented to identify volumes to be investigated for the permeability and migration of the $^{89}$Zr labelled bacterium.

In such an embodiment, stool samples, blood samples, urine samples and/or saliva samples can be collected after each PET imaging, and at other times. The radioactivity per target bacterium and the non-specific uptake per volume of sample can be determined from the stool, blood, urine and/or saliva samples as described above. The number of target bacteria (TB) in the gut at the time of imaging may then be calculated according to Formula I.

The number of bacteria that have permeated the gut (TBP) at time t can be calculated using the following Formula II:

$$TBP(t) = \sum_{x,y,z} TBP(x, y, z, t)$$

Where:

$$TBP(x, y, z, t) = \frac{AP(x, y, z, t)(1 - NSUE)}{ATBE(t)}$$

Where: TBP (x,y,z,t) is the number of bacteria external to the gut at location x,y,z and at time t AP (x,y,z,t) is the activity of $^{89}Zr$ at location x,y,z at time t ATBE (t) is the activity per bacterium that have permeated the gut NSUE is the activity external to the gut that is not bound to bacteria and may be estimated from blood, saliva or urine samples The number of bacteria that have migrated to remote tissue (TBR) can be calculated using the following Formula III:

$$TBR(t) = \sum_{x,y,z} TBR(x, y, z, t)$$

Where TBR (x,y,z,t) is the number of bacteria at remote locations and the sum is carried over the volume of interest Note that $$TBR(x, y, z, t) = \frac{AR(x, y, z, t)(1 - NSUE)}{ABRE(t)}$$

Where ABR (t) is the radioactivity per bacterium determined from blood samples for all body locations except for the bladder and salivary glands. The radioactivity of the bladder is determined from the urine sample. The radioactivity of the salivary glands is determined from the saliva.

AR (x,y,z,t) is the activity of $^{89}Zr$ at location x,y,z at time t within the region of interest.

Having determined the number and location of radioisotope labelled gut microbiota in the region of interest external to the gut, these calculations may be combined with the acquired PET and MRI images of the region of interest outside the gut to generate 3D images of the number of bacteria per voxel in the region of interest. In other words, both the PET and MRI images may be calibrated, for example using the information obtained from the biological samples, to generate quantitative 3D images of bacterial distribution or concentration throughout the region of interest in the subject's body.

While 3D mapping of bacteria distribution is discussed herein, method 700 may be used to quantitatively 3D image other microbiota as well, such as viruses, bacteriophages or other microorganisms.

Figure 8:
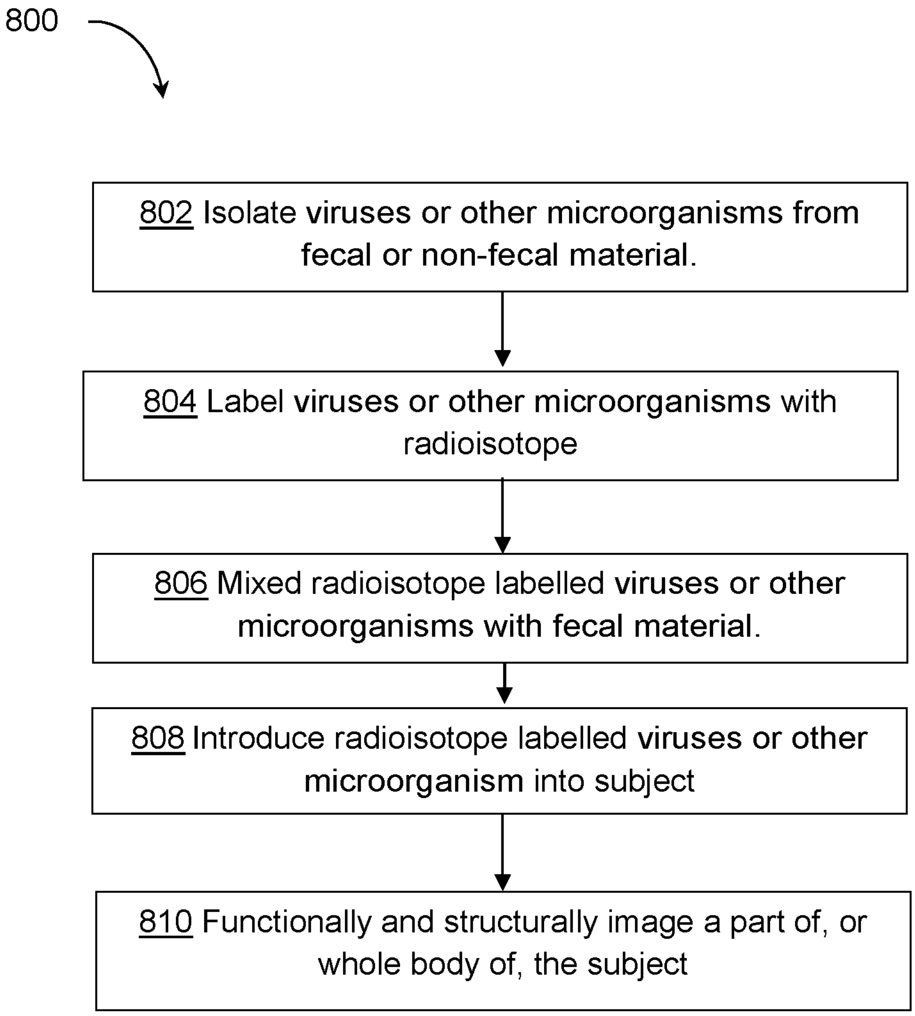
FIG. 8 is a flowchart setting forth the steps of an example method for imaging microbiota in a subject using fecal matter.

While methods 100, 200, 300, 400, 500 and 600 are described for imaging bacteria and bacteriophages in a subject, other microbiota such as viruses can also be imaged using the method shown in method 800 of FIG. 8. At 802, gut viruses or other gut microorganisms may be isolated from fecal material from the subject. At 804, the gut viruses or other gut microorganisms may be labelled with a radioisotope as described above. At 506, the radioisotope labelled gut viruses or other gut microorganisms may be mixed with the subject's fecal material and introduced back into the subject at 808. Then the subject may be functionally and/or structurally imaged as described above.

The following examples are provided to illustrate non-limiting embodiments of the above-described methods.

Example 1: Imaging Bacteria In Vitro Utilizing $^{89}Zr$ Labelling

This example demonstrates how bacteria are labelled with $^{89}Zr$ (3.3-day half-life) in vitro for bacterial detection, effects on bacterial viability, and label stability.

Radiolabelling bacteria with $^{89}Zr$: Bacteria were cultured overnight in their preferred medium. Then the bacteria were centrifuged and washed with PBS to remove medium components (e.g. protein). Bacteria was subsequently incubated with $^{89}Zr$-DBN at room temperature for 1 h with shaking. Bacterial radiolabelling was designed to achieve approximately 0.005 Bq/cell (identified as a colony forming unit, CFU). Excess label was removed through centrifugation and washing until the cell-free supernatant contains insignificant amounts of radioactivity.

Figure 9:
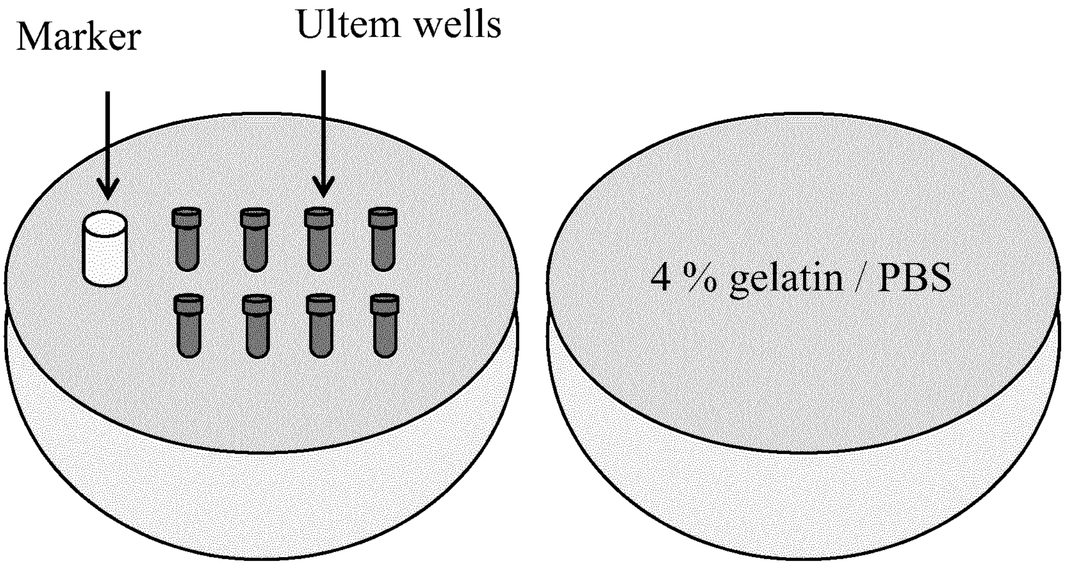
FIG. 9 depicts, in schematic form, an MRI gelatin phantom.

In vitro PET/MRI of $^{89}Zr$-labelled bacteria: Samples were prepared from cultured radiolabelled bacteria, mounted in a gelatin phantom and imaged using simultaneous PET/MR at 3 T. $^{89}Zr$-labelled cells were serially diluted in gelatin/PBS, loaded into Ultem wells and then mounted in a spherical gelatin phantom (9 cm diameter). FIG. 9 illustrates an MRI cell phantom. Cells were loaded into Ultem wells by centrifugation at 4500×g and then mounted in the gelatin phantom.

FIG. 10 illustrates R2 and R2* of *L. crispatus* ATCC33820 after serial dilution in gelatin/PBS. *Lactobacillus* crispatus displayed high transverse relaxation rates after dilution in gelatin/PBS. FIG. 10 shows the mean+/−SEM. Given that there was only one identifiable R2* and R2, the bacterial cells were determined to be in fast exchange with the gelatin/PBS. The total transverse relaxivity, R2* (in red) consists predominantly of the irreversible, R2 component (in blue).

Figure 13:
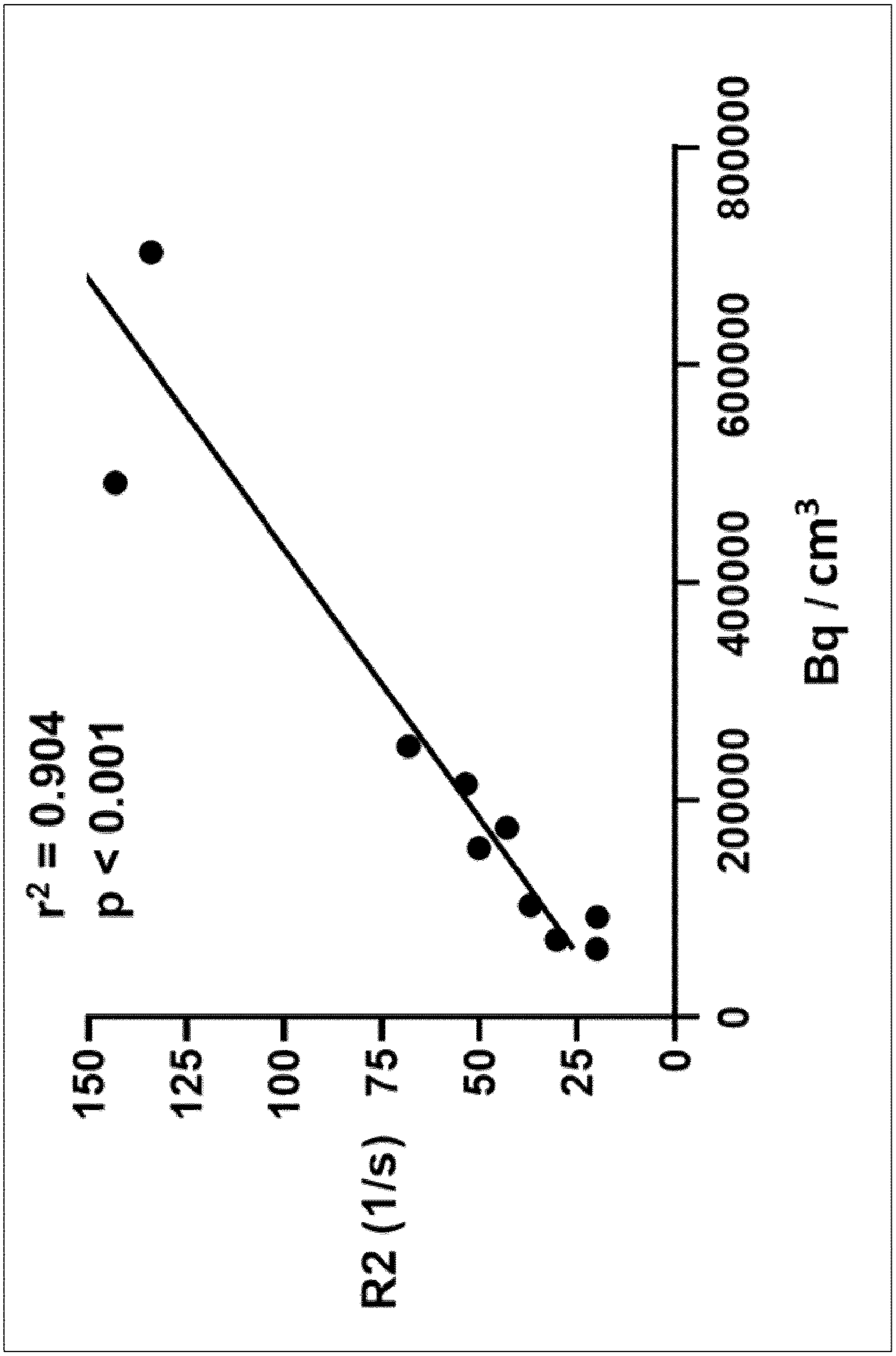
FIG. 13 illustrates that R2 and $^{89}$Zr activity are strongly correlated in *L. crispatus* ATCC33820.

FIGS. 11 and 12 illustrate the relationship between the number of cells detected by $^{89}Zr$-DBN labelling of bacteria (*Lactobacillus crispatus* ATCC33820) and the number of viable cells seeded. In FIG. 12, $^{89}Zr$ is shown in absolute units of disintegrations per second and the number of viable cells corresponds to colony forming units (CFU). The initial number of $^{89}Zr$ labels per cell can be used as a calibration factor. After ingestion of radiolabelled bacteria, proliferation in the gut and loss due to bacterial death, a modified calibration factor could be determined from analysis of the excreted stool. As expected, FIG. 13 illustrates that R2 and $^{89}Zr$ activity are strongly correlated in *L. crispatus.*

Figure 14:
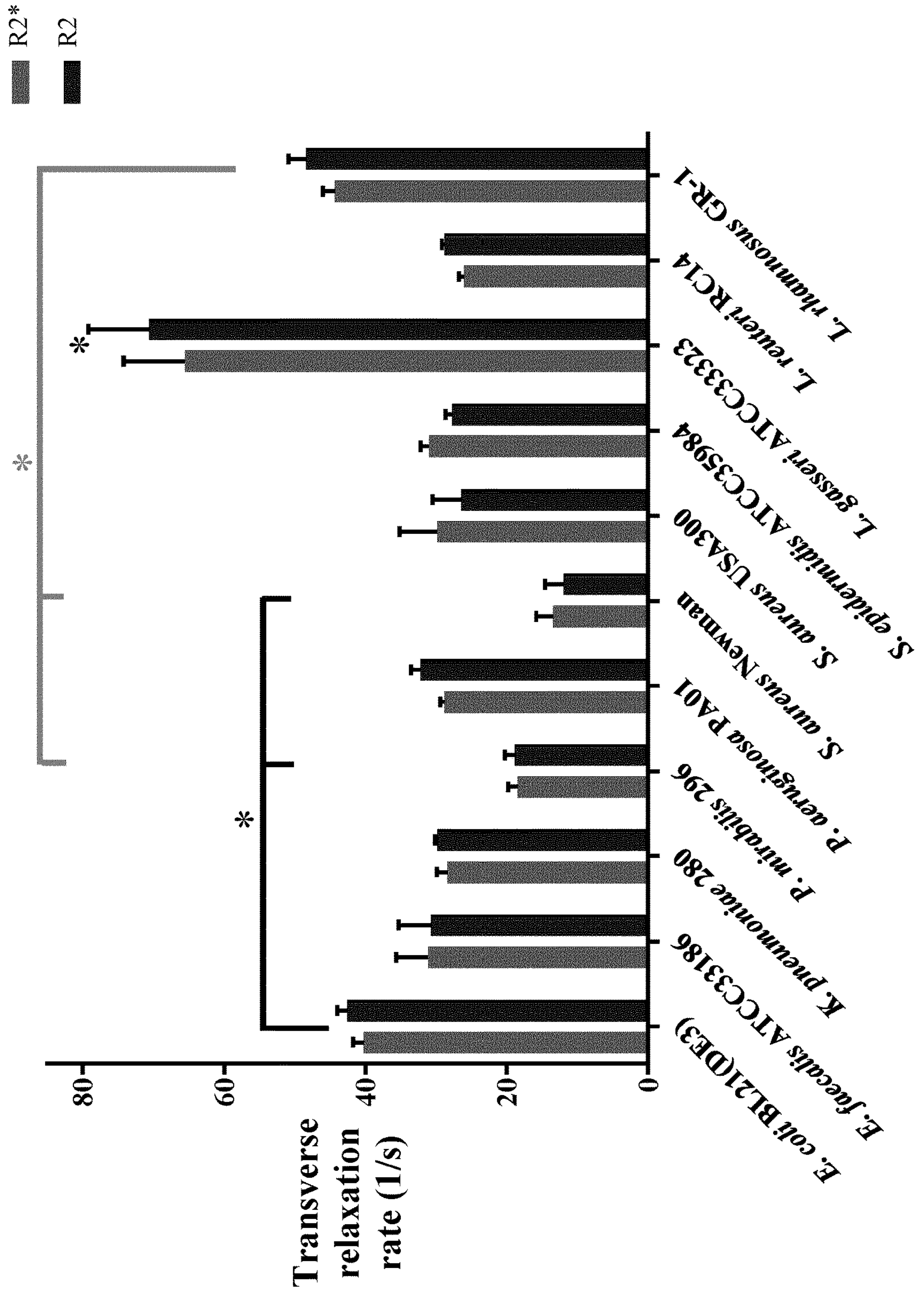
FIG. 14 illustrates the nuclear magnetic resonance signal of different bacteria. Pairs marked with a* are statistically significantly different.

FIG. 14 illustrates the Nuclear Magnetic Resonance (NMR) signal of different bacteria mounted in a gelatin phantom for MRI at 3 T. MR measurements of different bacterial species varied widely. Although there is overlap in the spin-spin relaxation signal (R2) between species of bacteria, calibration would be possible by high resolution NMR relaxometry of fecal samples, allowing for the identification of the different bacteria by relaxation rate and the number of these live bacteria by the signal amplitude at each relaxation rate. For this technique, fecal samples will be processed to put the different bacteria into the slow exchange regime, either by doping the fecal bacteria with a paramagnetic salt like Mn or Gd, or by slowly reducing the hydration of the slurry containing bacteria and bacteriophage.

In all cases, the R2 component of transverse relaxivity (blue bars) dominates the total R2* signal (red bars). The outstanding signal from *L. gasseri* ATCC33323 (see FIG. 11) was found to be significantly higher than any other species tested ($p<0.05$). Both *E. coli* BL21(DE3) and *L. rhamnosus* GR-1 displayed higher relaxivity than *P. mirabilis* 296 and *S. aureus* Newman (black and gray lines, respectively). Measurements for (undiluted) *L. crispatus* ATCC33820 could not be obtained with the MRI pulse sequences used in this data set (FIG. 8 samples) to cover the range in R2 exhibited by various bacteria. Bar graphs show the mean+/−SEM (* $p<0.05$, n=3-5).

Figure 15:
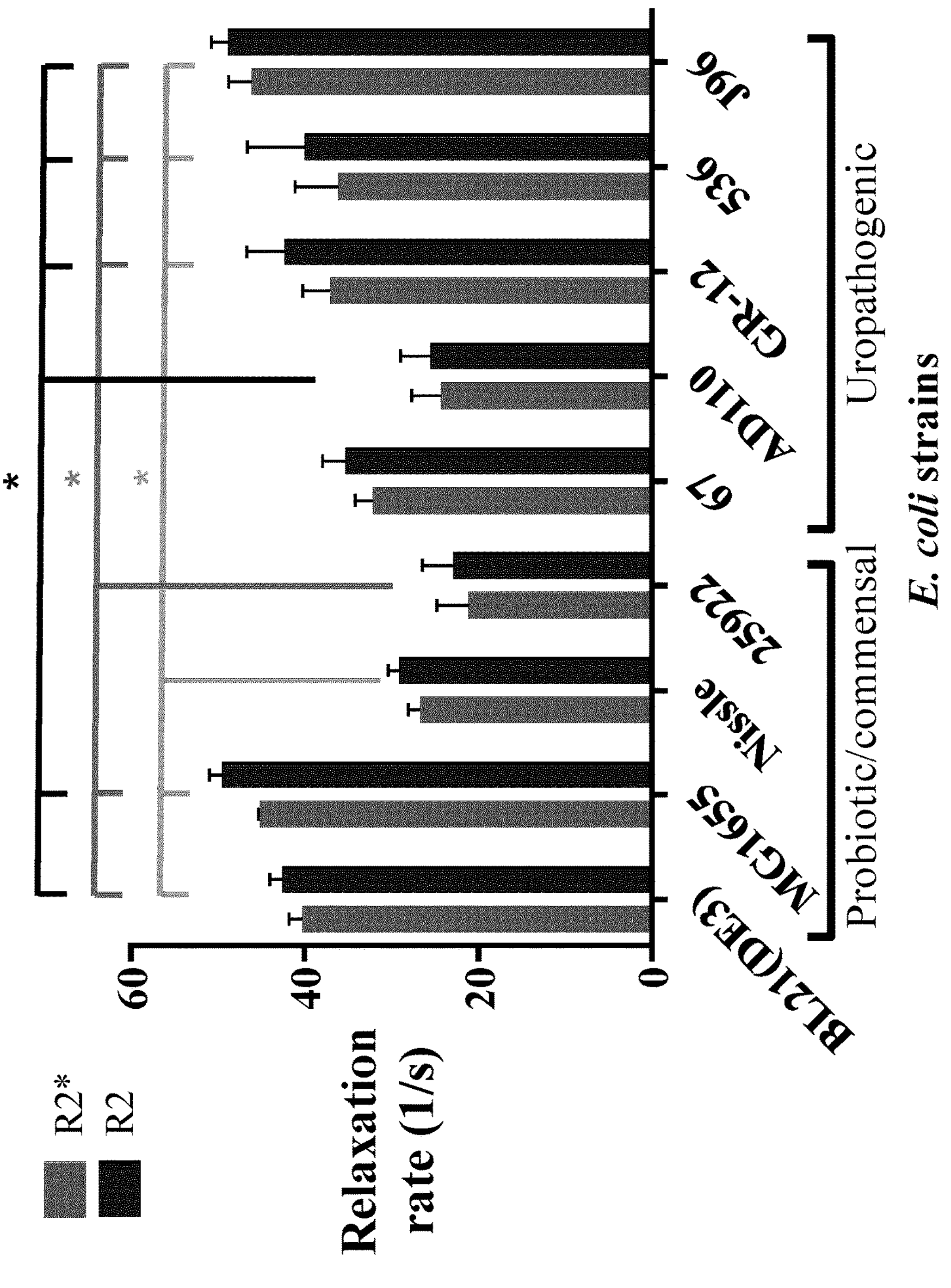
FIG. 15 provides data on additional species of *E. coli* (probiotic, commensal and uropathogenic).

FIG. 15 provides data on additional species of *E. coli* (probiotic, commensal and uropathogenic). *Escherichia coli* were detectable by MRI. Bar graphs compare MR signals from the BL21(DE3) laboratory strain of *E. coli* with select probiotic (Nissle), commensal (MG1655, 25922) and uropathogenic strains (67, AD110, GR-12, 536, J96). All *E. coli* exhibit relatively high transverse relaxation rates, with R2* consisting virtually entirely of an R2 component and little or no R2' contribution (R2*=R2+R2'). One-way ANOVA indicates that R2/R2* of Nissle (light gray lines), 25922 (dark gray lines) and AD110 (black lines) are significantly lower than most other tested strains (* $p<0.05$). Data are the mean+/−SEM (n=3-5).

Effect of $^{89}$Zr on bacterial viability: Bacteria were plated to count CFUs before and after radiolabelling, to understand its acute effects on bacterial viability. Unlabelled and radiolabelled bacteria were quantified at various points over four weeks to explore the long-term effects of bacterial radiolabelling on viability.

Figure 16:
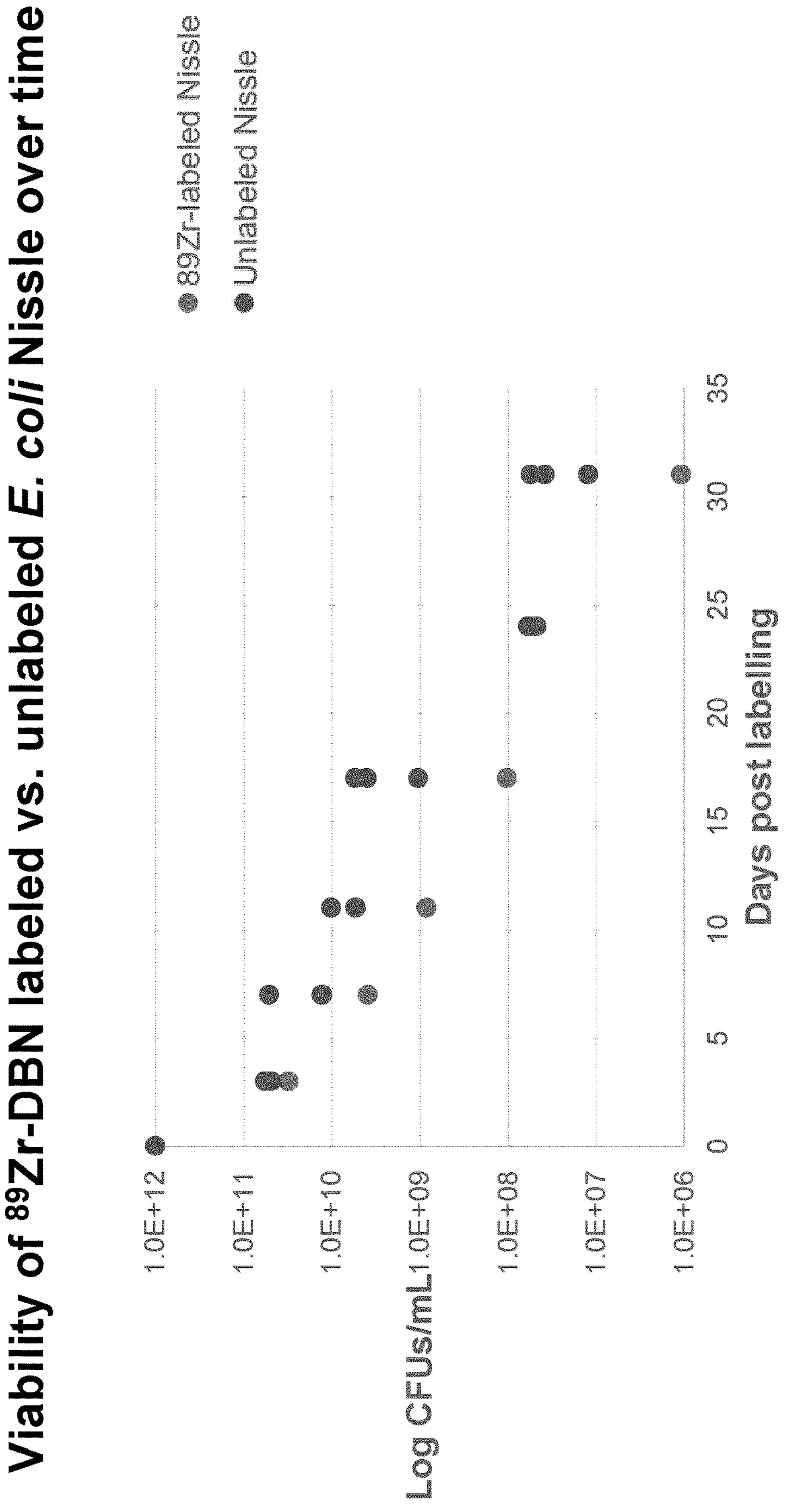
FIG. 16 is a chart illustrating the effect of $^{89}Zr$ radiolabelling on bacterial viability over time.

FIG. 16 illustrates the effect of $^{89}$Zr radiolabelling on bacterial viability over time. *Escherichia coli* Nissle were labelled with $^{89}$Zr-DBN and plated to quantify live cells (CFUs) over time compared to unlabelled cells. Samples of each bacterial stock were serially diluted in sterile $dH_2O$ and plated in triplicate on tryptic soy agar plates. These were incubated at room temperature for 24-36 h before CFUs were counted. Total live cells in the samples were then estimated based on the amount plated at the dilution factor with between 20-60 colonies per replicate. Bacterial viability decreases for both labelled (blue dots) and unlabelled (red dots) cells over time, seen as a decline in CFUs. Cell turnover for radiolabelled bacteria occurs at the same rate as unlabelled counterparts. As the labelled and unlabelled bacterial stocks in this experiment were stored at room temperature and left stagnant, much of the cell death was expected as nutrients were depleted.

The ratio of live to dead cells in unlabelled and radiolabelled samples may also be quantified using live/dead viability staining (SYTO 9 and propidium iodide respectively) with fluorescence microscopy.

Measuring label stability: Unlabelled and radiolabelled bacteria were inoculated into separate chambers of a co-culture apparatus, separated by a 0.2 μm filter. Samples are taken from each chamber at various time points and centrifuged at 10,000×g for 1 min. Supernatants are removed for radioactivity quantification using a well counter, while pellets are washed 3 times with PBS before quantification of radioactivity. All measurements are decay corrected for comparison of $^{89}$Zr content in the initially labelled sample to (a) $^{89}$Zr released into the medium (e.g. either released from chelation or through cell turnover) and (b) potential interactions between unlabelled bacteria and free $^{89}$Zr.

Figure 17A:
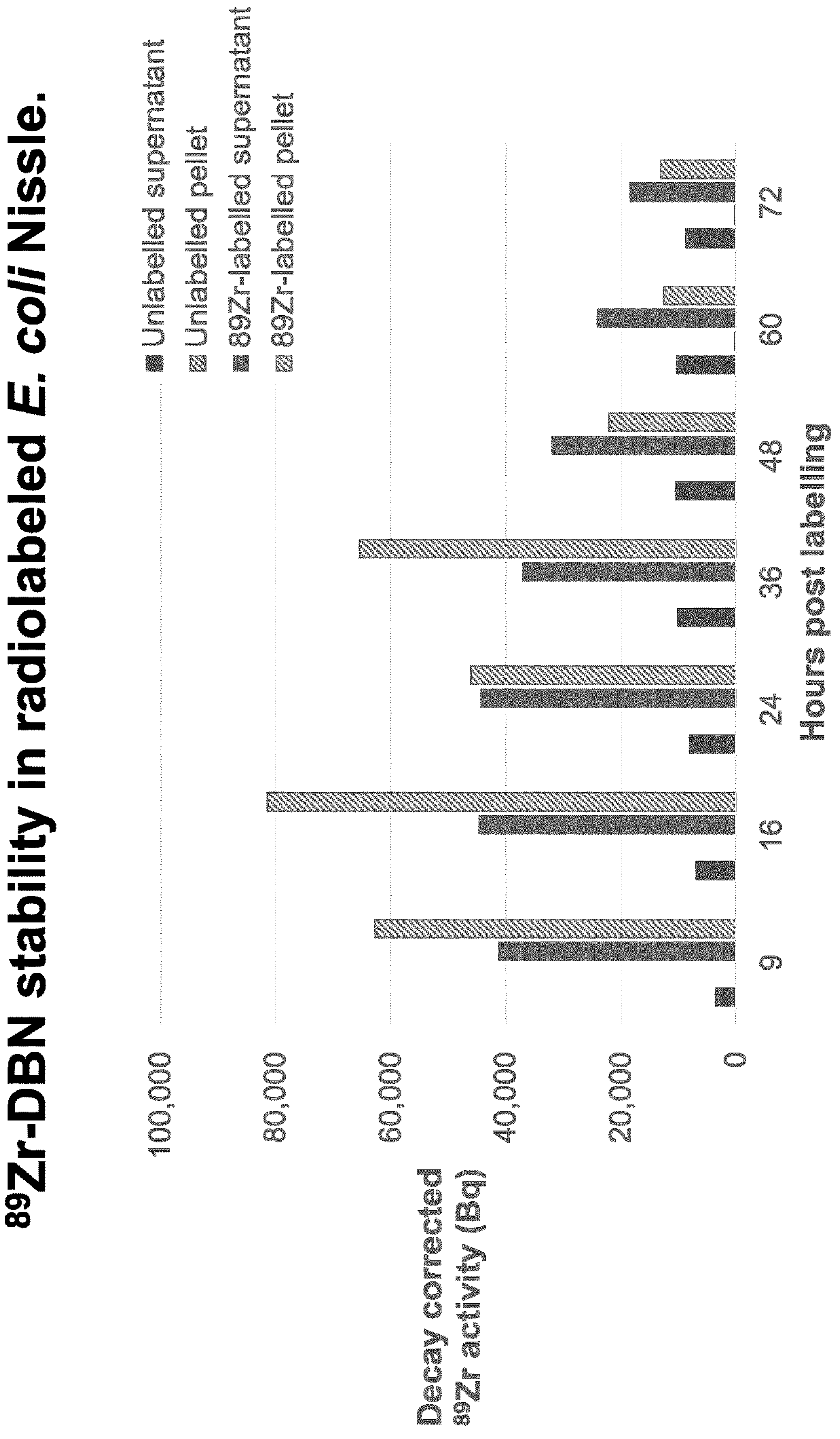
FIGS. 17A and 17B illustrate $^{89}Zr$ stability in radiolabelled *E. coli* Nissle.
Figure 17B:
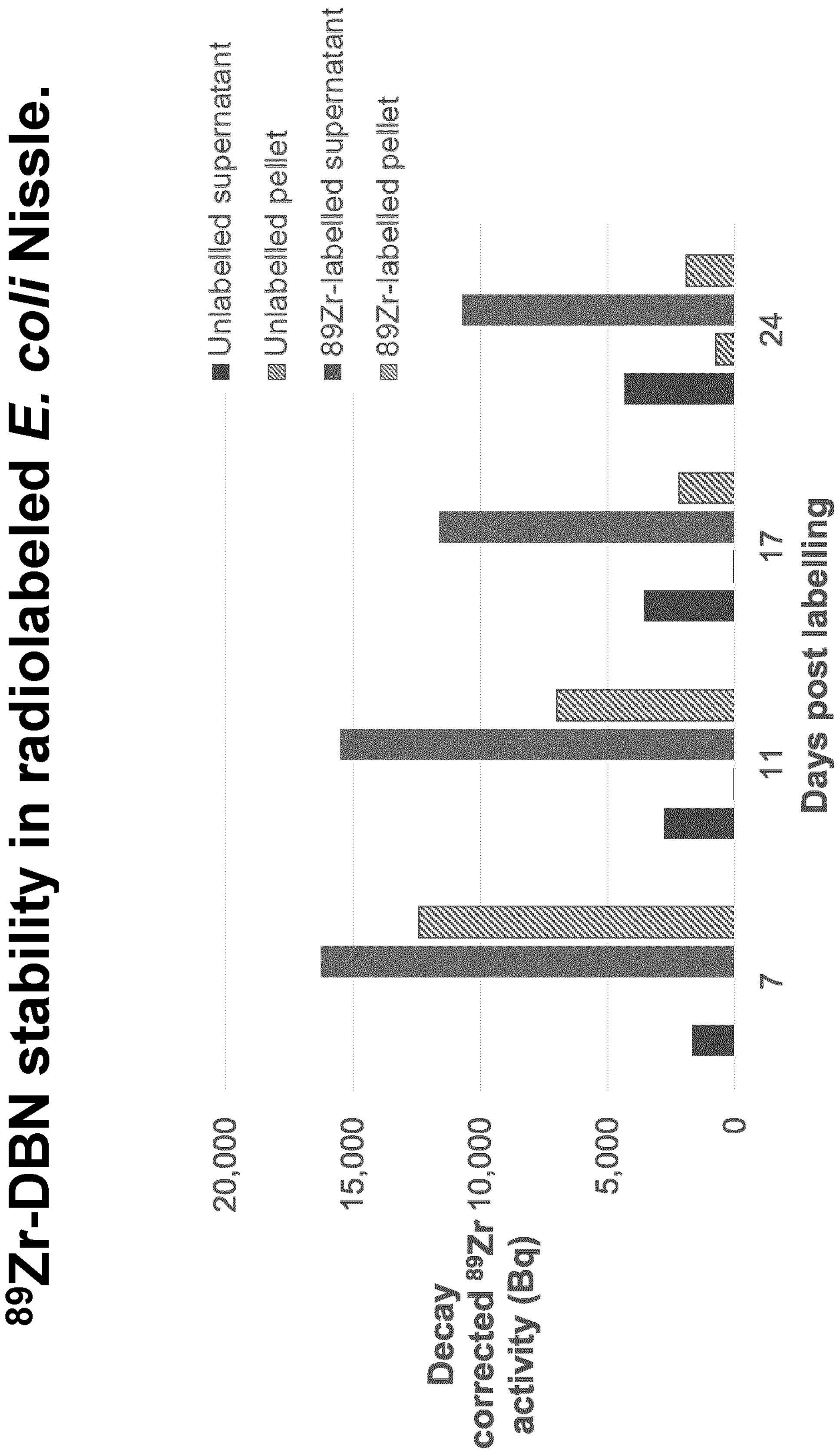

FIG. 17 (17A for time points of 9-72 hours; 17B for time points of 7-24 days) shows that if the radio-isotope such as $^{89}$Zr is released by the chelate or dying cell, then it does not label bacteria. *Escherichia coli* Nissle were labelled with $^{89}$Zr-DBN and inoculated into one chamber of a 2-chamber culture system (co-culture apparatus). The opposite chamber was inoculated with an equivalent amount of unlabelled *E. coli* Nissle. The chambers were separated by a 0.2 μm filter, preventing intact bacteria from crossing between chambers, but allowing the medium, small molecules, some proteins (<200 kDa), and small cell fragments to diffuse across. At various time points, aliquots were removed from each chamber and centrifuged to separate bacteria and supernatant. Bacterial pellets were washed to remove unbound $^{89}$Zr and, using a well counter, $^{89}$Zr was quantified in both supernatants (not including washes; solid bars) and cell pellets (striped bars). The proportion of $^{89}$Zr released into the medium (blue bars) increased as the radiolabelled cell pellet (blue striped bars) decreased over time, reflecting cell turnover and potential loss of chelation. Nevertheless, any $^{89}$Zr that passed between chambers remained in the supernatant medium (red bars) and did not radiolabel unlabelled bacteria (red striped bars).

Label stability can also be assessed on bacterial plates prepared in the same way as described for examining bacterial viability. For stability measures, bacteria must be washed thoroughly before plating to ensure that only bacterial-bound $^{89}$Zr is present on the petri dish. Total radioactivity on plates are quantified using a whole-body counter and decay corrected to examine changes in the level of bacterial-bound $^{89}$Zr over time. Radioactivity in individual colonies may also be assessed by autoradiography.

Example 2: Imaging Gut Bacteria Utilizing $^{111}$In

This example demonstrates how bacteria can be labelled with $^{111}$In (2.8-day half-life) in vitro for bacterial detection, effects on bacterial viability, and label stability.

Radiolabelling bacteria with $^{111}$In: Bacteria are cultured overnight in their preferred medium. Then the bacteria are centrifuged and washed with PBS to remove medium components (e.g. protein). Bacteria are subsequently incubated with $^{111}$In-DOTA-NHS at room temperature for 1 h with shaking. Bacterial radiolabelling is designed to achieve approximately 0.0014 Bq/CFU based on previous viability studies labelling mammalian cells with $^{111}$In-tropolone (Jin et al., 2005). Excess label is removed through centrifugation and washing until the cell-free supernatant contains insignificant amounts of radioactivity.

In vitro SPECT and MRI of $^{111}$In-labelled bacteria: Samples are prepared from cultured, radiolabelled bacteria, mounted in a gelatin phantom and imaged using SPECT followed by MRI or CT, or by SPECT/CT followed by MRI. The MRI can be at various field strengths, including but not limited to 1.5 T, 3 T or 7 T. $^{111}$In-labelled cells are serially diluted in gelatin/PBS, loaded into Ultem wells and then mounted in a spherical gelatin phantom as in FIG. 9.

Effect of $^{111}$In on bacterial viability: Bacteria are plated to count CFUs before and after radiolabelling, to understand its acute effects on bacterial viability. Unlabelled and radiolabelled bacteria are quantified at various points over four weeks to explore the long-term effects of bacterial radiolabelling on viability.

The ratio of live to dead cells in unlabelled and radiolabelled samples may also be quantified using live/dead viability staining (SYTO 9 and propidium iodide respectively) with fluorescence microscopy.

Measuring label stability: Unlabelled and radiolabelled bacteria are inoculated into separate chambers of a co-culture apparatus, separated by a 0.2 μm filter. Samples are taken from each chamber at various time points and centrifuged at 10,000×g for 1 min. Supernatants are removed for radioactivity quantification using a well counter, while pellets are washed 3 times with PBS before quantification of radioactivity. All measurements are decay corrected for comparison of $^{111}$In content in the initially labelled sample to (a) determine $^{111}$In released into the medium (e.g. either released from chelation or through cell turnover) and (b) investigate potential interactions between unlabelled bacteria and free $^{111}$In.

Label stability can also be assessed on bacterial plates prepared in the same way as described for examining bacterial viability. For stability measures, bacteria should be washed thoroughly before plating to ensure that only bacterial-bound $^{111}$In is present on the petri dish. Total radioactivity on plates are quantified using a whole-body counter and decay corrected to examine changes in the level of bacterial-bound $^{111}$In over time. Radioactivity in individual colonies may also be assessed by autoradiography.

Examples 3 and 4: Imaging Bacteria In Vivo Utilizing $^{89}$Zr and $^{111}$In Labelling This example comprises labelling bacteria with $^{89}$Zr (half-life 3.3 days), which permits analysis of the $^{89}$Zr content in biological samples per bacterial cell using PET/MRI imaging. Sample data in a healthy pig provides proof-of-principle and demonstrates persistence of probiotic within the GI tract for at least 4 days post-ingestion. While $^{89}$Zr labelling is described here, the method applies equally when $^{111}$In labelling or other known labelling methods are used with SPECT/MRI imaging.

Methods: Radiolabeled probiotic was delivered in a capsule to healthy pigs. Then PET/MRI was used to delineate the timeframe for translocation of bacteria, from stomach through to lower GI tract and potential migration across the intestinal epithelium to target tissues. The appearance of $^{89}$Zr in feces, urine, and blood were also quantified. The pig samples validated the herein exemplified radiolabelling and imaging methods.

Radiolabelled bacteria, free from unbound $^{89}$Zr, were encapsulated and introduced directly into the stomach of the pigs using a feeding tube. The anesthetized animal was imaged with PET/MRI (Siemens Biograph mMR) for simultaneous monitoring of $^{89}$Zr-DBN labelled bacteria (PET) combined with anatomical information (MRI). Appropriate imaging parameters were established to identify important timelines and ROI for bacterial translocation. Blood, urine and feces are monitored during and between imaging sessions; can be counted to track radiolabelled material; and analyzed for bacterial components by NGS and PCR. Tissue can be collected at endpoint for histology and autoradiography.

Pig model: Animals are procured from a local farm at approximately 6-8 weeks of age (~30 kg) and housed in pairs to permit social interactions for reducing stress and GI disturbances. An animal use protocol (AUP, 2019-119) is implemented, approved to meet standards set by the Canadian Council on Animal Care. Animals are anesthetized prior to inserting a nasal gastric tube for transplantation of the capsules containing $^{89}$Zr-labelled probiotic. Imaging from 1-6 hours post-ingestion confirms correct positioning of capsules in the stomach (see FIG. 18). While under anesthetic, urine is collected continuously. In between imaging sessions, urine and feces are monitored using a metabolic cage. Throughout the experiment, stools are analyzed for $^{89}$Zr-labelled probiotic. Blood samples are collected at each imaging session and monitored using a high purity germanium (HPGe) well counter.

As shown in FIG. 18, Maximum intensity projections (MIP) alone (at right) and registered to MRI (coronal T1-weighted in-phase Dixon, at left) revealed the location of *E. coli* Nissle at 3 times post-ingestion. Initial imaging shows the correct positioning of probiotic capsules in the stomach and esophagus. In this sample data (n=1), some reflux was noted in the tracheal tube and snout. At 4 days post-ingestion, remaining radiotracer was largely contained within the intestinal compartment. Reuse of the tracheal tube showed residual $^{89}$Zr on PET/MRI and was excluded from further analysis. By 7 days post-ingestion, remaining radiotracer was diffuse and close to background.

Figure 21:
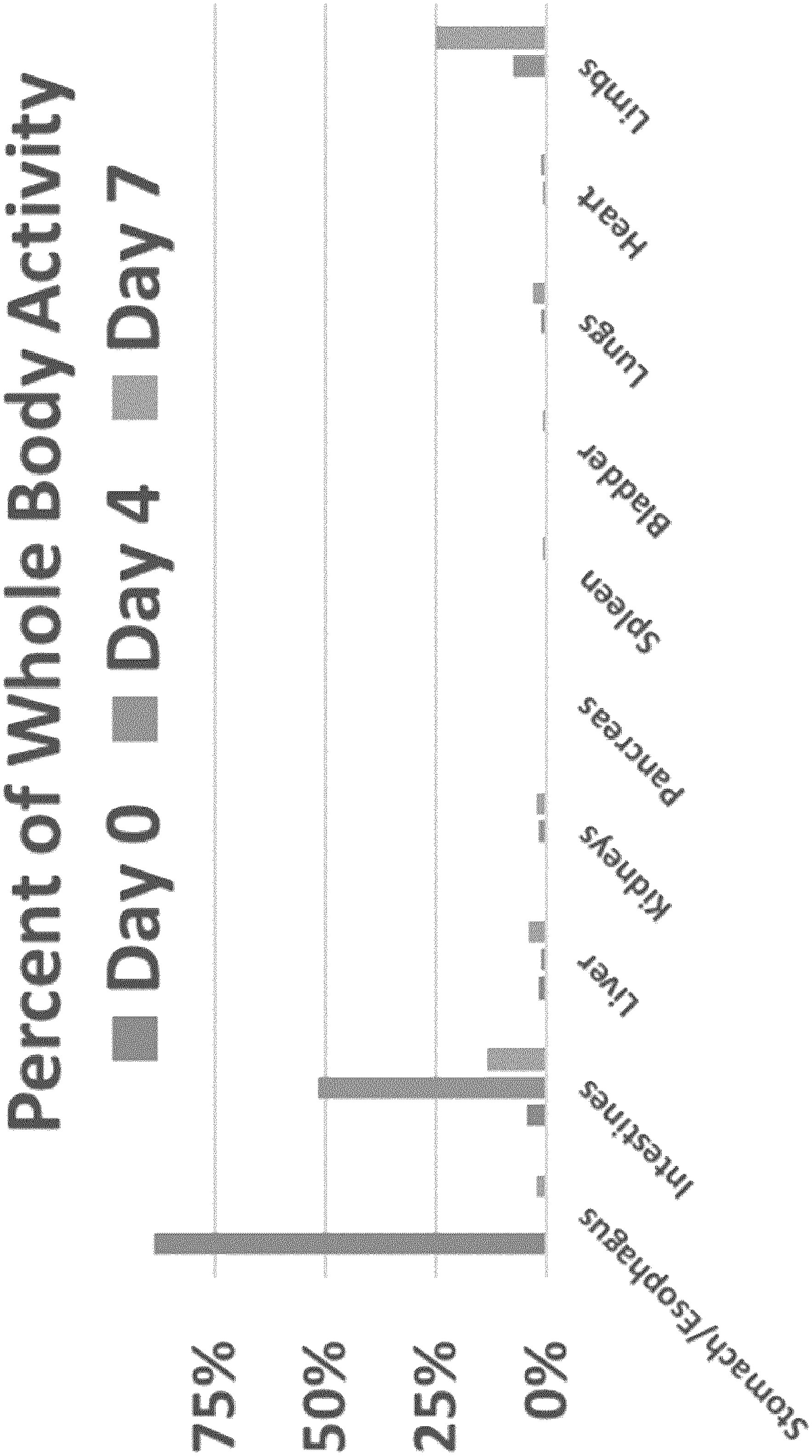
FIG. 21 shows localization of ingested $^{89}Zr$-labelled bacteria to specific sites in the animal (pig).
Figure 25:
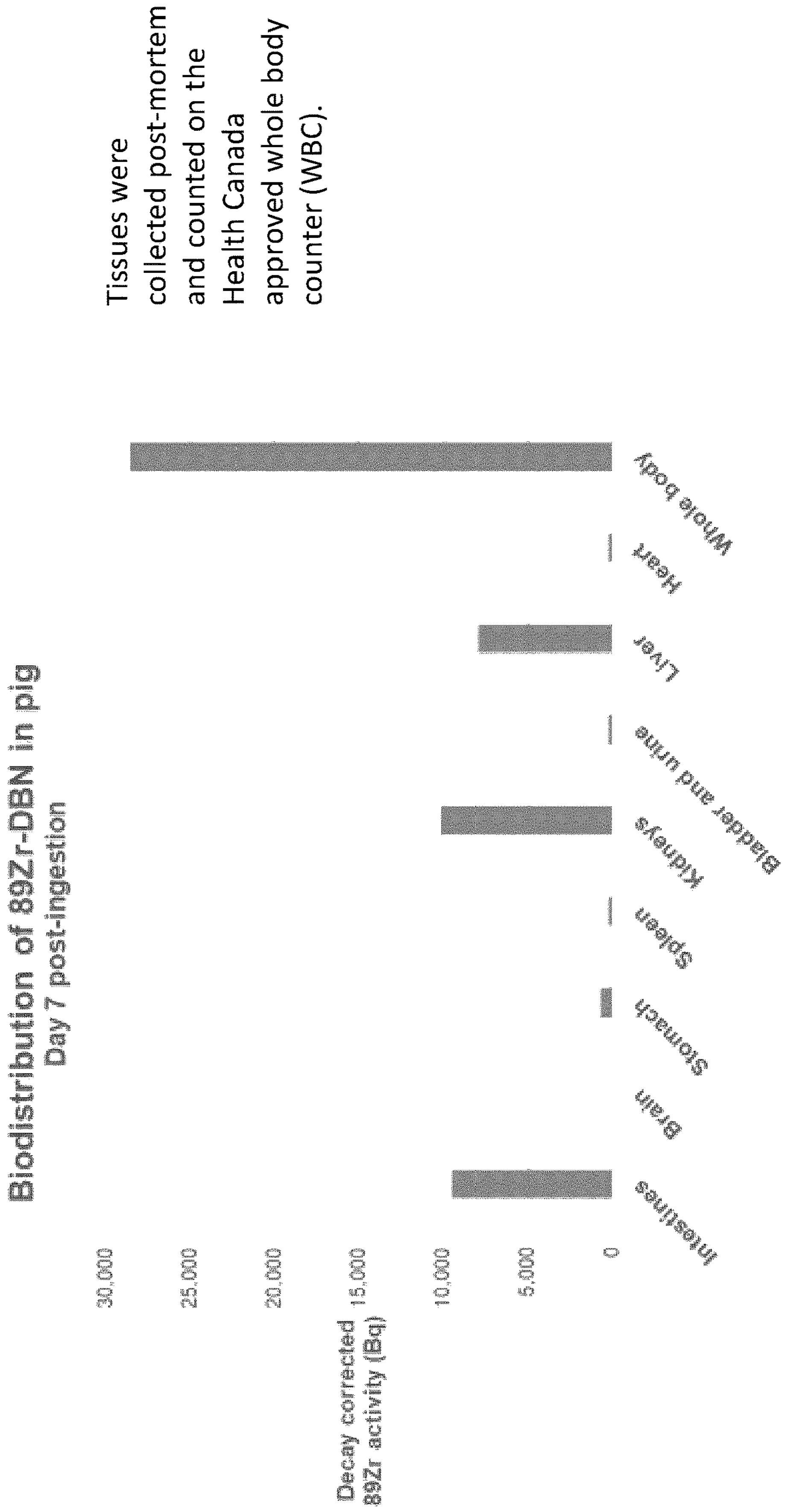
FIG. 25 shows the biodistribution of $^{89}Zr$-DBN in a pig, at day 7 post-ingestion of radiolabelled *E. coli* Nissle.

Imaging timeline: For comprehensive coverage of bacterial movement, three groups of animals are used (see FIG. 19). Translocation of $^{89}$Zr-labelled bacteria is tracked by repeat PET/MRI every 3 days out to endpoints at days 6-8 post-ingestion. Further imaging sessions are targeted to intermediary time points for statistical comparisons and tissue collection. At endpoint, tissues are surgically removed under sterile conditions suitable for downstream bacterial analyses. From these imaging timelines, 3-dimensional (3D) regions of interest (ROI) were defined (see FIG. 20) to determine the time activity curves of specific organs and allow calculation of radiation dose at sites of $^{89}$Zr accumulation both within and outside of the gut. FIGS. 21 and 25 show the biodistribution of the $^{89}$Zr, post-ingestion.

Figure 19:
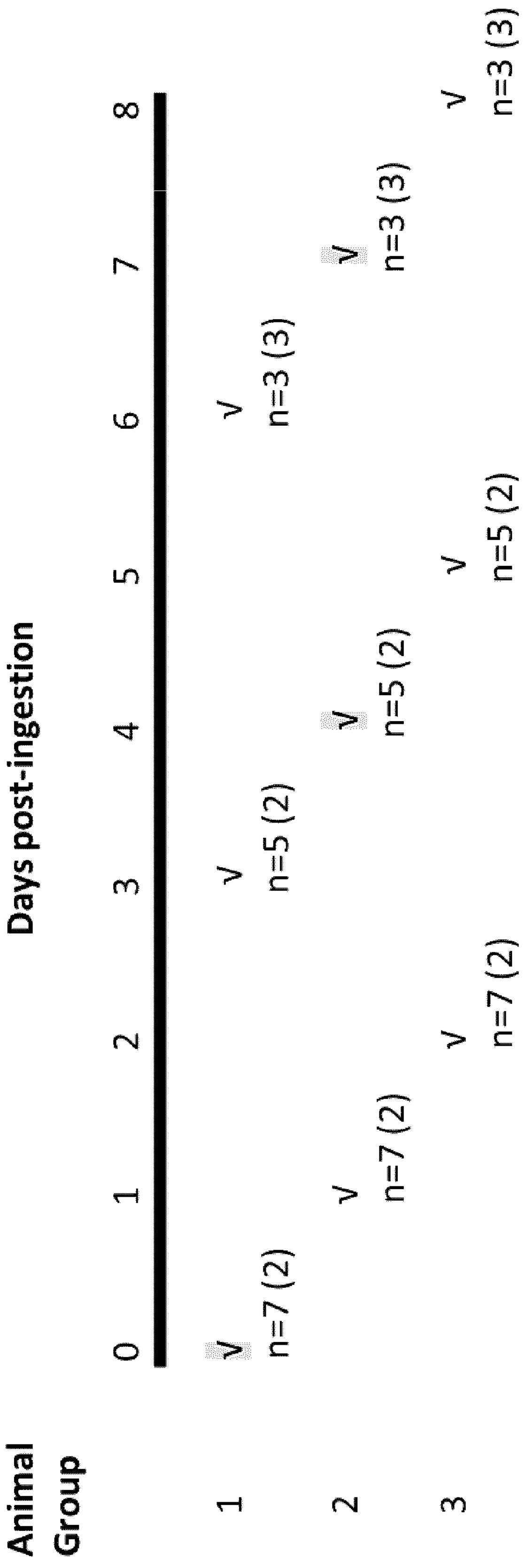
FIG. 19 shows an imaging timeline for coverage of bacterial movement in three groups of animals.

As shown in FIG. 19, PET/MRI was performed to provide cell tracking and spacing between anesthesia. Day 0 represents 6-12 hours post-ingestion.

Imaging sequences: PET/MRI acquisition consisted of four bed positions for whole-body coverage of the pig. At each bed position, PET was acquired for 15-45 minutes (depending on time post-ingestion) while simultaneous MRI is acquired. MRI consists of a 2-point Dixon acquisition for MR-based attenuation correction (MRAC), axial and coronal T2-weighted half-fourier acquisition single-shot turbo spin echo (HASTE) images, T2-weighted spectral attenuated inversion recovery (SPAIR) images, and 3D T1-weighted volume interpolated breath-hold exam (VIBE) images. Bowel activity is minimal due to anesthesia, but if necessary, hyoscine can be administered to further reduce peristalsis. PET was reconstructed with a 3D ordered subset expectation maximization (OSEM) algorithm that accounts for the point spread function of the PET system to improve spatial resolution. Whole-body PET and MRI datasets were automatically composed after the imaging session. Because of simultaneous acquisition in each bed position, PET and MRI data were inherently registered. Total acquisition time is 1.5 to 3 hours, increasing with elapsed time post-ingestion to account for decreased activity due to radioactive decay and excretion of $^{89}$Zr-labelled bacteria. Once the PET/MRI signal became diffuse, residual $^{89}$Zr was monitored using a Health-Canada approved whole-body counter (WBC, FIG. 25).

The number of viable bacteria (CFUs) ingested was determined from the contents of 1 capsule and used to project the scale of probiotic dissemination. Using the WBC, Table 1 estimated post-mortem distribution of the 908 KeV $^{89}Zr$ signal in select organs of a healthy pig.

TABLE 1

Using Imaging to Understand Clinical Problems Associated with Microbiota

| Bacterial Localization | Clinical Problem | Start | Endpoint* | Bacterial Dissemination** |
|---|---|---|---|---|
| Engraftment | Therapeutic role of microorganisms | 140.4 billion $^{89}Zr$-labelled bacteria ingested | ~300 million $^{89}Zr$-labelled bacteria remained | ~300 million in intestines, liver, kidneys |
| Permeability | Leaky membrane barriers associated with chronic disease | | (~0.23% of ingested dose after | ~200 million outside GI tract (~0.15%) |
| Migration | Tracking the extent of dissemination in vivo | | 7 days) | ~100 million/organ liver (~0.08%) kidneys (~0.07%) |

*Calculations are based on the number of CFUs ingested (n = 1 pig) and do not account for bacterial proliferation, cell death or potential loss of $^{89}Zr$ cell label.
**Estimates are derived from analysis of organs post-mortem on a WBC.

As shown in FIG. 20, after ingestion of 89Zr-labelled probiotic, coronal images obtained from T2-weighted HASTE sequences were used to segment pig tissues. In this example of the segmentation at day 4 post-ingestion, most of the radiolabel is confined to the intestinal compartment. The contaminated tracheal tube shown in FIG. 18 was omitted from analysis.

Biodistribution: Dissemination of bacteria to specific sites in the animal (see FIG. 21) was identified by PET/MRI as tissue regions containing radiotracer. These ROI will define the tissue to be excised post-mortem, along with adjacent unlabelled tissue, to be used as a control for potential bacterial DNA contamination. Histology and autoradiography (BeaQuant, AI4R) will provide evidence of bacterial localization in excised tissue to complement DNA analyses.

Figure 24:
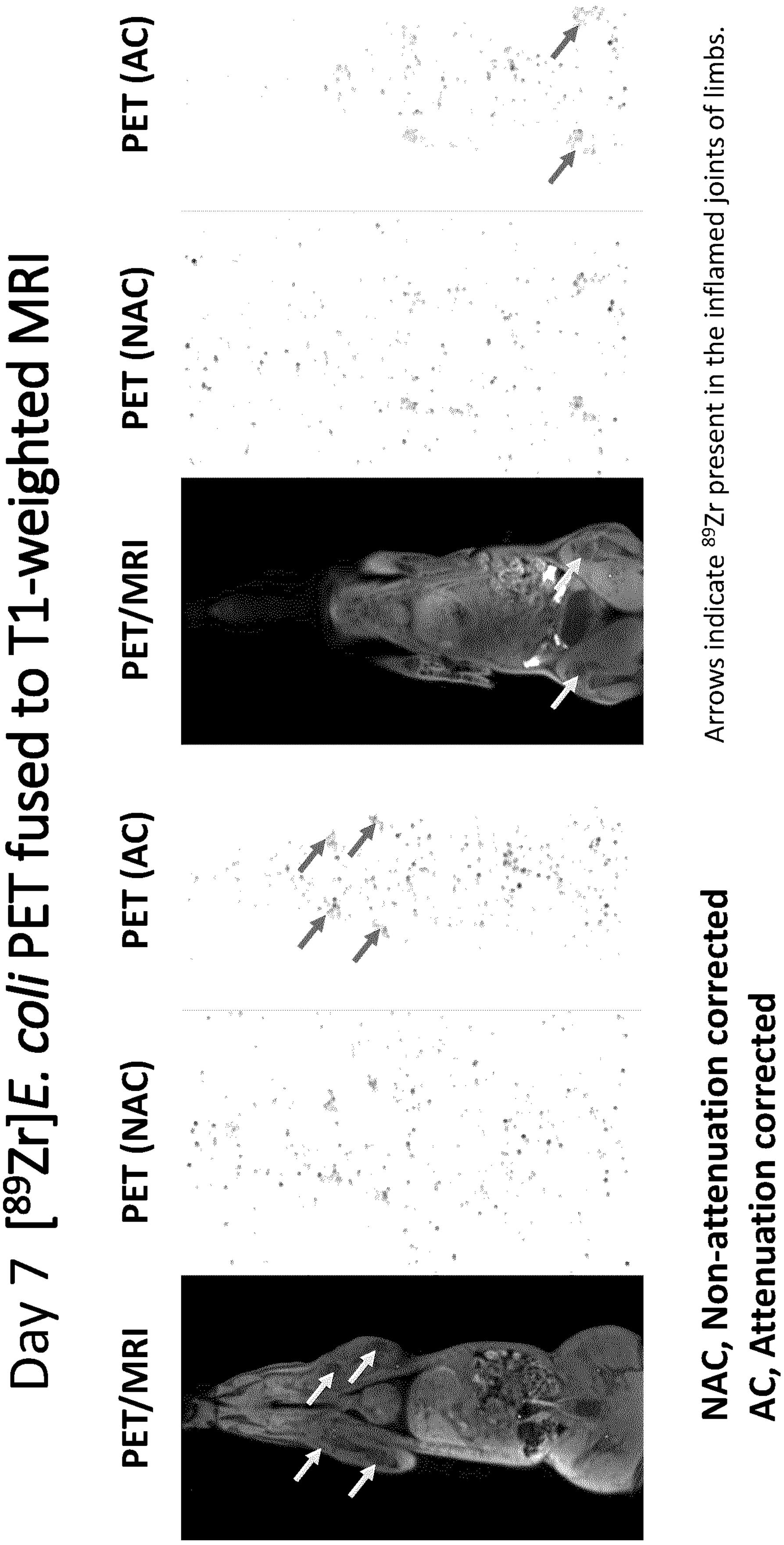
FIG. 24 shows the appearance of $^{89}Zr$ in the limbs of a pig at day 7 post-ingestion of radiolabelled *E. coli* Nissle.

As shown in FIG. 21, the time course showed most of the ingested $^{89}Zr$-labelled bacteria translocating from stomach and esophagus on the day of radiotracer ingestion (blue bars) to the intestinal compartment 4 days later (orange bars). Despite little or no signal in the bladder, $^{89}Zr$ in the liver, kidneys and lung was minor compared to accumulation in the (inflamed) joints of limbs by day 7 post-ingestion (grey bars) (FIG. 24).

This example shows microbial retention and/or translocation from the gut after ingestion and describes an imaging procedure for tracking these cells in large animals and humans, regardless of variations in microbiota from diverse hosts.

Pig growth during the experiment is accommodated by the scanner bore size and developmental changes faithfully tracked. While anesthetic can reduce motion in the gut and confound the timing of bacterial translocation, reduced peristalsis is advantageous for GI image analysis and may be facilitated by the short-lived paralytic agent, hyoscine (half-life 20 minutes). When needed, dextran sulfate can be administered to maintain gut motility between imaging sessions. Biodistribution of $^{89}Zr$ measured by PET/MRI may differ from the WBC. To address this discrepancy, the systems can be calibrated.

Example 5: Imaging Bacteria In Vitro Utilizing $^{89}Zr$ Labelling of Bacteriophage This example demonstrates how bacteria can be indirectly radiolabelled in vitro through $^{89}Zr$ labelling of bacteriophage.

Labelling of bacteriophage: A strain of Myoviridae or Siphoviridae propagated with *Escherichia coli* was isolated, purified, and incubated with $^{89}Zr$-DBN (see FIG. 22). The labelling is in proportion to the bacteriophage surface area. Myoviridae have an icosahedral head with an average diameter of 85 nm and cylindrical tails from 170-240 nm in height and 16-20 nm in diameter (generally 220 nm×18 nm).

Icosahedral surface area, $A_1=5*\sqrt{3}*(r_1/\sin 72°)^2$, where $r_1$ is the radius of the head.

Cylinder surface area, $A_2=(2\pi r_2 h_2)+2\pi(r_2)^2$, where $h_2$ is the tail height and $r_2$ is the tail radius.

Total surface area, $SA=A_1+A_2=17295\ nm^2+12950\ nm^2=30245\ nm^2$

With a surface area ~30000 $nm^2$, approximately $0.1\times10^{-4}$ Bq/phage is considered to be nontoxic. Labelled bacteriophage is purified from unbound label by one of the following methods: size exclusion chromatography (including dialysis), reversibly binding Sepharose beads, or ultracentrifugation.

Assessing label stability and efficacy of indirect bacterial labelling: Labelled bacteriophage is added to one chamber of a co-culture apparatus, with *E. coli* in the other chamber, separated by a filter allowing phage, but not bacteria, to travel between chambers. Samples are taken from each chamber at various time points over a 72 h period. These samples are centrifuged at 10,000×g for 1 min to pellet out bacteria, which are washed with PBS. $^{89}Zr$ activity in both pellets and supernatant are measured using a well counter. Bacteria and phage are also plated for quantification in terms of colony-forming units (CFUs) and plaque-forming units (PFUs) respectively. The stability of $^{89}Zr$-DBN labelling of phage is assessed by quantifying free label vs. phage-bound label over time using the same purification method as described above.

Figure 22:
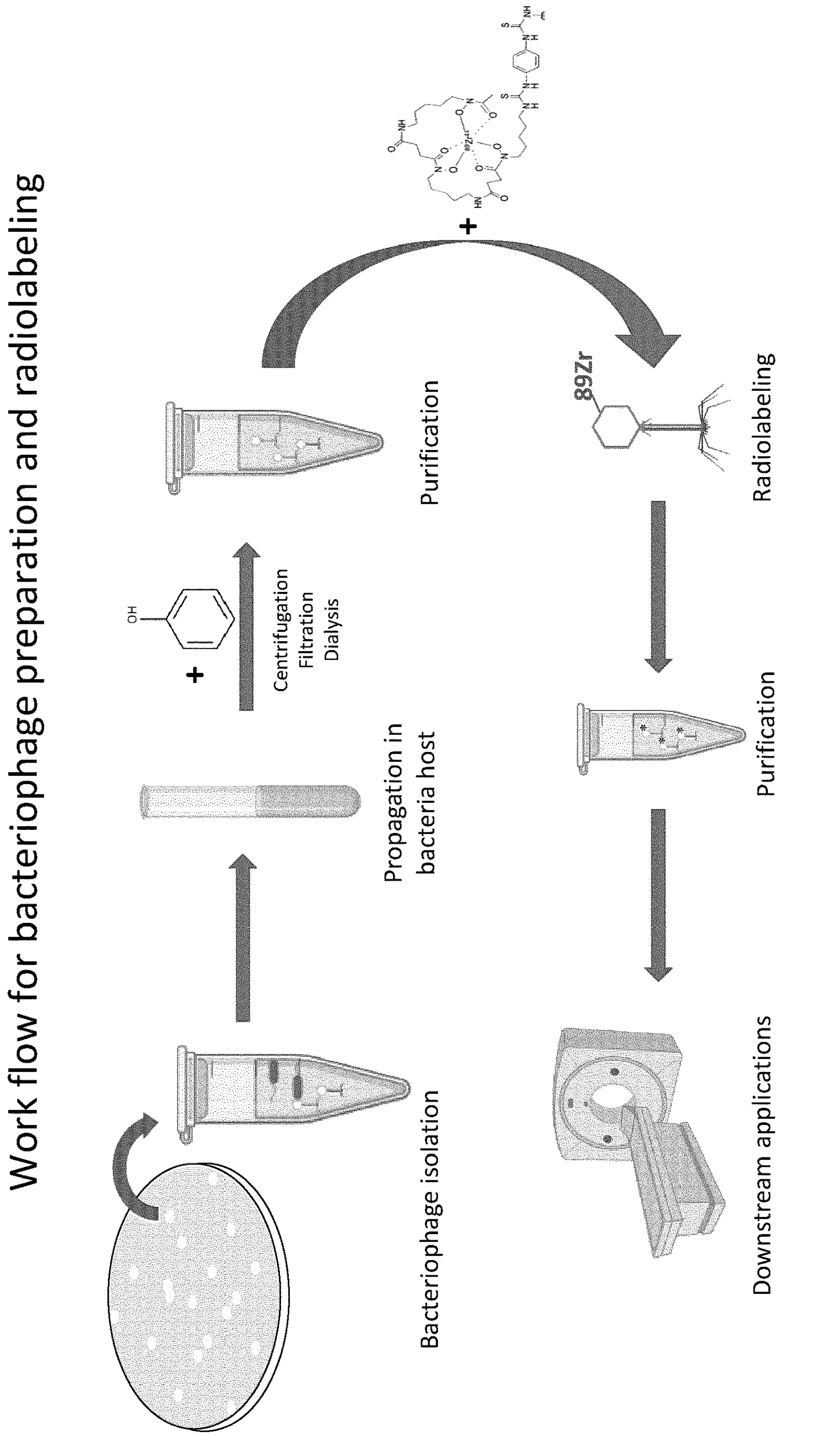
FIG. 22 shows an example work flow for bacteriophage preparation and radiolabelling.
Figure 23:
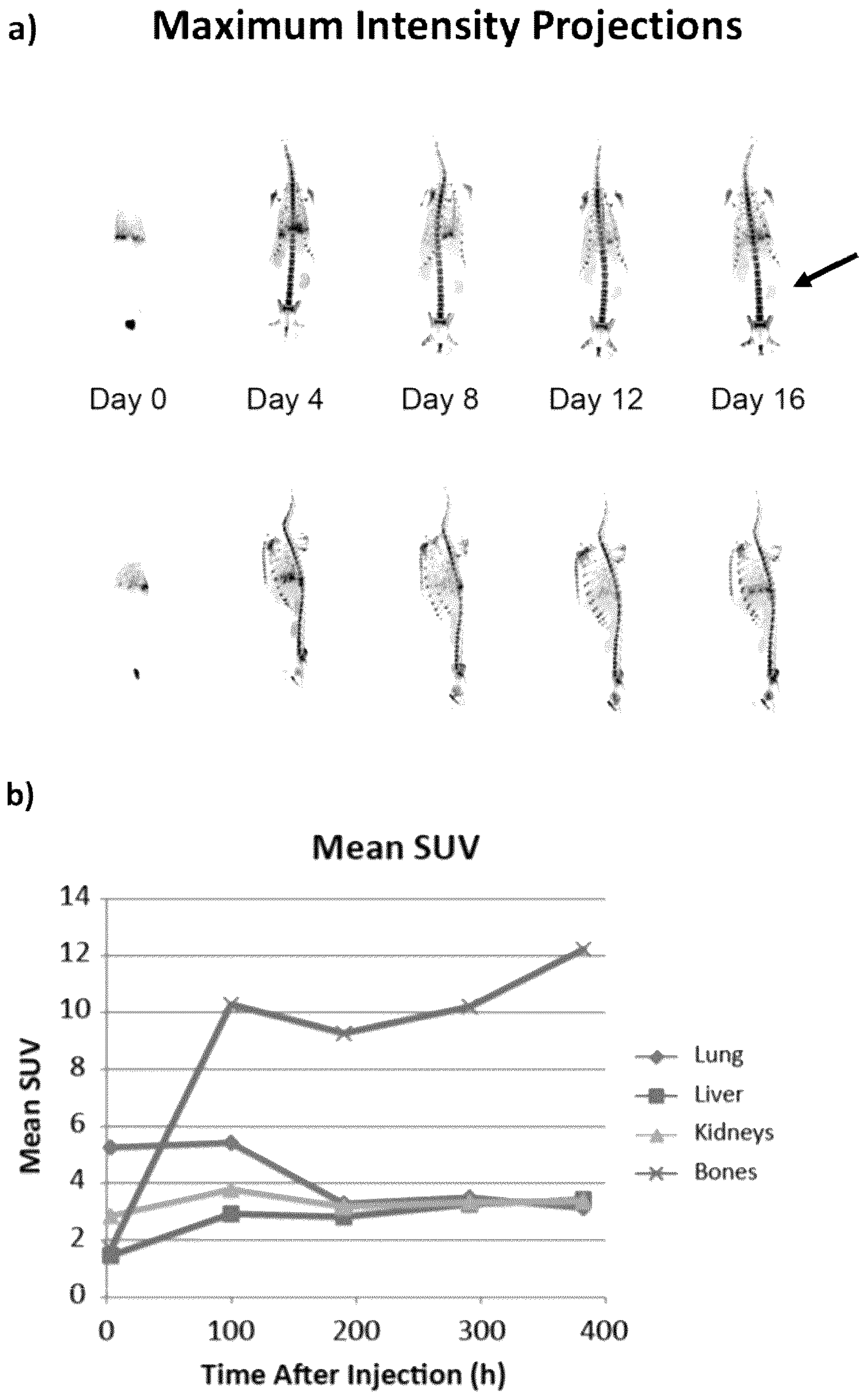
FIG. 23 (*a*) shows the maximum intensity projections from PET imaging of a dog intravenously injected with $^{89}Zr$-phosphate.

As shown in FIG. 22, individual isolated bacteriophage strains are propagated in their bacterial host and purified to remove contaminants, such as bacteria, unbound proteins, and salts. Purified phage are incubated with $^{89}Zr$-DBN, so that radiolabel can bind to primary amines on cell surface proteins that compose both the bacteriophage head and tail. Unbound radiolabel is removed to provide purified radiolabelled phage for downstream in vitro and in vivo applications.

Example 6: Imaging Bacteria In Vivo Utilizing $^{89}Zr$ Labelling of Bacteriophage This example demonstrates how gut bacteria can be indirectly radiolabelled in vivo through $^{89}Zr$ labelling of bacteriophage.

Labelling of bacteriophage: A strain of Myoviridae or Siphoviridae propagated with *E. coli* is isolated, purified, and incubated with $^{89}Zr$-DBN at approximately $0.1\times10^{-3}$ Bq/phage. Labelled bacteriophage is purified from unbound label by one of the following methods: size exclusion chromatography, reversibly binding Sepharose beads, or ultracentrifugation (FIG. 22).

Delivery of bacteriophage labelled with $^{89}Zr$ to an animal/human: These phage are loaded into a capsule and swallowed or deposited by tube into the gut through the esophagus or anus.

Determination of 3-D maps/images of $^{89}Zr$ activity and MRI R2 and/or R2* values in animals/humans: The animal/human is placed into a hybrid PET/MRI or sequentially imaged with PET and MRI. First a baseline MRI is taken prior to the delivery of $^{89}Zr$ labelled bacteriophage. This 3-D MRI data is converted to a 3-D distribution of R2 and R2*. Then PET/MRI data is collected at various times after delivery of $^{89}Zr$ labelled phage to follow, in time, the extent of engraftment, gut permeability and migration as the $^{89}Zr$-labelled phage bind their host bacteria, in this case, *E. coli*. Using different bacteriophage allows for targeting of different bacterial populations within the gut, including manganese dependent lactobacilli for example. MRI is used primarily for anatomical imaging using pulse sequences such as T2-weighted half-fourier acquisition single-shot turbo spin echo (HASTE) images as well as sequences for PET signal attenuation corrections. Whole-body PET and MRI datasets are automatically composed after the imaging session. Because of simultaneous acquisition in each bed position, PET and MRI data are inherently registered. Total acquisition time is 1.5 to 3 hours, increasing with elapsed time post-ingestion to account for decreased activity due to radioactive decay, excretion, and propagation of $^{89}Zr$-labelled bacteriophage and/or the host cells they infect.

Generation of 3-D images of bacteriophage concentration from the PET data ($^{89}Zr$ 3-D activity maps): Use the formulation described above for the non-specific uptake of $^{89}Zr$ in the gut and in the body external to the gut i.e. NSU and NSUE respectively.

Determination of NSU: A sample of stool is counted for radioactive concentration in Bq of $^{89}Zr$ i.e. AC (before). Then the non-cellular debris is removed, and the sample recounted to give AC (after). Then NSU is calculated as NSU=AC (before)−AC (after). Labelled phage will primarily be found in the cellular component as they are bound to their host bacteria, though it should be noted that upon bacterial host cell lysis virions will be released into the extracellular space to infect more cells.

Determination of NSUE: A blood sample and/or a saliva sample and/or a urine sample is counted for radioactive concentration in Bq of $^{89}Zr$ i.e. ACE (before). Then the non-cellular debris is removed, and sample recounted to give ACE (after). Then the NSUE is calculates as NSUE=ACE (before)−ACE (after).

Example 7: Imaging Bacteria In Vivo Utilizing $^{89}Zr$ Labelling of Bacteriophage This example demonstrates how bacteria throughout the body can be indirectly radiolabelled in vivo through $^{89}Zr$ labelling of bacteriophage.

Labelling of bacteriophage: Bacteriophage propagated with their bacterial host are isolated, purified, and incubated with $^{89}Zr$-DBN at approximately $0.1\times10^{-3}$ Bq/phage. Labelled bacteriophage are purified from unbound label by one of the following methods: size exclusion chromatography, reversibly binding Sepharose beads, or ultracentrifugation (see FIG. 22).

Delivery of bacteriophage labelled with $^{89}Zr$ to an animal/human: These phage are delivered to the animal/human by intravenous, intraarterial, subcutaneous, intraperitoneal, intramuscular injection, infusion or intracranial administration (e.g. intrathecal or intraventricular). The bacteriophage disseminate and infect their host bacteria. These bacteria may be involved in a local tissue infection, in an orthopedic infection, at the site of a tumour, or may be dispersed outside of the gut into other tissues. In the latter, bacteria provided to the animal/human in the form of a fecal transplant may exit the GI tract due to high intestinal permeability and spread to other tissues. At this point, these bacteria can be imaged through direct radiolabelling, but discrimination between live and dead cells non-invasively in the host is extremely challenging by prior art methods. Since bacteriophage will only infect live cells in order to propagate, indirect bacterial labelling through phage confirms the presence of live bacterial across various tissues.

Determination of 3-D maps/images of $^{89}Zr$ activity and MRI R2 and/or R2* values in animals/humans: The animal/human is placed into a hybrid PET/MRI or sequentially imaged with PET and MRI. First a baseline MRI is taken prior to the delivery of $^{89}Zr$ labelled bacteriophage. This 3-D MRI data is converted to a 3-D distribution of R2 and R2*. Then PET/MRI data is collected at various times after delivery of $^{89}Zr$ labelled phage to follow, in time, the extent of localization, engraftment, and migration as they infect their host bacteria. MRI is used primarily for anatomical imaging using pulse sequences such as T2-weighted half-Fourier acquisition single-shot turbo spin echo (HASTE) images as well as sequences for PET signal attenuation corrections. Whole-body PET and MRI datasets are automatically composed after the imaging session. Because of simultaneous acquisition in each bed position, PET and MRI data are inherently registered. Total acquisition time is 1.5 to 3 hours, increasing with elapsed time post-ingestion to account for decreased activity due to radioactive decay and excretion of $^{89}Zr$-labelled bacteria.

Example 8: Imaging Bacteria In Vitro by Labelling with $^{52}Mn$

This example demonstrates how manganese dependent bacteria are loaded with $^{52}Mn$ (5.6-day half-life), deposited into the gut and then imaged using hybrid PET/MRI.

Loading bacteria with $^{52}Mn$: A species of bacteria that is dependent on manganese (e.g. *Lactobacillus reuteri* RC-14) is incubated in media with an optimal concentration of manganese (0.1-0.15 mM) and stimulated to proliferate. After the bacteria have been allowed to proliferate in this optimal media concentration, each bacterium will have incorporated approximately 100,000 Mn atoms. Then the bacteria are centrifuged and re-suspended in manganese free media. To this media is added $10^{-4}$ Bq of $^{52}Mn$ per bacterium for a period sufficient to label each bacterium with approximately 40 atoms of $^{52}Mn$ resulting in approximately $5.6\times10^{-5}$ Bq/cell. Typically, for one billion bacteria approximately 500 k Bq of $^{52}Mn$ ($10\times5\times10^{-5}\times10^{9}$ Bq) is added to the cell media and incubated for 5 days with shaking.

The labelled bacteria is harvested and $^{52}Mn$ not incorporated into the bacterial cells removed through centrifugation and resuspension in $^{52}Mn$ free media or PBS until the supernatant does not contain significant amounts of $^{52}Mn$.

Delivery of $^{52}Mn$ labelled bacteria to an animal or human: In one embodiment the $^{52}Mn$ labelled bacteria are loaded into a fecal carrier packed into capsules and swallowed or deposited by tube into the gut through the esophagus or anus. In other applications, the $^{52}Mn$ labelled bacteria are loaded into media containing a physiological concentration of manganese and delivered to the animal/human by ingestion, intravenous, intraarterial, subcutaneous, intraperitoneal, intramuscular injection or infusion or intracranial administration (intrathecal or intraventricular).

Determination of 3D maps of $^{52}$Mn concentration in the animal/human: The subject/patient (animal/human) is placed into a hybrid PET/MRI or sequentially imaged with PET and MRI. The imaging is repeated to follow the time course of the extent of engraftment, gut permeability, and localization of the radioactivity. Given that manganese is a strong paramagnetic MRI contrast agent that strongly increases R2 and R2*, prior to the delivery of $^{52}$Mn labelled bacteria, an R2 and/or R2* map of the animal/human is taken (baseline measurement). Then after the delivery of $^{52}$Mn labelled bacteria the PET/MRI data collection includes, for each timepoint, R2 and/or R2* maps.

Generation of 3-D images of bacteria concentration: The 3-D bacteria concentration in the gut is calculated using the equations described above. Where a significant amount of $^{52}$Mn is detected by PET, there will be $^{52}$Mn within live cells and $^{52}$Mn in background NSU and NSUE due to release of $^{52}$Mn from cell death and potential release of $^{52}$Mn from live cells. The change in R2/R2*(ΔR2, ΔR2*) from baseline is linearly related to the concentration of total manganese from the sum of live bacteria in the associated imaging voxel. As there is manganese in mammalian tissue, the concentration of manganese per cell will remain relatively constant, but there could be a small loss of $^{52}$Mn in the cell due to exchange between manganese in the cell and the extra cellular pool. Hence, Bq per bacteria (ATB(t)) will equal the activity of Bq in the voxel divided by the ΔR2 (or ΔR2*). This will allow the calculation of TB (x,y,z,t) in the gut and TBP (x,y,z,t) external to the gut. In some experiments where the ΔR2 (or ΔR2*) is large enough this approach will be sufficient.

When this is not the case, then stool samples are analyzed to determine NSU and ATB(t) and body fluids to determine NSUE and ATB(t). For the gut, stool samples are also analyzed to determine the activity of $^{52}$Mn per bacterium (*L. reuteri* RC-14) which account for dilution of $^{52}$Mn due to proliferation. The stool samples are also analyzed for determination of the non-specific uptake (NSU) to account for $^{52}$Mn release from bacteria that have died or $^{52}$Mn that has been released by live bacteria (*L. reuteri* RC-14) through exchange with the extra cellular pool.

Analysis of the stool samples for $^{52}$Mn activity per cell and determination of non-specific uptake (NSU): A fecal sample is placed in a high resolution high purity germanium detector (HPGe) and the activity of $^{52}$Mn per gram of material (Ac(before)) is determined by analyzing the gamma-ray spectrum of $^{52}$Mn including not only the 511 KeV annihilation radiation but also one or more of the 744 KeV, 935 KeV and the 1434 KeV gamma rays. Then the sample is recounted after the non-cellular debris is removed (Ac(after)). Then the:

$$NSU=Ac(before)-Ac(after)$$

$$^{52}Mn(live)=Ac(after)$$

Then the number of live bacteria labelled with $^{52}$Mn is determined in one of or both of the following two procedures. In one embodiment, the fecal sample is put into the slow water exchange limit by doping of the sample with a paramagnetic agent and determining the amplitude of the R2* corresponding to the bacteria in question (i.e. for this example *L. reuteri* RC-14). In another embodiment, next generation sequencing is used to determine the number of viable bacteria per gram.

For the determination of bacteria concentration in the body outside of the gut, samples of saliva, blood and/or urine are analyzed to determine $^{52}$Mn activity per bacterium and NSUE as is outlined above for the stool. Then the 3-D activity of $^{52}$Mn can also be converted to 3-D concentration of bacteria (*L. reuteri* RC-14). The PET and MRI images are registered and the MRI images allow the 3-D PET or PET-derived images to be located with respect to location within the body and quantified.

Example 9: Imaging Bacteria In Vivo by Labelling Manganese Dependent Bacteria with $^{89}$Zr This example demonstrates how a) manganese dependent bacteria are labelled with $^{89}$Zr-DBN, b) introduced into animals/humans, c) imaged with PET/MRI and d) 3-D maps/images of the concentration of these bacteria are derived.

Manganese dependent bacteria are grown to approximately 10 billion under physiological manganese concentration. Once the target number is reached $^{89}$Zr-DBN is added to the cell culture. For 10 billion bacteria, the target labelling is 0.005 Bq/cell and the expected labelling efficiency is approximately 80%. Hence, to 1 billion cells (typically in 500 μL of cell culture) 10 MBq is added to the washed cells. This is allowed to incubate at 37° C. for 60 min in a shaker. After incubation, the cells are washed four times to remove $^{89}$Zr not covalently bound to protein amino groups on the bacteria outer cell membrane.

Delivery of manganese dependent bacteria labelled with $^{89}$Zr to an animal/human: These bacteria are loaded into a fecal carrier packed into a capsule and swallowed or deposited by tube into the gut through the esophagus or anus. (Note that in other embodiments, the $^{89}$Zr labelled bacteria (with intracellular manganese detected by MRI and $^{89}$Zr by PET) could be delivered to the animal/human by intravenous, intraarterial, subcutaneous, intraperitoneal, intramuscular injection or infusion and intracranial (e.g. intrathecal or intraventricular).)

Figure 26:
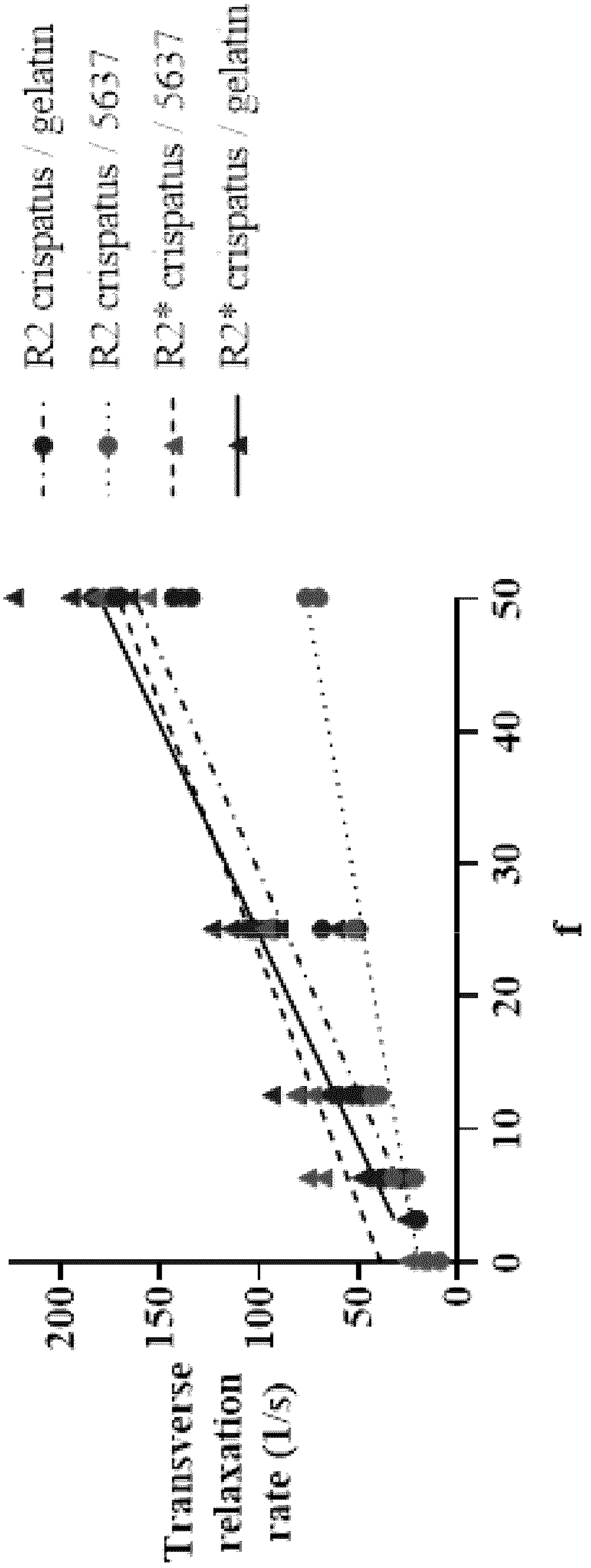
FIG. 26 shows R2* and R2 in mixtures of *L crispatus* and bladder cells. Cultured cells were serially diluted; mounted in a gelatin phantom; and analyzed by MRI at 3 T. The graph compares R2 (circles) and R2* (triangles). Blue symbols denote *L. crispatus* ATCC33820 diluted in gelatin alone; red symbols denote mixed samples of *L. crispatus* and 5637 bladder cells. Lines demonstrate the linear regression within each sample type and MR measure ($r^2$>0.91 for all Pearson correlation coefficients). Whether diluted in gelatin or bladder cells, fraction (f) of live *L. crispatus* (CFUs) is strongly and positively correlated to transverse relaxivity. In bladder cell mixtures, R2 but not R2* relaxivity is attenuated, giving rise to a prominent R2' component (Donnelly S. (2020)).
Figure 27:
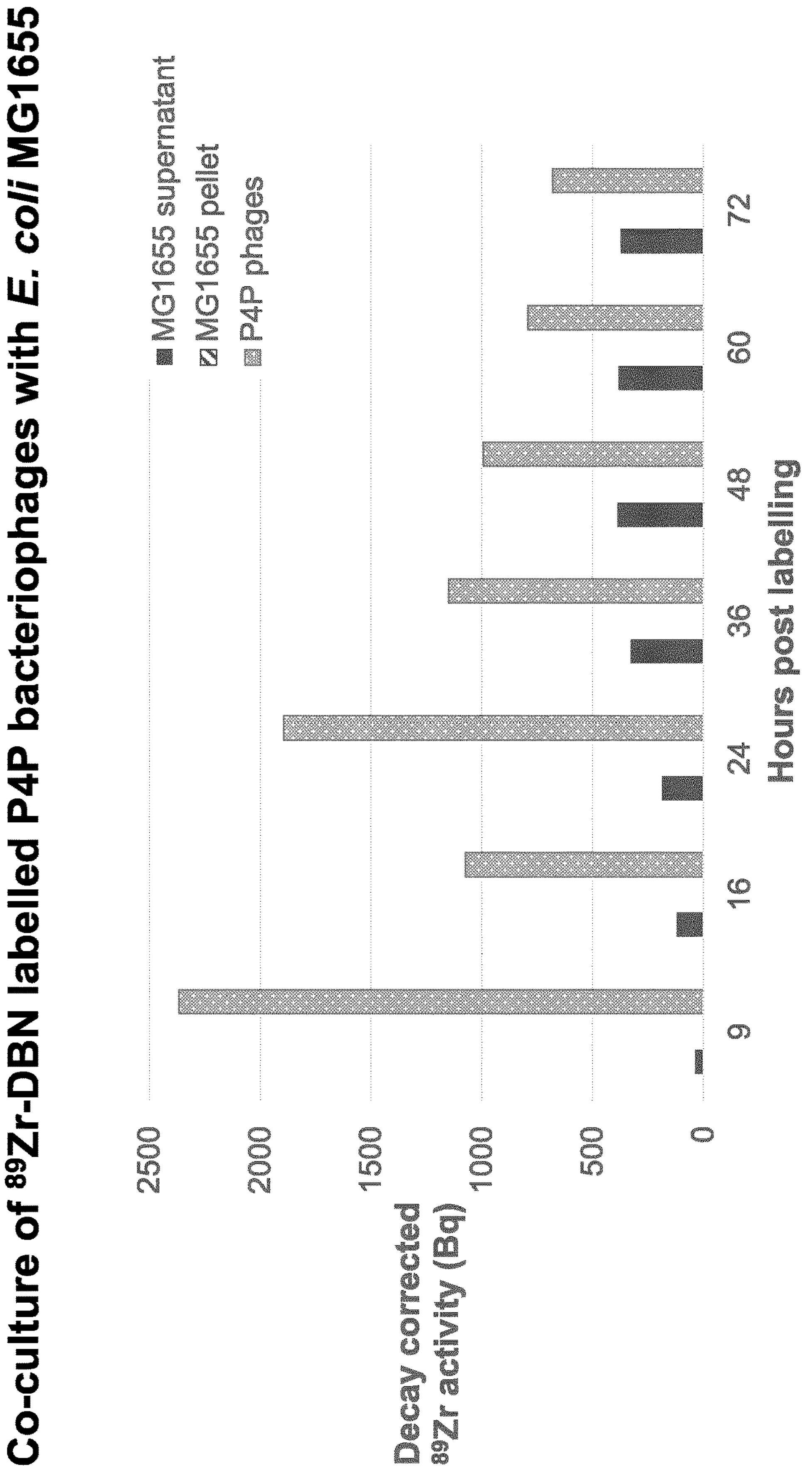
FIG. 27 shows $^{89}Zr$-DBN stability in P4P bacteriophages.

Determination of 3-D maps/images of $^{89}$Zr activity and MRI R2 and/or R2* values in animals/humans: The animal/human is placed into a hybrid PET/MRI or sequentially imaged with PET and MRI. First a baseline MRI is taken prior to the delivery of $^{89}$Zr labelled manganese dependent bacteria. This MRI 3-D data is converted to a 3-D distribution of R2 and R2*. Then PET/MRI data is collected at various times after delivery of $^{89}$Zr labelled manganese dependent bacteria to follow, in time, the extent of engraftment, gut permeability and migration. Note, as shown in FIG. 26, as the concentration of manganese dependent bacteria increases the R2 and R2* values linearly increase. However, since the bacterial R2 and R2* are in fast water exchange with the local tissue (i.e. mammalian cells), measures of R2 and R2* will not represent bacteria alone.

Generation of 3-D images of manganese dependent bacteria concentration from the PET ($^{89}$Zr 3-D activity maps) and MRI (R2 and R2* 3-D maps) data: To use the formulation given above, two values have to be determined: a) the non-specific uptake of $^{89}$Zr in the gut and in the body external to the gut i.e. NSU and NSUE respectively and b) the $^{89}$Zr activity in Bq per bacterium within the gut and external to the gut i.e. ATB (t) and ATBE (t) respectively.

Determination of NSU: A sample of stool is counted for radioactive concentration in Bq of $^{89}$Zr i.e. AC (before). Then the non-cellular debris is removed, and the sample recounted to give AC (after). Then NSU is calculated as NSU=AC (before)−AC (after).

Determination of NSUE. A blood sample and/or a saliva sample and/or a urine sample is counted for radioactive concentration in Bq of $^{89}$Zr i.e. ACE (before). Then the non-cellular debris is removed, and sample recounted to give ACE (after). Then the NSUE is calculates as NSUE=ACE (before)−ACE (after).

Determination of Bq per bacterium in the gut i.e. ATB (t): As the manganese dependent bacteria have been loaded with manganese by being exposed to physiological concentration of manganese the number of manganese atoms per bacteria will be constant. Hence, R2 and R2* increase linearly as the concentration (i.e. the number of bacteria per unit gram) will increase. Hence, ATB (t) equals the $^{89}$Zr activity (AC (after)) divided by the change in R2 and/or R2*. For stool samples, this requires measuring R2 and/or R2* in a stool sample prior to delivery of the $^{89}$Zr labelled bacteria.

$$\text{i.e. ATB}(t)=\text{AC(after)}/\Delta(\text{R2 or R2*})$$

$$\text{where } \Delta\text{R2}=\text{R2(after)}-\text{R2(before)}$$

$$\text{and } \Delta\text{R2*}=\text{R2*(after)}-\text{R2*(before)}$$

Alternatively, the concentration of live bacteria can be determined by next generation sequencing. Note that ΔR2 and/or ΔR2* can be measured under slow or fast water exchange.

Determination of Bq per bacterium external to the gut ATBE (t): As the manganese dependent bacteria have been loaded with manganese by being exposed to physiological concentrations of manganese the number of manganese atoms per bacteria will be constant. Hence, R2 and R2* increases linearly as the concentration (i.e. the number of bacteria per unit gram) will increase. By analyzing one or more of a blood sample, a urine sample or a saliva sample in the same manner as done for a stool sample then ATBE (t)=ACE (after)/Δ(R2 or R2*).

Determination of ΔR2 and/or ΔR2* from MRI: If the manganese labelled bacteria concentrate sufficiently in the gut or external to the gut at one or more locations then the needed value of ΔR2 or ΔR2* are determined from R2 and/or R2* maps before the delivery of $^{89}$Zr labelled bacteria and afterwards. Then the stool and/or blood, urine, saliva samples will not have to be analyzed for R2 and/or R2* values.

Determination of NSU and NSUE values from the PET images: This is determined from the activity of $^{89}$Zr in the PET images where the ΔR2 and ΔR2* values are zero.

Example 10: Imaging Bacteria In Vitro Using NMR/MRI by Measuring R2 in Samples This example demonstrates how using NMR or MRI to measure innate transverse relaxation rates in bacterial samples can be performed in vitro.

Phantom preparation. Samples were prepared from cultured bacteria, mounted in a gelatin phantom and imaged at 3 T. FIG. 3 illustrates an MRI cell phantom. Cells were washed to remove media components (e.g. free metal ions, proteins, etc.); loaded into Ultem wells by centrifugation at 4500×g; and then mounted in a spherical gelatin phantom (9 cm diameter). For bacteria exhibiting high R2 and R2* (>100 $s^{-1}$), bacteria were washed and serially diluted in 4% gelatin/PBS to provide samples with varying amounts of live cells for MRI. Diluted bacteria were loaded into Ultem wells and placed at 4° C. for 5 min to allow for suspended cell samples to solidify before mounting in gelatin phantoms.

MR analysis. Regions of interest (ROIs) were analyzed of each sample within each well. Mean transverse relaxivity measurements (R2, R2*, R2) within the ROI were obtained by plotting signal decay over echo time. Homogeneity of voxel-to-voxel relaxivity in MR images was also evaluated by preparing R2 and R2* maps.

FIG. 10 illustrates R2 and R2* of *L. crispatus* ATCC33820 after serial dilution in gelatin/PBS. *L. crispatus* displayed high transverse relaxation rates after dilution in gelatin/PBS. FIG. 10 shows the mean+/−SEM. Given that there was only one identifiable R2* and R2, the bacterial cells were determined to be in fast exchange with the gelatin/PBS. The total transverse relaxivity, R2* (in red) consists predominantly of the irreversible, R2 component (in blue).

FIG. 14 illustrates the Nuclear Magnetic Resonance (NMR) signal of different bacteria mounted in a gelatin phantom for MRI at 3 T. MR measurements of different bacterial species vary widely. Although there is overlap in the spin-spin relaxation signal (R2) between species of bacteria, calibration will be possible by high resolution NMR relaxometry of fecal samples, allowing for the identification of the different bacteria by relaxation rate and the number of these live bacteria by the signal amplitude at each relaxation rate. For this technique, fecal samples are processed to put the different bacteria into the slow exchange regime, either by doping the fecal bacteria with a paramagnetic salt like Mn or Gd, or by slowly reducing the hydration of the slurry containing bacteria and bacteriophage.

In all cases, the R2 component of transverse relaxivity (blue bars) dominates the total R2* signal (red bars). The outstanding signal from *L. gasseri* ATCC33323 (see FIG. 14) was found to be significantly higher than any other species tested ($p<0.05$). Both *E. coli* BL21(DE3) and *L. rhamnosus* GR-1 displayed higher relaxivity than *P. mirabilis* 296 and *S. aureus* Newman (black and gray lines, respectively). Measurements for (undiluted) *L. crispatus* ATCC33820 could not be obtained with the MRI pulse sequences used in this data set (FIG. 10 samples) to cover the range in R2 exhibited by these bacteria. However other MRI/NMR pulse sequences, such as ultrashort echo time (UTE) and zero echo time (ZTE) would be successful in quantifying R2* for undiluted samples. Bar graphs show the mean+/−SEM (* $p<0.05$, n=3-5).

FIG. 15 provides data on additional species of *E. coli* (probiotic, commensal and uropathogenic). *Escherichia coli* are detectable by MRI. Bar graphs compare MR signals from the BL21(DE3) laboratory strain of *E. coli* with select probiotic (Nissle), commensal (MG1655, 25922) and uropathogenic strains (67, AD110, GR-12, 536, J96). All *E. coli* exhibit relatively high transverse relaxation rates, with R2* consisting virtually entirely of an R2 component and little or no R2' contribution (R2*=R2+R2'). One-way ANOVA indicates that R2/R2* of Nissle (light gray lines), 25922 (dark gray lines) and AD110 (black lines) are significantly lower than most other tested strains (* $p<0.05$). Data are the mean+/−SEM (n=3-5).

Bacterial quantification. Bacteria loaded into each Ultem well were quantified by serially diluting a sample of the initial culture and plating in triplicate on the preferred agar medium. Plates were incubated either aerobically or anaerobically, depending on the bacterium, before counting CFUs. Colonies were counted at the dilution factor where 20-60 colonies were present for each replicate. CFUs loaded into each well were then calculated for comparisons and correlations of live cells to MR measurements.

Example 11: Imaging Bacteria In Vivo Using MRI by Measuring R2

This example demonstrates how understanding the transverse relaxation rates of bacteria can be applied to in vivo MRI.

In some applications, measurement of bacterial R2/R2* will be made prior to administration of a bacterial sample to a host in order to determine in vivo changes in R2 and R2* caused by the bacterial presence.

Evaluating the dispersion of bacterial probiotics or fecal microbiota transplantation (FMT). Here, bacteria with pre-evaluated R2 and R2* will be administered to an animal or human by loading microbiota into capsules and either swallowing these capsules or depositing them by tube into the gut through the esophagus or anus. Following administration, MRI sequences such as HASTE would be used at various time points to follow the bacteria based on their high relaxivity—or a hypointense region within the images. Magnetic resonance imaging may allow us to track bacterial movement through the gut and dispersion over time. Stool samples can also be obtained for MRI assessment as well as 16S rRNA gene sequencing to confirm the presence of administered bacteria as they exit the host.

Localizing tumours using the transverse relaxivity of tumour-homing bacteria. In this case the R2/R2* of tumour-homing bacteria would first be measured by MRI as in Example 10. These bacteria would then be administered to an animal with a known tumour by ingestion, infusion, or injection, including intravenous, intraarterial, subcutaneous, intraperitoneal, intramuscular, and intracranial (intrathecal or intraventricular) routes. The animal would be imaged using MR sequences such as HASTE for anatomical imaging and T2* and T2 dependent pulse sequences to extract R2* and R2, both pre- and post-bacterial administration, with various time points imaged post-administration, using the transverse relaxivity of the bacteria to follow their movement in vivo and to localize the tumour. This can be especially useful in cases with small tumours or metastases, as the bacteria may be easier to detect than the tumour(s) themselves. Contrast enhancing agents and/or nanoparticles may be used to label the bacteria prior to administration and improve detection in vivo.

Bladder cancer recurrence rates can be as high as 66% at 5 years and 88% at 15 years. BCG was originally developed as a sub cutaneous vaccine to prevent *Mycobacterium tuberculosis* [tuberculosis] infection and is an attenuated *Mycobacterium bovis* (bovine) strain (Bacillus Calmette-Guérin-BCG). BCG is currently considered the most effective management for intermediate and high-risk non-invasive bladder tumours. Transurethral resection of the bladder tumour followed by weekly intravesical instillation of high dose BCG is typical. Despite a significant reduction in recurrence and progression rates following BCG, almost half of patients will not respond and the disease might even progress. The mechanism by which the BCG vaccine prevents cancer recurrence has yet to be fully elucidated, but the BCG requires an interaction with the bladder wall. BCG binds to fibronectin with specific binding proteins, leading to the induction of $CD8^+$ T cells and natural killer cells.

Given that BCG is a bacterium and potentially can be labelled by similar methodologies as described above, this could provide several imaging applications of this technology in bladder cancer. Such applications could be used as clinical or research tools for better understanding BCG efficacy. Labelling of BCG may allow imaging of bacteria that have attached to the cancer in the bladder which may allow a clearer perspective of the clinical situation with regards to disease severity. Another application may allow the assessment of the amount of BCG maintained at the site, which may be correlated to a treatment outcome by the BCG itself, as well as other therapies. While BCG is generally considered relatively safe, in a small number of cases (~5%) there can be serious infection or other toxicities associated with its use. Therefore, the labelling and tracking of the BCG in vivo may aid its early detection of these adverse events, for example where vesico-renal BCG reflux is suspected, the bladder contents (typically urine) ascend/reverse to the ureters and to the kidneys where these microbes may pose an infection or sepsis risk. Using MRI, and/or PET imaging of bacteria like labelled BCG, infections at these sites could be detected in real time to improve treatments and outcomes of late-stage bladder cancer. Past bladder cancer applications, there is also the potential to label any vaccine with a microbial base to track the microbial diffusion and localization in the host post-administration.

Example 12: Quantifying 3D Distribution of Bacteria

Segmentation is performed in longitudinal PET/MRI acquisitions spanning the first seven days post-ingestion. Organs are manually segmented in 3D Slicer using MRI acquisitions with reference to a porcine anatomical guide. 3D regions of interest are applied to simultaneously acquired PET images to determine mean and maximum activity concentration as well as total activity in individual organs.

Dosimetry: The radiation of $^{89}$Zr-labelled bacteria is estimated to specific organs and whole-body effective dose using time activity curves obtained from repetitive imaging in the pig.

Dose may also be estimated by comparison to that reported for $^{111}$In, which has similar dosimetry to $^{89}$Zr. The pilot data in the pig indicated that 99% of ingested radioactivity was excreted similar to the time frame of non-digestible solids (i.e. gut transit time). When gut transit times are measured using the radioisotope $^{111}$In, the typical effective dose is 0.35 mSv/MBq (i.e. 28 mSv/80 MBq of $^{89}$Zr assuming similar dosimetry to $^{111}$In). Given that less than 1% of the dose migrated out of the pig's GI tract, an estimate of effective dose by comparison to intravenous injection of $^{111}$In labelled leucocytes gives 0.59 mSv/MBq (i.e. the dose from $^{89}$Zr-labelled bacteria translocating beyond the gut (less than 1 MBq) would be less than 0.6 mSv). The effective dose is dominated by activity in the gut, with the greatest organ dose likely to be large intestine: estimated from $^{111}$In studies to be 1.9 mGy/MBq. Another aspect of dosimetry relates to $^{89}$Zr-labelled bacteria. Since radiotoxicity will be dependent on bacterial radio-tolerance and radiation from neighboring cells, allowed Bq/cell is determined using functional assays.

Example 13: Imaging Manganese Dependent Bacteria In Vitro and in Vivo by Labelling with $^{89}$Zr or with Both $^{89}$Zr and $^{52}$Mn PET imaging is more sensitive than MRI R2/R2* imaging. At high concentrations of manganese dependent bacteria both $^{89}$Zr and changes in R2/R2* can be detected if the bacteria are labelled with $^{89}$Zr. As the $^{89}$Zr per bacterium will decrease with bacteria proliferation the value of $^{89}$Zr per bacterium is needed to transform a 3D image of $^{89}Zr$ to a 3D image of bacteria concentration. If the manganese dependent bacteria are grown in tissue culture with a physiological concentration of manganese, then the R2/R2* effects will be constant as the bacteria proliferate under physiological conditions when introduced into mammalian tissue. In biological tissue we have shown that these bacteria will be in fast water exchange with mammalian tissue environment and the change in R2/R2* (comparing measurements made before and then after administration of the manganese dependent bacteria) is linearly related to $^{89}Zr$ concentration (FIG. 12).

Selected strain(s) of manganese dependent bacteria will be labelled with $^{89}Zr$ with a target concentration per bacterium of (0.513q)×((surface area of bacteria)/(surface area of a sphere of 10 μm radius)). As described in previous examples, this $^{89}Zr$ labelled bacteria will be washed of unbound $^{89}Zr$ potentially mixed with other material (e.g. fecal) and introduced into the biological sample (for in vitro studies) or introduced into a living system (for in vivo studies). Prior to introduction, the sample/living system will be imaged to determine the baseline values of R2/R2*. Then at various times post introduction the sample/living system will be imaged with both PET and MRI to determine the relationship between $^{89}Zr$ activity and R2/R2* values (for in vivo studies a 3D distribution will be determined for both $^{89}Zr$ activity and R2/R2* values). If the bacteria are in the fast water exchange regime then the change in R2/R2* will be related to the bacteria concentration. With the measurement of $^{89}Zr$ activity at that location the $^{89}Zr$ per bacterium will be calculated as $^{89}Zr$ activity at a time t divided by the number of bacteria present at time t determined from the ΔR2/R2* at the same time t. The dependence of ΔR2/R2* with bacteria concentration will be calibrated for each biological system being considered. If the determination of $^{89}Zr$ per bacterium is to be made from a biological sample such as that from fecal or urine material the determination can also be made from ΔR2/R2*. But a more accurate determination can be made if the sample is processed to move from the fast water exchange regime to the slow water exchange regime. Then the absolute R2/R2* of the sample at the R2 value corresponding to the specific manganese dependent bacteria can be used instead of the change in R2 and/or R2*.

Manganese dependent bacteria can also be labelled with $^{52}Mn$ (Example 8) as well as $^{89}Zr$. Although PET cannot discriminate between $^{89}Zr$ and $^{52}Mn$ if they are both present at the same time, they can be discriminated by gamma-ray spectroscopy. ($^{89}Zr$ can be quantified by counting the 908 KeV gamma-ray which is released 99% of the time that $^{89}Zr$ decays as this gamma-ray populates an isomeric transition in $^{89}Y$. $^{52}Mn$ can be quantified by the detection of a number of different gamma-rays including one at 1,434 KeV associated with the energy levels of $^{52}Cr$ and associated with 100% of the $^{52}Mn$ decays.) Note that $^{52}Mn$ concentration per bacterium will also decrease with proliferation. However, other losses of $^{52}Mn$ due to exchange of manganese between the bacteria and the extracellular manganese will occur. Whereas the $^{89}Zr$ label will be lost due to other mechanisms such as loss from the chelation complex. These different losses of $^{52}Mn$ and $^{89}Zr$, as a function of time, can be used to calculate the non-specific binding constants and hence a more accurate estimate of $^{89}Zr$ activity per bacterium and $^{52}Mn$ activity per bacterium.

The above described methods may have a number of biomedical uses, including in vivo cell tracking of bacteria from fecal transplant material and other sources to determine efficacy of engraftment, persistence and translocation, and measuring the extent of gut bacteria permeability and migration.

The above methods may also be used to screen donors for fecal microbiota transplantation (FMT). The information on residence and transmit time of gut bacteria, along with the extent of permeability and migration of gut bacteria, can provide information on the appropriateness of the donor FMT for therapeutic purposes.

In non-invasive imaging studies of gut bacteria in large animals, including pigs, dogs, sheep, cats and rabbits, the above methods may also be used with imaging reporter genes. The use of optical reporter genes, such as bioluminescence or fluorescence, could be used for calibration of the number of $^{89}Zr$ labels per bacteria. This would allow bacterial cells to be labelled with $^{89}Zr$-DBN, as well as stably transfected with an optical reporter gene. Since the optical signal would not be diluted by cell proliferation and only report on viable cells, it could provide the number of viable bacteria in stool samples. If the same samples are counted for $^{89}Zr$, then the activity of $^{89}Zr$ per viable bacterium would be determined. This may be simpler than the stool sample processing needed in human studies where the number of viable bacteria needs to be determined by non-imaging methods, such as determining the number of colony-forming units.

While the present description largely pertains to the use of $^{89}Zr$ and $^{111}In$ as the radioisotopes, other radioisotopes may be used as described above. For example, rather than using $^{89}Zr$ for labelling with PET imaging, the $^{89}Zr$ may be substituted with $^{64}Cu$ or $^{52}Mn$. In another example, rather than using $^{111}In$ for labelling with SPECT imaging, the $^{111}In$ may be substituted with another single photon emitting radioisotope, such as $^{177}Lu$ or $^{225}AC$.

In such cases, the imaging sequence may be modified depending on the radioisotope used and the radioisotope's physical (or biological) half-life. For $^{52}Mn$, the subject may be imaged once every 5.5 days after the initial 12 hours. For $^{177}Lu$, the subject may be imaged once every 6.6 days after the initial 12 hours. For $^{225}AC$, the subject may be imaged once every 10 days after the initial 12 hours until the radioisotope is no longer detected in the subject.

Example 14: Co-Culture of $^{89}Zr$-DBN Labelled P4P Bacteriophages with *E. coli* MG1655

PreForPro (P4P) bacteriophages (LH01-Myoviridae, LL5-Siphoviridae, T4D-Myoviridae, and LL12-Myoviridae) were amplified in a liquid culture of *E. coli* MG1655, then isolated, dialyzed, filtered through a 0.2 μm membrane, and quantified before radiolabelling. $3.01\times10^9$ plaque forming units (PFUs) of these bacteriophages were radiolabelled with 1.05 MBq of $^{89}Zr$-DBN with a labelling efficiency of 36%. Unbound radiolabel was removed using a Centricon filter (nominal molecular weight limit (NMWL) 30 kDa) and $7.33\times10^6$ PFUs of radiolabelled phages were recovered.

Labelled bacteriophages were inoculated into one chamber of a co-culture apparatus with *E. coli* MG1655 in the opposite chamber, separated by a 0.2 μm filter. The co-culture was performed at 37° C. and 1 mL samples from each chamber were obtained at various time points to quantify $^{89}Zr$ activity. Samples from the bacterial chamber were pelleted at 10,000×g for 1 min to separate supernatant from bacterial pellet. Pellets were washed three times with PBS before measuring $^{89}Zr$ activity in the supernatant (not including washes), pellet, and bacteriophage samples using a well counter.

$^{89}Zr$ activity in the phage chamber was found to decrease over time as the radioactivity increased in the bacterial chamber with phage movement across the filter. Radiolabelled phages that infect and lyse *E. coli* MG1655 cells are expected in the bacterial chamber supernatant and could be detected through a plaque assay of this supernatant. While phages that bind and infect but do not lyse the bacteria are expected in the pellet, very little activity was present in this fraction.

Table 2 summarizes the $^{89}Zr$-DBN radiolabelling efficiency obtained in the various micro-organisms as elucidated above.

TABLE 2

$^{89}Zr$-DBN Radiolabelling Efficiency in Microorganisms

| | Efficiency of $^{89}Zr$-DBN Uptake (%) |
|---|---|
| Bacteria | |
| *L crispatus* ATCC33820 | 80 |
| *E. coli* Nissle | 75 |
| Human fecal microbiota | 90 |
| Bacteriophage | |
| P4P | 36 |

Example 15: Labelling of Fungi and Yeast

This example demonstrates how understanding the transverse relaxation rates of fungi and yeast can be applied to in vivo MRI.

In some applications, measurement of R2/R2* in the subject will be made prior to administration of fungi/yeast, in order to determine in vivo changes in R2 and R2* caused by the introduction of fungi or yeast.

Evaluating the dispersion of yeast from industrial contents, food, probiotics or fecal microbiota transplantation (FMT). Yeast is important in industry to produce various important substances such as ethanol (e.g. *Saccharomyces cerevisiae*), food products (e.g. *Saccharomyces cerevisiae*), and probiotics (e.g. *Saccharomyces boulardii*). Yeast is also part of the microbiome in humans and various species. While the mycobiome is smaller, both in number of species and in biomass compared to its viral and bacterial counterparts, fungi/yeast are thought to have a major influence over the rest of the microbiota and other factors such as immune development (van Tilburg Bernardes et al, 2020).

Here, $^{89}Zr$-DBN labelled fungi or yeast with pre-evaluated R2 and R2* will be administered to a subject by loading into either capsules or food and either ingesting them or depositing them by tube into the gut through the esophagus or anus. Following administration, MRI sequences such as HASTE would be used at various time points to follow the yeast or fungi based on their high relaxivity—or a hypointense region within the images. Magnetic resonance imaging would allow us to track the movement of fungi/yeast through the gut and its dispersion over time. Stool samples can also be obtained for MRI as well as 18S rRNA gene sequencing, to confirm the presence of administered fungi or yeast as they exit the host.

Evaluating the pathogenesis of clinically important yeast and fungi. The medical importance of fungi and yeast (e.g. *Candida albicans, Cryptococcus*) is vast and growing, especially in association with other chronic immunocompromised diseases such as the human immunodeficiency virus (HIV; 45 million people affected globally alone) (Rodrigues, 2020). Resurgence in fungal drug resistance is also increasing and the pathogenesis of these microbes are of great medical interest.

Given yeast have cell surface proteins that could be labelled by the methodologies described herein (e.g. $^{89}Zr$-DBN), there could be several imaging applications of this technology in tracking fungal pathogenesis, to evaluate efficacy of different treatments and drugs in real time. Labelled fungi could be administered to a subject by ingestion, infusion, or injection, including intravenous, intraarterial, subcutaneous, intraperitoneal, intramuscular, and intracranial (intrathecal or intraventricular) routes. The subject would be imaged using MR sequences such as HASTE for anatomical imaging using T2* and T2 dependent pulse sequences to extract R2* and R2, both pre- and post-fungal administration, with various time points imaged post-administration, using the transverse relaxivity of the fungi to follow their movement in vivo.

Experiment 16: Labelling of Viral-Like Particles from Fungi and Yeast for Detecting Medically Important Organisms While bacteria are afflicted by bacteriophages, fungi and yeast are also afflicted by their own types of viruses. The widely used and industrially important, *Saccharomyces cerevisiae* for example, is known to have double stranded RNA viruses which are not dissimilar to parts of mammalian dsRNA viruses, but also single-stranded RNA viruses that are closest in sequence to some bacterial bacteriophages. There are also "virus-like" entities or prions that are self-propagating amyloids of various chromosomally encoded proteins (Wickner R B). Given that some of these viral entities are known to have specificities to very selective target hosts, it may be possible to surface label them as described for bacteriophages of bacteria above. These labelled phages may then be delivered via ingestion or injected into the host whereby they rendezvous with their specific fungal or yeast target thereby illuminating it in the same way that bacteriophages attach to their bacterial hosts.

In one embodiment is disclosed a method of imaging fungi and yeast, either directly (for example, using $^{89}Zr$-DBN or $^{52}Mn$ or $^{111}In$), or indirectly by labelling (for example, with $^{89}Zr$-DBN) which are known to infect the yeast of interest, allowing those particles to come into contact with the fungi or yeast of interest, and using PET/MRI and PET/CT to image the organism, since they will be co-located with the labelled phage particle. In a corollary embodiment, non-labelled phage particle can be utilized to attenuate the radio-signal when they find, and infect, and lyse, the radio-labelled fungi or yeast.

Although the present invention and its advantages have been described in detail, it should be understood that various changes, substitutions and alterations can be made herein without departing from the scope of the invention as defined by the appended claims. Moreover, the scope of the present application is not intended to be limited to the particular embodiments of the process, composition of matter, means, methods and steps described in the specification. All references cited herein are hereby incorporated by reference.

REFERENCES

1. Mezzanotte L, van't Root M, Karatas H, Goun E, Lowik C. In vivo molecular bioluminescence imaging: new tools and applications. *Trends Biotechnol.* 2017; 35(7):640-652.

2. Boerman O C, Laverman P, Oyen W. FIAU: from reporter gene imaging to imaging of bacterial proliferation. *Am J Nucl Med Mol Imaging.* 2012; 2(3):271-272.
3. Goldhawk D, Lemaire C, McCreary C, et al. Magnetic resonance imaging of cells overexpressing MagA, an endogenous contrast agent for live cell imaging. *Mol Imaging.* 2009; 8(3):129-139.
4. Donnelly S, Thompson R, Prato F, Gelman N, Burton J, Goldhawk D. Magnetic resonance imaging of commensal and pathogenic bacteria. In: *Imaging Network of Ontario.;* 2019.
5. Ordonez A, Weinstein E, Bambarger L, et al. A systematic approach for developing bacteria-specific imaging tracers. *J Nucl Med.* 2017; 58(1):144-150.
6. Hess S, Alavi A, Werner T, Hoilund-Carlsen P. Molecular imaging of bacteria in patients is an attractive fata morgana, not a realistic option. *J Nucl Med.* 2018; 59(4):716-717.
7. Shan L. Magnetic iron microbeads coupled with HEA-125 monoclonal antibody against epithelial cell adhesion molecule. In: *Molecular Imaging and Contrast Agent Database;* 2011.
8. Fox M, Gaudet J, Foster P. Fluorine-19 MRI contrast agents for cell tracking and lung imaging. *Magn Reson Insights.* 2016; 8(1):53-67.
9. Bansal A, Pandey M, Demirhan Y, et al. Novel 89Zr cell labeling approach for PET-based cell trafficking studies. *EJNMMI Res.* 2015; 5(19).
10. Thiessen J, Sykes J, Keenliside L, et al. Feasibility of multi-week PET studies with a single injection of 89Zr-phosphate on a clinical PET/MRI. In: *30th Annual Meeting of the European Association of Nuclear Medicine.;* 2017.
11. Swank G, Deitch E. Role of the gut in multiple organ failure: bacterial translocation and permeability changes. *World J Surg.* 1996; 20(4):411-417.
12. Bhatt N, Pandya D, Wadas T. Recent Advances in Zirconium-89 Chelator Development. *Molecules.* 2018; 23(3):E638.
13. Hampton H, Watson B, Fineran P. The arms race between bacteria and their phage foes. *Nature.* 2020; 577(7790):327-336.
14. Cisek A, Dabrowska I, Gregorczyk K, Wyzewski Z. Phage Therapy in Bacterial Infections Treatment: One Hundred Years After the Discovery of Bacteriophages. *Curr Microbiol.* 2017; 74(2):277-283.
15. Sengupta, A., Quiaoit, K., Thompson, R., Prato, F., Gelman, N., and Goldhawk, D. (2014) Biophysical features of MagA expression in mammalian cells: implications for MRI contrast, Frontiers in Microbiology 5, Article 29.
16. Berg, E., Gill, H., Jan Marik, J., Ogasawara, A., Williams, S., van Dongen, G., Vugts, D., Cherry, S., and Tarantal, A. (2020) Total-Body PET and Highly Stable Chelators Together Enable Meaningful 89Zr-Antibody PET Studies up to 30 Days After Injection, J Nucl Med 61, 453-460.
17. Morariu, V., and Benga, G. (1977) Evaluation of a Nuclear Magnetic Resonance Technique for the Study of Water Exchange Through Erythrocyte Membranes in Normal And Pathological Subjects, Biochim Biophys Acta 469, 301-310.
18. Hazlewood, C., Chang, D., Nichols, B., and Woessner, D. (1974) Nuclear Magnetic Resonance Transverse Relaxation Times Of Water Protons In Skeletal Muscle, Biophys J 14, 583-606.
19. Saab, G., Thompson, R., Marsh, G., Picot, P., and Moran, G. (2001) Two-Dimensional Time Correlation Relaxometry of Skeletal Muscle In Vivo at 3 Tesla, Magn Reson Med 46, 1093-1098.
20. Lev-Sagie, A., Goldman-Wohl, D., Cohen, Y., Dori-Bachash, M., Leshem, A., Mor, U., Strahilevitz, J., Moses, A., Shapiro, H., Yagel, S., and Elinav, E. (2019) Vaginal microbiome transplantation in women with intractable bacterial vaginosis, Nat Med 25, 1500-1504.
21. Jin Y, Kong H, Stodilka R Z, Wells R G, Zabel P, Merrifield P A, Sykes J, Prato F S. Determining the minimum number of detectable cardiac-transplanted 111 In-tropolone-labelled bone-marrow-derived mesenchymal stem cells by SPECT. *Phys Med Biol.* 2005; 50:4445-4455.
22. Blackwood K J, Lewden B, Wells R G, Sykes J, Stodilka R Z, Wisenberg G, Prato F S. In vivo SPECT quantification of transplanted cell survival after engraftment using 111In-tropolone in infarcted canine myocardium. *J Nuc Med.* 2009; 50:927-935.
23. Ordonez A A, Wintaco L Z, Mota F, Restrepo A F, Ruiz-Bedoya C A, Reyes C F, Uribe L G, Abhishek S, D'alessio F R, Holt D P, Dannais R F, Rowe S P, Castillo V R, Pomper M G, Granados U, Jain S K. *Imaging Enterobacterales infections in patients using pathogen-specific positron emission tomography. Sci TransL Med.* 13, eabe9805(2021).
24. Donnelly S. (2020) *The development of bacterial magnetic resonance imaging for microbiota analyses*. Western University Electronic Thesis and Dissertation Repository. 7381.
25. Rodrigues M L, Nonanchuk J D (2020). Fungal diseases as neglected pathogens: a wake-up call to public health officials. PLOS Neglected Tropical Diseases 14(2): e0007964.
26. Wickner R B, Fujimura T, Esteban R, Viruses and prions of *Saccharomyces cerevisiae*. Adv Virus Res. 2013:86:1-36. Doi: 10.1016/6978-0-12-394315-6.00001-5.PMID: 23498901; PMCID: PMC4141569
27. van Tilburg Bernardes E, Pettersen V K, Gutierrez M W, et al., *Intestinal fungi are causally implicated in microbiome assembly and immune development in mice*. Nat Commun 11, 2577 (2020).

We claim:

1. A method of quantitatively imaging a 3-D distribution of a concentration of bacteria that has a physiological concentration of manganese in a subject, the method comprising:

providing bacteria having high concentrations of manganese, labelling the bacteria with a radioisotope;

introducing the radioisotope labelled bacteria into the subject;

detecting a manganese Magnetic Resonance Imaging (MRI) signal to determine the quantity of the bacteria;

simultaneously detecting a signal from the radioisotope with Positron Emission Tomography (PET), and determining the radioisotope activity per bacteria cell utilizing the signal from the radioisotope and the MRI signal, to calculate the 3-D distribution of the concentration of the bacteria in the subject.

2. The method of claim 1, wherein the radioisotope is $^{89}Zr$, $^{64}Cu$, or $^{52}Mn$.

3. The method of claim 1, the method further comprising:

functionally and/or structurally imaging the subject, to obtain a first image, prior to the introducing of the radioisotope labelled bacteria;

introducing the bacteria into the subject; and functionally and/or structurally imaging the subject again, to obtain a second image;

comparing the first image and the second image, wherein changes in imaging indicate location of the bacteria.

4. The method of claim 3, wherein the bacteria is mixed with fecal matter before introduction into the subject.

5. The method of claim 3, wherein the functional and/or structural imaging is through MRI and the first image and the second image are R2/R2* images.

6. The method of claim 1, wherein the bacteria are at a concentration and with a concentration of metal per bacterium effective for detection by MRI alone.

7. The method of claim 1, wherein the method quantitatively images a 3-D distribution of the concentration of bacteria, and where in the radioisotope label is $^{89}Zr$ and/or $^{52}Mn$, and wherein the imaging comprises MRI, which detects a manganese-dependent MRI signal to determine the quantity of the bacteria, and PET, which detects the radioactivity on said bacteria to calculate radioactivity per bacterium which allows the 3-D distribution of the concentration of the bacteria to be calculated from the 3-D concentration of radioactivity.

8. The method of claim 1, wherein the MRI imaging comprises measuring a difference in MRI relaxivity, measured before and after the labeled bacteria are introduced into the subject, to allow calculation of the bacteria concentration.

9. The method of claim 1, wherein the manganese-dependent bacteria are labelled on the cell membrane with $^{89}Zr$ and in the intracellular manganese pool with $^{52}Mn$.

10. The method of claim 9 wherein differential reduction in the PET signal of $^{89}Zr$ and $^{52}Mn$ is used to calculate $^{89}Zr$ activity per bacterium and/or $^{52}Mn$ activity per bacterium.

11. The method of claim 1, wherein the bacteria are further labelled with $Mn^{2+}$.

12. The method of claim 1, wherein the MRI relaxivity as a function of time detects the number of bacteria per unit time post installation of the bacteria.

* * * * *